(12) United States Patent
Kieffer et al.

(10) Patent No.: US 7,335,646 B2
(45) Date of Patent: Feb. 26, 2008

(54) COMPOSITIONS AND METHODS FOR REGULATED PROTEIN EXPRESSION IN GUT

(75) Inventors: Timothy Kieffer, Edmonton (CA); Anthony Cheung, Edmonton (CA)

(73) Assignee: Engene, Inc., Vancouver, British Columbia (CA)

( * ) Notice: Subject to any disclaimer, the term of this patent is extended or adjusted under 35 U.S.C. 154(b) by 0 days.

(21) Appl. No.: 09/804,409

(22) Filed: Mar. 12, 2001

(65) Prior Publication Data

US 2002/0155100 A1  Oct. 24, 2002

Related U.S. Application Data

(60) Provisional application No. 60/254,464, filed on Dec. 8, 2000, provisional application No. 60/188,796, filed on Mar. 13, 2000.

(51) Int. Cl.
| | |
|---|---|
| *A01N 43/04* | (2006.01) |
| *A01N 63/00* | (2006.01) |
| *A01N 65/00* | (2006.01) |
| *A61K 31/70* | (2006.01) |

(52) U.S. Cl. ..................... 514/44; 424/93.1
(58) Field of Classification Search ............ 514/44; 435/320.1, 325; 536/23.1, 23.5; 434/93.1; 800/8

See application file for complete search history.

(56) References Cited

U.S. PATENT DOCUMENTS

| | | | | |
|---|---|---|---|---|
| 5,821,235 | A | 10/1998 | Henning et al. | 514/44 |
| 5,837,693 | A * | 11/1998 | German et al. | 514/44 |
| 5,989,910 | A | 11/1999 | Mermod et al. | 435/325 |
| 6,001,816 | A * | 12/1999 | Morsy et al. | 514/44 |
| 6,004,941 | A | 12/1999 | Bujard et al. | 514/44 |
| 6,004,944 | A | 12/1999 | Rothman et al. | 514/44 |
| 6,015,709 | A | 1/2000 | Nitesan | 435/366 |
| 6,110,456 | A | 8/2000 | During | 424/93.2 |
| 6,503,887 | B1 * | 1/2003 | During | 514/44 |

FOREIGN PATENT DOCUMENTS

| | | |
|---|---|---|
| CA | 2 364 417 | 10/2000 |
| WO | WO 9625487 A1 * | 8/1996 |
| WO | 98/11779 | 3/1998 |
| WO | 00/06204 | 2/2000 |
| WO | 2 782 732 | 3/2000 |
| WO | 00/57921 | 10/2000 |
| WO | WO 00/57921 | 10/2000 |

OTHER PUBLICATIONS

Crystal R. Transfer of genes to humans: early lessons and obstacles to success. Science. 1995, vol. 270, pp. 404-410.*
Deonarain M. Ligand-targeted receptor-mediated vectors for gene delivery. Exp. Opin. Ther. Patents. 1998, vol. 8, No. 1, pp. 53-69.*
Miller N. et al. Targeted vectors for gene therapy. FASEB J. 1995, vol. 9, pp. 190-199.*
Anderson W. Human gene therapy. Nature. 1998, vol. 392, supplement, pp. 25-30.*
Verma et al. Gene therapy-promises, problems, and prospects. Nature. 1997, vol. 389, pp. 239-242.*
Yoon J. Recent advances in insulin gene therapy for type 1 diabetes. Trends in Mol. Med. 2002, vol. 8, No. 2, pp. 62-68.*
Corbett J. K cells: a novel target for insulin gene therapy for the prevention of diabetes. Trends in Endocrin. Metabol. 2001, vol. 12, No. 4, pp. 140-142.*
Cheung A. et al. Glucose-dependent insulin release from genetically engineered K cells. Science. 2000, vol. 290, pp. 195 1962.*
Buettner R. Correction of diet-induced hyperglycemia, hyperinsulinemia, and skeletal muscle insulin resistance by moderate hyperleptinemia. Am. J. Physiol. Endocrinol. Metab. 2000, vol. 278, pp. E563-E569.*
Shalitin, et al. (2003) Int. J. Obes. Relat. Metab. Disord., 27(8): 869-74, Abstract Only.*
Lukic, et al. (1998) Dev. Immunol. 6(102): 119-128, Abstract Only.*
Boylan, et al. (1997) J. Biol. Chem., 272(28): 17438-43.*
Eck, et al. (1996) Goodman & Gilman's The Pharmacological Basis of Therapeutics, 9th Ed., McGraw-Hill, New York, NY., pp. 77-101.*
Gorecki (2001) Expert Opin. Emerging Drugs 6(2): 187-98.*
Ma, et al. (2001) Curr. Pharma. Biotechnol., 2: 1-17.*
van Beusechem, et al. (2000) Gene Therapy, 7: 1940-46.*
Langer, et al. (2003) Sci. Am., 288(4): 51-57.*
Chiesi, et al. (2005) Trends in Pharmacol. Sci., 22(5): 247-54.*
Liu, et al. (2005) Drugs of Today, 41(5): 345-62.*
Hocker, et al. (2001) Gastroenterology, 121(1): 43-55 (Abstract Only).*
Hocker, et al. (2004) Ann. NY. Acad. Sci., 1014: 97-109.*
Tseng, et al. (1993) Proc. Natl. Acad. Sci., USA, 90: 1992-96.*
Dimaline, et al. (1993) Am. J. Physiol., 264(3 Pt 1): G583-88 (Abstract Only).*
Hocker, et al. (2001) Gastroenterology, 121: 43-55.*
Cheung, et al. (2000) Science, 290 : 1959-62.*
Zhao, et al. (2003) Vaccine, 21: 4022-35.*
Nathan (1999) Annals of Internal Medicine, 120(5): 440-41.*
Lee et al.; Glucagon Gene 5'-Flanking Sequences Direct Expression of Simian Virus 40 large T Antigen to the Intestine, Producing Carcinoma of the Large Bowel in Transgenic Mice; J. Biol. Chem, vol. 267, No. 15; May 1992; pp. 10705-10708.
Gajic et al.; Multiple *cis*-Acting Domains Mediate Basal and Adenosine 3',5'-Monophosphate-Dependent Glucagon Gene Transcription in a Mouse Neuroendocrine Cell Line; Endocriniology, vol. 132, No. 3; 1993; pp. 1055-1062.
Henning; Gene transfer into the intestinal epithelium; Advanced Drug Review, vol. 17; 1995; pp. 341-347.

(Continued)

*Primary Examiner*—Joseph Woitach
*Assistant Examiner*—Robert M. Kelly
(74) *Attorney, Agent, or Firm*—Pillsbury Winthrop Shaw Pittman LLP

(57) ABSTRACT

The invention provides compositions and methods useful for treating disorders treatable by producing a protein in a regulatable manner in a mucosal cell or tissue of an animal. The treatment methods include in vivo and ex vivo methods, including transplanting in vitro transformed cells that secrete the protein into a mammalian subject.

44 Claims, 16 Drawing Sheets

OTHER PUBLICATIONS

Kolodka et al.; Gene Therapy for Diabetes Mellitus in Rats by Hepatic Expression of Insulin; Proc. Natl. Acad. Sci. USA, vol. 92; Apr. 1995; pp. 3293-3297.

Efrat et al.; Glucagon Gene Regulatory Region Directs Oncoprotein Expression to Neurons and Pancreatic α Cells; Neuron, vol. 1; Sep. 1998; pp. 605-613.

Boylan et al.; Cell-specific Expression of the Glucose-dependent Insulinotropic Polypeptide Gene in a Mouse Neuroendocrine Tumor Cell Line; The Journal of Biological Chemistry, vol. 272, No. 28; Jul. 1997; pp. 17438-17443.

Croyle et al.; In vitro and in vivo asessment of adenovirus 41 as a vector for gene delivery to the intestine; Gene Therapy, vol. 5; 1998; pp. 645-654.

Yeung et al.; Glucose-dependent insulinotropic polypeptide gene expression in the stomach: revealed by a transgenic mouse study, in situ hybridization and immunohistochemical staining; Molecular and Cellular Endocrinolohgy, vol. 154; 1999; pp. 161-170.

Rutter et al.; Regulation of Mammalian Gene Expression by Glucose; News Physiol. Sci., vol. 15; Jun. 2000; pp. 149-154.

During et al.; Peroral gene therapy of lactose intolerance using an andeno-associated virus vector; Nature Medicine, vol. 4, No. 10; Oct. 1998; pp. 1131-1135.

During et al.; An Oral Vaccine Against NMDAR1 with Efficacy in Experimental Stroke and Epilepsy; Science; vol. 287; Feb. 2000; pp. 1453-1460.

Morsy et al.; Leptin gene therapy and daily protein administration: a comparative study in the ob/ob mouse; Gene Therapy, vol. 5; 1998; pp. 8-18.

During, et al. "Peroral gene therapy of lactose intolerance using an andeno-associated virus vector," *Nature Medicine*, (Oct. 1998), vol. 4, No. 10, pp. 1131-1135.

During, et al., "An Oral Vaccine Against NMDAR1 with Efficacy in Experimental Stroke and Epilepsy," *Science*, (Feb. 25, 2000), vol. 287 pp. 1453-1460.

Morsy, et al., "Leptin gene therapy and daily protein administration: a comparative study in the ob/ob mouse," *Gene Therapy*, (1998), vol. 5 , pp. 8-18.

Welsh; Gene Therapy in Diabetes Mellitus: Promises and Pitfalls; Current Opinion in Molecular Therapeutics, vol. 1, No. 4; 1999; pp. 464-470.

Mizuno et al.; Successful Culture and Sustainability in Vivo of Gene-Modified Human Oral Mucosal Epithelium; Human Gene Therapy, vol. 10; Mar. 1999; pp. 825-830.

Mitanchez et al; Regulated Expression of Mature Human Insulin in the Liver of Transgenic Mice; FEBS Letters, vol. 421; 1998; pp. 285-289.

Lee et al.; Remission in Models of Type 1 Diabetes by Gene Therapy Using a Single-Chain Insulin Analogue; Nature, vol. 408; Nov. 2000; pp. 483-488.

Mitanchez et al.; Glucose-Stimulated Genes and Prospects of Gene Therapy for Type 1 Diabetes; Endocrine Reviews, vol. 18, No. 4; 1997; pp. 520-540.

* cited by examiner

GIP Promoter atctctccag tcccttcctc aaccttctga gaacaggcaa actccaccat gattggctta
taaatcgtta tatggaccta ctaaggatgt aacaactggg agcatgctta cctagcatgt
ccgaaacccg gagttcagtc cctagcactg cacaatctca gtccttatga agtagaggga
agatcagagg ttcaaggaca acatcaattt gagaccagcc tgggctactt accaaagaaa
gaaagagaga aataaataaa tagatagata aataaataaa taagtaaata aatatcttat
ggctggagag ttggttcagt gtttaagagc acttattgtg gggttgggga tttagctcag
tggtagagcg tttgcctagg aagctcaagg ccctgggttc ggtccccagc tccggaaaca
aaacaaaaca aaacaaaaac aaacaaacaa acaaaaaacc ctgtctggaa aacacctaaa
taaagatata tatatataat atatatacat ataatatata tatgatatat atatatatat atatctttgt
ggaggaagct ataccttct ttcttgagcc tccaacacat aaatgtgccc tgtcatccca
ttcatattgc cccaagtggg aaaccatgtg actataaact ctaagttcct agtcactagg
aactctcaag acacctacct caggcagcat cacttccgga gtgccaccat tatcagttaa
catccacatc tgggattcag atcccagatc ccttctgttc cctcagaagt cacctacagc
tttgtggggg tgcccccttcc ctcagagagt gccacccgag ttgaccctca ccaaggcaac
cctttgtacc cacagaatcc aacaggaagt aggggaaga acagccggcc ctgtgcccag
aaaaaaagag gggagggaga aggggtgct cagcctacca ccgggcaggt cccagataac
actgcagata cccaaatgtt aatcacccat tagcacaggc ccagagcaaa ggggaaagtg
attaggtgta taatgggtt cactgggcag gaccagtggg cttgagcttc aaagataaga
ggttttcagg ttaatcagca ccctgtggtg tgtggatata aggaagctaa cacagggtct
tgaagcaaga tcctgag Mouse chromogranin A (Chga) gene, promoter region.
ACCESSION L31361

1 ccgaaattac ccactacgtt ggaattctat aagggttggg tttgctgttt tgtttacagc
   61 tgcgtctttg gcacccagca cagctgagtg gttctaagcc cacgtcgatg cttaacacat
  121 ggttgttgaa tgaatacacg cgaagccggt tctcatttag gggcatgagt aggcagaggt
  181 gtgggcagga agcaggaaag agcggaaaca ggtgcggaca gaaaggaggg gctctgaagg
  241 atgccagtca gtgccaaact gtcatccaga taccaggttc actgtggccc taggccaggc
  301 tgcacggggc ttcccatgtg gtctgcccag ggtgagagca gaactgcggt gggcggggca
  361 gaaggaaacc aaccaggaag cagggttgca cccaaattat ccaggtttta agtacattta
  421 agagacaagg ctgggctgtt gaaggtcaga ggtgtccctg gggtgctgga ctaggactga
  481 ccacttctgt tttagtttaa tggtgagaac tgcctcacac tgctacctgc cttacttgcc
  541 ccttgagagc tgtgagccta ggacccaccc atgtgtgggt tggaccttca gtcacacact
  601 gaacgtgtgt gaagccactg gttgtcagag cagggctctc ggcactgagg aagcagtgac
  661 cactatcccc tatcaaataa caattaaata cacacagaat gcgaggcaca caactgagtt
  721 tcaggagagg cctcgctcag gcaagggtt caagaggctt ctgtgggacc cgctggatgt
  781 tccagggagt tcttaaagat gggcgtgcct ccagccaagt gaaatcaaga gaaagtacg
  841 cgaagtatag gaaaactcag cagtctggag aggtaaatag gggaggaatc cgaggctcag
  901 agacaggagt gacttgccca cggacgcaca gcaagttggc aggtggagtt cagctgtgcc
  961 accttctgaa gccgggtacc ctttacagcc accagataca agcgggatag agacagctga
 1021 tggagaagct ggaggtgggg ggcgggaccc cgaaggtggg gaaagggcgc ggggggcgg
 1081 tcctatgacg taatttcctg ggtgtgtgcg cgcgtgtgcg tgcgtgtgcg tgtatataaa
 1141 agccggcata gcattgctgc tgctgccgcc gccaccgcca ccatcaccgc tgttaccacc
 1201 accgctactg cagtgttccc gctggtgcag agctttggta gccagactac agacccactc
 1261 ccgccatcct cctgcagcag ctcgtccact ctttccgcac cgtccggctc gctatgcgc
//

Figure 14

Mus musculus secretogranin II (Scg2) gene, promoter and exon 1, complete sequence.
ACCESSION   AF037451

```
   1 gggaactttc tctagctctt tcattagggg ccctgtgttc catctaatag ctgactgtga
  61 gcatccactt ctgtgcttgc caggcactgg catagcctca caagagacag ctatatcagg
 121 gtcttgtcag caaaatcttt ctggcatatg caatagtgtc tgggtttggt ggttgtatat
 181 gggctggatc cccgggtggg gcagtctctg gatggtcttt ccttccgtct tagctccaaa
 241 ctttgtctct gtaactcctt ccatgggtac tttgtttccc attctaagaa ggagcaaagt
 301 atccacactt ccttcttctt ccttcttctt gagttttgca aatgccacaa aactttcaaa
 361 gccttctgaa tagcctctc tttagtgctt tccaatgtat attaaaataa tctatctttc
 421 atccccattg attaaagcct tcttaaagcc agaaaactat attcattttt ttcttttccc
 481 agtagttcac aaactatctg gcacctcata agcatcataa ctcagttggt gggtagataa
 541 aattggaatg tgattgttca gtcagcagag acttttagag gacctcatac aacaagattc
 601 tctcagttct cagaaatata tttcagtata tacagggtta gaggactcac atctttaata
 661 aaataaagtt aaaaatttag acctgtataa attattaagg tacctaatca agttccacgg
 721 caaagtacag ccatggttat gaattataaa tccaagaagc ggtgggttaa ctctgacatt
 781 gttccttgga tggttctcat tcattgaagt tagtcacctc aacttactca accaaaacct
 841 agaagtattt ctgtggtact atgttctctt gatgccaaga gggctctagg catatgaaaa
 901 tctctcaatc tctctccctc tctctccccc ttccacccc actctctctc ttctagcagt
 961 aatccctccc ttcctggtag gcagtatgtt ttttggagca cagtttctta gctatctctt
1021 gcaacacctg attttgctga agatttgaat ggcctcatat agaagtatca acaacttgag
1081 cgtctgtgaa ctctcatttt gacactgtgc tgaaagaatt ggagttgatt ctcattaaaa
1141 aaaaaattaa gcatctcacc tttttgctc aaactaaaca gttttaaaac agttctgcct
1201 ggagtcatga tatgaaatac gatctatcat atttgcaatg ttctgttcaa ttgtggctgc
1261 accaggaaat gagaagctat ttcttatag gcacaaataa aaagatagtc attatctgta
1321 aaattcttat gacatggcag caagcccaag aaaacctttct aaacaaggcg tgaaaacgca
1381 gagatgtcct tgcaattagt catgtctatc tgacagattt cttcctttct aagggaattt
1441 gtgctgaaca ttttatttcg agcctcagag ataaaagaag ggggaagaag ctgtagtttt
1501 tgctacataa gacaggtggc gtaagcatgc aacgcttaa aaaaatatct aaagtgattg
1561 ttttctctcg gattctttga aaaagctcgc ctgcgctggg gtttgaggct gagccggtga
1621 cgtcagcgtg gaatgcggag tcaggcgccc aggctctcta taagccgagg agctgtccgg
1681 tgctgaaacg gcccgagccc tcactcagcg gcagagagga gcatgcttgg agccttccac
1741 ataatataag acagaggtaa
//
```

Mus musculus glucokinase gene, 5' flanking region.
ACCESSION   U93275

```
   1 agctttaggt gtgtgaatat ctactttggt gctagggcct tggtcatact aagtaagttt
  61 ccccttcact ggggtgtacc agtttaccct ggactgtcta agcaacaaga aggatagaca
 121 tggcctacca cagatttcat gtctgccact ggctatgtca gaacatgtag gagcttttgg
 181 aatcagtgaa acaggtattt tcagactgcc ttccctgcgt ggggctttcc cgaagccata
 241 ttttcctag agtcagcctt tcccagctga ggacaagctg tactggacag atgccagcca
 301 cttgaactgg gaatacatgg tcatttaggc agctggctta tctcatccat ggtacttgat
 361 ggcttcgggt cagcacctca cagaaagttc agacgggagg cttccgagaa aacagagaag
 421 caggcaggag atcctgcagg caatcctcct gctccacagc ctgcatggac ttccctcagc
 481 cttagtgcgt gtgggtccca tctgagaaca ttggttatat gttattttca aaccgatctg
 541 cctttaagga gtggaagaaa aaaactgtgg tgtttgggct acctttatga taatggcctt
 601 ttcatcctcc taataaatat tgccaagtag ggtagattct atacgaaagc tcttaaccca
 661 tggtattagc aaatcatgta ggtgctaata atgaatactg gatgcagtca gtacagggat
```

Figure 15

```
 721 ataaaatgga atgtaagagc ctgttgctat gaatggttag ctaactagat gttgtacaag
 781 aaatgttgac gttatgacgt gtggaaactt ggtattgaag atgtggactc gaaactttgt
 841 ggatttttg atgccatgat aaaaatgtga agaatactgt tccttaccaa aaagaagaag
 901 aagaaggaga aggaggagga agaggaggag gaggaagaag aggggagga agaagaagag
 961 aaggaggagg aagaggagga ggaggaagaa gaggaggagg aggaagaaga agagaaggag
1021 gaggactagg aggaggagga gaagaaggag aaggggaagg agagagtagc cagaacattt
1081 ggggtgccat cagaatacca gatactccag acatagtcac agaaggactg gtttgtttgt
1141 taaataggtg ctttgaaaag tttgtgggga aacctgcagt gagattgtgt gtcttagaaa
1201 tgataggcaa gattcatcca caagaatgcg acaagatggc tgcctgaaca agccctgaac
1261 attaacagca ccagtagacc tgcttacacg gaagaaagca atctcatagg ccctcacccc
1321 aaacaaagac tacagacagc agaggaactg gagagcagga gaaattgggt ctccctttta
1381 tgagccccct aactggttgt caaatactca atggtcagcc ctgaaatcat atgcacaaag
1441 taatactagc gcaactgaac agattgtagc tgtgtgtgtg tgtgtaatga taacaaagaa
1501 gaaaaggccc catgttagag agggagcaag gtgggcatgg aggtatggaa ggagttggaa
1561 ggaggggtga gaaggggaaa gtgatgtaat tatcttttaa tttataaaaa aataaaaaat
1621 gggctggtga gatggctcag tgggtaagag cacccgactg cttcttccga aggtctggag
1681 ttcaaatccc agcaaccaca tggtggctca caaccatccg taacgagatc tggcgccctc
1741 ttctggagtg tctgaagaca gctacagtgt acttacatat aataaataaa taaatctttt
1801 aaaaaaaata aaaaataaaa tattagaata aaatgtagag gaatatttt aatttaacaa
1861 cttgggtgtg gcaaaagctt tcttcaacaa aaacttaatc cctcagataa gaaaagacta
1921 gaatccacga cgtggataga tacttctgta tgatgcaaga cactatttat caggttgtaa
1981 cttgagcaga acttgagttg taacttgttg ggaaacacaa caccccttggc aaacaaaaga
2041 ttactagata ttttagatga aatataaaaa tactttccac aactgatagg taggaaacag
2101 ttcaatagta atataattat tgaacaaata atccttaaaa gaagaaatcc agaggaatag
2161 caagttaggg gaagagaggg tgtgtgtgtg tgtgtgtgcg cgcacattta tagccaaaat
2221 agatgatata cttaaatgaa catgccatta aaacccatta ttttgcatac agtttacata
2281 tgctaatgaa tacttaaaaa aaaaacattg ggattggaga gaaatggctc agtggttaag
2341 agttcaattc ccagcaacca catgattgct cacaaccatc tgtaatggga tctgatgcct
2401 tcttctggta tgtctgaaga aagtgaccgt gtacttataa ttataaataa ataaatcttt
2461 aaccaaaaaa cccccataat ttcaacaaca gatatgtcct ggtctgaggc ttccaggcat
2521 agaaatagaa acacacagag tgtggagcca gtgcggttca ggtccgccat tccagttcag
2581 gcttcagacc aagagaaagg gaaaagaaga gacaagcaac aag
```

H.sapiens adenosine deaminase (ADA) gene 5' flanking region and exon 1 (and joined CDS).
ACCESSION X02189

```
   1 tccaggaaat gcgcgatcca ggccggcggg cggggcgggg gctccggcga gagggcgggc
  61 cccgggaacg gcggcgggcg gggcgggagg cggggcccgg cccgttaaga agagcgtggc
 121 cggccgcggc caccgctggc cccagggaaa gccgagcggc caccgagccg gcagagaccc
 181 accgagcggc ggcggaggga gcgacgccgg ggcgcacgag ggcacc
```

Homo sapiens mRNA for pre-proinsulin.
ACCESSION X70508

MALWMRLLPLLALLALWGPDPAAAFVNQHLCGSHLVEALYLVCGERGFFYTPKTRREA
EDLQVGQVELGGGPGAGSLQPLALEGSLQKRGIVEQCCTSICSLYQLENYCN"

```
   1 gctgcatcag aagaggccat caagcacatc actgtccttc tgccatggcc ctgtggatgc
```

Figure 16

```
 61 gcctcctgcc cctgctggcg ctgctggccc tctggggacc tgacccagcc gcagcctttg
121 tgaaccaaca cctgtgcggc tcacacctgg tggaagctct ctacctagtg tgcggggaac
181 gaggcttctt ctacacaccc aagacccgcc gggaggcaga ggacctgcag gtggggcagg
241 tggagctggg cgggggccct ggtgcaggca gcctgcagcc cttggccctg gaggggtccc
301 tgcagaagcg tggcattgtg gaacaatgct gtaccagcat ctgctccctc taccagctgg
361 agaactactg caactagacg cagcccgcag gcagcccccc acccgccgcc tcctgcaccg
421 agagagatgg aataaagccc ttgaaccagc
```

Homo sapiens leptin (LEP), mRNA.
ACCESSION XM_004625

"MHWGTLCGFLWLWPYLFYVQAVPIQKVQDDTKTLIKTIVTRINDISHTQSVSSKQKVTG
LDFIPGLHPILTLSKMDQTLAVYQQILTSMPSRNVIQISNDLENLRDLLHVLAFSKSCHLP
WASGLETLDSLGGVLEASGYSTEVVALSRLQGSLQDMLWQLDLSPGC"

```
   1 tctgttttca ggcccaagaa gcccatcctg ggaaggaaaa tgcattgggg aaccctgtgc
  61 ggattcttgt ggctttggcc ctatctttc tatgtccaag ctgtgcccat ccaaaaagtc
 121 caagatgaca ccaaaaccct catcaagaca attgtcacca ggatcaatga catttcacac
 181 acgcagtcag tctcctccaa acagaaagtc accggtttgg acttcattcc tgggctccac
 241 cccatcctga ccttatccaa gatggaccag acactggcag tctaccaaca gatcctcacc
 301 agtatgcctt ccagaaacgt gatccaaata tccaacgacc tggagaacct ccgggatctt
 361 cttcacgtgc tggccttctc taagagctgc cacttgccct gggccagtgg cctggagacc
 421 ttggacagcc tgggggggtgt cctggaagct tcaggctact ccacagaggt ggtggccctg
 481 agcaggctgc aggggtctct gcaggacatg ctgtggcagc tggacctcag ccctgggtgc
 541 tgaggccttg aaggtcactc ttcctgcaag gactacgtta agggaaggaa ctctggcttc
 601 caggtatctc caggattgaa gagcattgca tggacacccc ttatccagga tctgtcaat
 661 ttccctgact cctctaagcc actcttccaa aggcataaga ccctaagcct cctttgctt
 721 gaaaccaaag atatatacac aggatcctat tctcaccagg aaggggggtcc acccagcaaa
 781 gagtgggctg catctgggat tccaccaag gtcttcagcc atcaacaaga gttgtcttgt
 841 cccctcttga cccatctccc cctcactgaa tgcctcaatg tgaccagggg tgatttcaga
 901 gagggcagag gggtaggcag agcctttgga tgaccagaac aaggttccct ctgagaattc
 961 caaggagttc catgaagacc acatccacac acgcaggaac tccagcaac acaagctgga
1021 agcacatgtt tatttattct gcattttatt ctggatggat ttgaagcaaa gcaccagctt
1081 ctccaggctc tttggggtca gccagggcca ggggtctccc tggagtgcag tttccaatcc
1141 catagatggg tctggctgag ctgaacccat tttgagtgac tcgagggttg ggttcatctg
1201 agcaagagct ggcaaaggtg gctctccagt tagttctctc gtaactggtt tcatttctac
1261 tgtgactgat gttacatcac agtgtttgca atggtgttgc cctgagtgga tctccaagga
1321 ccaggttatt ttaaaaagat ttgttttgtc aagtgtcata tgtaggtgtc tgcacccagg
1381 ggtggggaat gtttgggcag aagggagaag gatctagaat gtgttttctg aataacattt
1441 gtgtggtggg ttcttttggaa ggagtgagat cattttctta tcttctgcaa ttgcttagga
1501 tgttttttcat gaaaatagct ctttcagggg ggttgtgagg cctggccagg caccccctgg
1561 agagaagttt ctggcccctgg ctgaccccaa agagcctgga gaagctgatg ctttgcttca
1621 aatccatcca gaataaaacg caaagtgctg aaagccattt gttggggcag tggtaagctc
1681 tggctttctc cgactgctag ggagtggtct ttcctatcat ggagtgacgg tcccacactg
1741 gtgactgcga tcttcagagc aggggtcctt ggtgtgaccc tctgaatggt ccagggttga
1801 tcacactctg ggtttattac atggcagtgt tcctatttgg ggcttgcatg ccaaattgta
1861 gttcttgtct gattggctca cccaagcaag gccaaaatta ccaaaaatct tgggggggttt
1921 ttactccagt ggtgaagaaa actccttttag caggtggtcc tgagacctga caagcactgc
1981 taggcgagtg ccaggactcc ccaggccagg ccaccaggat ggcccttccc actggaggtc
2041 acattcagga agatgaaaga ggaggtttgg ggtctgccac catcctgctg ctgtgttttt
```

Figure 17

2101 gctatcacac agtgggtggt ggatctgtcc aaggaaactt gaatcaaagc agttaacttt
2161 aagactgagc acctgcttca tgctcagccc tgactggtgc tataggctgg agaagctcac
2221 ccaataaaca ttaagattga ggcctgccct cagggatctt gcattcccag tggtcaaacc
2281 gcactcaccc atgtgccaag gtggggtatt taccacagca gctgaacagc caaatgcatg
2341 gtgcagttga cagcaggtgg gaaatggtat gagctgaggg gggccgtgcc caggggccca
2401 cagggaaccc tgcttgcact ttgtaacatg tttactttc agggcatctt agcttctatt
2461 atagccacat cccttgaaa caagataact gagaatttaa aaataagaaa atacataaga
2521 ccataacagc caacaggtgg caggaccagg actatagccc aggtcctctg atacccagag
2581 cattacgtga gccaggtaat gagggactgg aaccagggag accgagcgct ttctggaaaa
2641 gaggagtttc gaggtagagt ttgaaggagg tgagggatgt gaattgcctg cagagagaag
2701 cctgttttgt tggaaggttt ggtgtgtgga gatgcagagg taaaagtgtg agcagtgagt
2761 tacagcgaga ggcagagaaa gaagagacag gagggcaagg gccatgctga agggaccttg
2821 aagggtaaag aagtttgata ttaaaggagt taagagtagc aagttctaga gaagaggctg
2881 gtgctgtggc cagggtgaga gctgctctgg aaaatgtgac ccagatcctc acaaccacct
2941 aatcaggctg aggtgtctta agccttttgc tcacaaaacc tggcacaatg gctaattccc
3001 agagtgtgaa acttcctaag tataaatggt tgtctgtttt tgtaacttaa aaaaaaaaaa
3061 aaaagtttgg ccgggtgcgg tggctcacgc ctgtaatccc agcactttgg gaggccaagg
3121 tgggggatc acaaggtcac tagatggcga gcatcctggc caacatggtg aaacccgtc
3181 tctactaaaa acacaaaagt tagctgagcg tggtggcggg cgcctgtagt cccagccact
3241 cgggaggctg agacaggaga atcgcttaaa cctgggaggc ggagagtaca gtgagccaag
3301 atcgcgccac tgcactccgg cctgatgaca gagcgagatt ccgtcttaaa aaaaaaaaaa
3361 aaaaagtttg ttttaaaaa aatctaaata aaataacttt gccccctg Homo sapiens cholecystokinin (CCK), mRNA.
ACCESSION XM_003225

"GSAAGLLRLETPSQLRPNPKAMNSGVCLCVLMAVLAAGALTQPVPPADPAGSGLQRAE
EAPRRQLRVSQRTDGESRAHLGALLARYIQQARKAPSGRMSIVKNLQNLDPSHRISDRD
YMGWMDFGRRSAEEYEYPS"

1 ggctcagctg ccgggctgct ccggttggaa acgccaagcc agctgcgtcc taatccaaaa
 61 gccatgaaca gcggcgtgtg cctgtgcgtg ctgatggcgg tactggcggc tggcgccctg
121 acgcagccgg tgcctcccgc agatcccgcg ggctccgggc tgcagcgggc agaggaggcg
181 ccccgtaggc agctgagggt atcgcagaga acggatggcg agtcccgagc gcacctgggc
241 gccctgctgg caagatacat ccagcaggcc cggaaagctc cttctggacg aatgtccatc
301 gttaagaacc tgcagaacct ggacccagc cacaggataa gtgaccggga ctacatgggc
361 tggatggatt ttggccgtcg cagtgccgag gagtatgagt accctcccta gaggacccag
421 ccgcatcag cccaacggga agcaacctcc caacccagag gaggcagaat aagaaaacaa
481 tcacactcat aactcattgt ctgtggagtt tgacattgta tgtatctatt tattaagttc
541 tcaatgtgaa aaatgtgtct gtaagattgt ccagtgcaac cacacacctc accagaattg
601 tgcaaatgga agacaaaatg ttttcttcat ctgtgactcc tggtctgaaa atgttgttat
661 gctattaaag tgatttcatt ctgcc CCK Promoter (Rat)
ACCESSION S70690

1 aattcgcgcg ctaagccgca ttattcacgt ttccagacat gtcacaaata cagctaattc

Figure 18

```
 61 ctacaacctg agctgtgtca tgggggggggg gggaatcacc cacagcattt aatctgctgc
121 tgttttaaac acgttgcttc taagtaaaga gaccgctaga gccacaacca ggaacctaac
181 tgctgctggc atcacttgcc ttttcatagt ctccctcagc cggaaccccc ccacgctggg
241 tgccttctct atttagaaag agtttctaag cctttctcct tcaccctaga ctggcaaggt
301 tgagggtagg ctgagggttg caagactgtg agaaaaggga gcccctctct tcttcttgct
361 cggtgagtat ctcagccaag atcctcacca cccagtggaa tcccgtaact ctagaggaaa
421 ggaagaactc tagaggacgg gaagatcatt gcaagctccc ctagatgtgc gagcccagcc
481 cgctccactc agccagccag agcttgaggg tgcttgagac actctctggc gccacttcgc
541 gaccaaaatc atcggtagat gtaggctggt gagaagtcat cttgggaaga aatggaaacc
601 tttccccaa aggctttccg cacaaaaggc aagagctgca cccaggatct taaaattctg
661 taagacgaga atccacgagg ccaactgtga ttgagttctg aaaaattgag agccctactc
721 ccctctctca cttgtgggag cccactcagg tctgaagtgc tcccagagaa catgccagaa
781 ttacatttgc tgacacctag tctgtgaggg tcccccggtt tcctggaagg atttgatccc
841 tcaaagctca ctaaacagtg gtcagcttct ccattccaga caaactcctg cttctctccg
901 ggagtagggg tggcaccctc cctgaagagg actcagcaga ggcaccgaac agggtgggga
961 ggaaagctgt ttagataaag aggaggactc atacaaagta ccccgcctgg gaggggctat
1021 cctcattcac tgggccgttt cccttctccc ggggggccac ttcgatcggt ggtctctcca
1081 gtggctgcct ctgagcacgt gtcctgccgg actgcgtcag cactgggtaa acagatgact
1141 ggctgcgtac cgggcggggc tatttaagag gagtcgccct gccgcctgcc ctcaacttag
1201 ctggacagca gccgttggaa accgccaagc cagctgactc cgcatccgaa ggtaagtggc
1261 tggcagatcc aagaatcatg agtgtgaaga actggcctgt agctttgcat ctattgccgt
1321 ttagtctttc cattttctgt gccttccctc acttgacagc tg
```

Human messenger RNA for growth hormone (presomatotropin).
ACCESSION V00519

"MATGSRTSLLLAFGLLCLPWLQEGSAFPTIPLSRPFDNAMLRAHRLHQLAFDTYQEFEE
AYIPKEQKYSFLQNPQTSLCFSESIPTPSNREETQQKSNLELLRISLLLIQSWLEPVQFLRSV
FANSLVYGASDSNVYDLLKDLEEGIQTLMGRLEDGSPRTGQIFKQTYSKFDTNSHNDDA
LLKNYGLLYCFRKDMDKVETFLRIVQCRSVEGSCGF"

```
  1 cgaaccactc agggtcctgt ggacagctca cctagctgca atggctacag gctcccggac
 61 gtccctgctc ctggcttttg gcctgctctg cctgccctgg cttcaagagg gcagtgcctt
121 cccaaccatt cccttatcca ggcctttga caacgctatg ctccgcgccc atcgtctgca
181 ccagctggcc tttgacacct accaggagtt tgaagaagcc tatatcccaa aggaacagaa
241 gtattcattc ctgcagaacc cccagacctc cctctgtttc tcagagtcta ttccgacacc
301 ctccaacagg gaggaaacac aacagaaatc caacctagag ctgctccgca tctccctgct
361 gctcatccag tcgttggctgg agcccgtgca gttcctcagg agtgtcttcg ccaacagcct
421 ggtgtacggc gcctctgaca gcaacgtcta tgacctccta aaggacctag aggaaggcat
481 ccaaacgctg atggggaggc tggaagatgg cagcccccgg actgggcaga tcttcaagca
541 gacctacagc aagttcgaca caaactcaca caacgatgac gcactactca gaactacgg
601 gctgctctac tgcttcagga aggacatgga caaggtcgag acattcctgc gcatcgtgca
661 gtgccgctct gtggagggca gctgtggctt ctagctgccc gggtggcatc cctgtgaccc
721 ctccccagtg cctctcctgg ccctggaagt tgccactcca gtgcccacca gccttgtcct
781 aataaaatta agttgcatc
//
```

Figure 19

Rat GIP Promoter −1 to −1894 bp.

(-1894)
5'_GAGTGGCGACAGGCTGCTGCTAGCAGGCTCTACACTGAGCTAACCCCACCCATAT
ATATACATAGTTACTATTAGCTTTATTTATATTTTTAAGATTATCATTATATATATAG
TACACTGTAGTGTCTAGATACACAGAAGAGGCATCGGTCTCTTACAGAGAGCCACC
ATGTGGTTGCTGGGGATTGAACTCATACCTCTGGCAGAGCAGTCGGTGCTCTTAACG
CTGAGCCATCTCTCCAGCGCCCCCAAAGCCCAGCTTTTAAAAATATTTTAAAATTTCT
TTCTACAGATTGTTTTATGTATATGAGTGTTTTGTGTGTATGCGTTGATGTGTGTACT
GTGTGCATGGCACATGCCAGTGGGCCACAGACAGAGGGACATGAGATTCCCCTGAA
ACTTGGAGTTACAGATGGCTGTGGGCTGCCATGTGAGTGAGCGCCTTTGGAACCAAA
CCTGGGTCCTGCACAAAAGCAACAAGCACTCTTAATCGTTGAGCCACCTCTCCAACC
CCTTGATATTTCTTTTCGTTGGTGCATTAAAATTGATAAACAGAGGGTTTTCTTTATT
TAAAGATTTATTTATTTTATGTGAGTACACTGTTGCTCTCTTCAGACACATAGAAGAG
GGCATTGCTGGATTCTGCTACAGATGGTTGTGAGCCACCATGTGGTTGCTGGGAGTT
AAACTCAGGACCTCTGGAAGAGCAGTCAGTGCTCTTAACCACTGAGCCATCTCTCCA
GTCCCTTCCTCAACCTTCTGAGAACAGGCAAACTCCACCATGATTGGCTTATAAATC
GTTATATGGACCTACTAAGGATGTAACAACTGGGAGCATGCTTACCTAGCATGTCCG
AAACCCGGAGTTCAGTCCCTAGCACTGCACAATCTCAGTCCTTATGAAGTAGAGGGA
AGATCAGAGGTTCAAGGACAACATCAATTTGAGACCAGCCTGGGCTACTTACCAAA
GAAAGAAAGAGAGAAATAAATAAATAGATAGATAAATAAATAAATAAGTAAATAA
ATATCTTATGGCTGGAGAGTTGGTTCAGTGTTTAAGAGCACTTATTGTGGGGTTGGG
GATTTATCTCAGTGGTAGAGCGTTTGCCTAGGAAGCTCAAGGCCCTGGGTTCGGTCC
CCAGCTCCGGAAACAAAACAAAACAAAACAAAAACAAACAAACAAACAAAAAACC
CTGTCTGGAAAACACCTAAATAAAGATATATATATATAATATATATACATATAATAT
ATATATGATATATATATATATATATCTTTGTGGAGGAAGCTATACCTTTCTTTCTT
GAGCCTCCAACACATAAATGTGCCCTGTCATCCCATTCATATTGCCCCAAGTGGGAA
ACCATGTGACTATAAACTCTAAGTTCCTAGTCACTAGGAACTCTCAAGACACCTACC
TCAGGCAGCATCACTTCCGGAGTGCCACCATTATCAGTTAACATCCACATCTGGGAT
TCAGATCCCAGATCCCTTCTGTTCCCTCAGAAGTCACCTACAGCTTTGTGGGGGTGC
CCCTTCCCTCAGAGAGTGCCACCCGAGTTGACCCTCACCAAGGCAACCCTTTGTACC
CACAGAATCCAACAGGAAGTAGGGGGAAGAACAGCCGGCCCTGTGCCAGAAAAAA
AGAGGGGAGGGAGAAGGGGGTGCTCAGCCTACCACCGGGCAGGTCCAGATAACA
CTGCAGATACCCAAATGTTAATCACCCATTAGCACAGGCCCAGAGCAAAGGGGAAA
GTGATTAGGTGTATAATGGGGTTCACTGGGCAGGAGCAGTGGGCTTGAGCTTCAAA
GATAAGAGGTTTTCAGGTTAATCAGCACCCTGTGGTGTGTGGATATAAGGAAGCTAA
CACAGGGTCTTGAAGCAAGATC_3' (-1)

Figure 20

COMPOSITIONS AND METHODS FOR REGULATED PROTEIN EXPRESSION IN GUT

This application claims priority to Provisional Application Ser. No. 60/188,796, filed Mar. 13, 2000 and Provisional Application Ser. No. 60/254,464, filed Dec. 8, 2000.

TECHNICAL FIELD

This invention relates to regulatable production of proteins in the gut, and more particularly to nutrient regulated production of glucose-lowering factors from gut endocrine cells.

BACKGROUND

Peptides and proteins, by virtue of their conformational versatility and functional specificity, have been used in treating a host of diseases including diabetes, hemophilia, cancer, cardiovascular disorders, infectious diseases and arthritis (Russell C. S. & Clarke L. A. *Clin Gent* 55(6):389 (1999); Ryffel B. *Biomed environ Sci* 10:65(1997); Koths K. *Curr Opin Biotechnol* 6:681 (1995); Buckel P. *Trends Pharmacol Sci* 17:450 (1996)). Presently, more than two thirds of the approved biotech medicines are systemic protein drugs. With recent advances in the field of functional genomics, proteomics and genetic engineering, an increasing number of protein drugs are entering the biopharmaceutical market.

Originally, protein drugs were purified from animal tissues or human serum. Protein-based pharmaceuticals have gone through several stages of improvement to reach the current state of clinical application. For example, the biopharmaceutical industry now uses genetically engineered yeast and bacteria to manufacture recombinant human proteins (Scopes R. K. *Biotechnol Appl Biochem* 23:197 (1996)). This groundbreaking technology has overcome the health risk and shortages that plagued the first generation of protein drugs, and has consequently improved the therapeutic value of proteins. However, despite these advances, broad usage of proteins as therapeutics is still hampered by difficulties in purifying recombinant proteins in active forms and the high cost of manufacturing procedures (Berthold W. & Walter J. *Biologicals* 22:135(1994); Scopes R. K. *Biotechnol Appl Biochem* 23:197 (1996)). Additionally, protein drugs face barriers to their entry into the body. When taken orally, they are susceptible to break down by enzymes in the gastrointestinal tract (Wang W. *J Drug Target* 4:195 (1996); Woodley J. F. *Crit Rev Ther Drug Carrier Syst* 11:61 (1994)).

Other routes of protein delivery explored include infusion pumps (Bremer et. al., *Pharm Biotechnol* 10:239 (1997)) transdermal delivery (Burkoth T. L. *Crit Rev Ther Drug Carrier Syst* 16:331 (1999)), microencapsulation (Cleland J. L. *Pharma Biotechnol* 10:1 (1997)) and inhalation (Gonda I. *J Pharm Sci* 89:940 (2000)). Currently, subcutaneous and intravenous administration by needle injection is the route of choice for delivering protein therapeutics. Unfortunately, this mode of delivery is less than ideal because protein concentrations often are not maintained within a therapeutic range or provide appropriate delivery kinetics. Furthermore, effective treatment with protein drugs usually requires frequent needle injections that can cause local reactions and discomfort, hence resulting in poor patient compliance (Jorgensen J. T. *J Pediatr Endocrinol* 7:175(1994)). These and other factors limit the therapeutic application of many drugs and ultimately hinder their commercial potential. Therefore, it is axiomatic to identify new delivery methods for protein therapeutics.

Insertion of genes encoding specific therapeutic proteins into cells of the body has been used to solve the aforementioned delivery problems in treating diseases. This methodology is referred to as gene therapy and it promises to be the new direction in protein delivery. By this approach, cells in the body can be transformed into 'bioreactors', manufacturing sufficient quantities of therapeutic proteins and hence eliminating the need for frequent needle injections. Currently, gene therapy can be categorized into two general approaches (Drew J. & Martin L-A. In: Lemoine N. R. (ed) *Understanding Gene Therapy*. Springer-Verlag, New York, Chp. 1: pp 1-10 (1999)).

In the first approach, referred to as in vivo gene therapy, a gene is introduced in a form that allows its absorption by cells located within the living host. For example, a therapeutic gene is packaged into the genome of viruses such as retrovirus, adeno-associated virus or adenovirus. The recombinant virus containing the therapeutic gene is then introduced into a living organism and allowed to infect cells within the organism. Through the infection process, the virus incorporates its genome containing the therapeutic genes into the genomic structure of the host cell. As a result, the infected cell expresses the therapeutic gene.

The second approach involves in vitro transfer of genetic material to cells removed from the host organism. Following successful incorporation of a gene into the cell's genome, the transformed cells are implanted back into the host. This gene transfer method is referred to as ex vivo gene therapy.

Both in vivo and ex vivo gene therapy offer physicians the power to add or modify specific genes resulting in disease cure (Friedmann T. In: Friedmann T (ed) *The Development of Human Gene Therapy*. Cold Spring Harbor Laboratory Press, Cold Spring Harbor. Chp 1:pp 1-20 (1999)). Clinical applications of this technology are being studied in a wide range of diseases, including cancer, cardiovascular disorders, metabolic diseases, neurodegenerative disorders, immune disorders and other genetic or acquired diseases ((Friedmann T. In: Friedmann T (ed) *The Development of Human Gene Therapy*. Cold Spring Harbor Laboratory Press, Cold Spring Harbor. Chp 1:pp 1-20 (1999); Drew J. & Martin L-A. In: Lemoine N. R. (ed) *Understanding Gene Therapy*. Springer-Verlag, New York, Chp. 1: pp 1-10 (1999)). Sustained therapeutic concentrations of numerous proteins have been achieved after stable introduction of genes that encode the proteins into cells by gene therapy methodologies. However, for some disorders, regulated delivery of the therapeutic protein is required. For example, insulin replacement therapy for diabetic patients ideally requires that the appropriate amount of insulin be delivered during meals. Likewise, optimal effectiveness of appetite suppressants may be achieved via meal-dependent release. Therefore, to deliver such therapeutic proteins, a release system triggered by a signal or stimuli, such as a meal, is optimal.

A particular disease well suited for timed delivery is diabetes mellitus, a debilitating metabolic disease caused by absent (type 1) or insufficient (type 2) insulin production from pancreatic β-cells (Unger, R.H. et al., *Williams Textbook of Endocrinology* Saunders, Philadelphia (1998)). β-cells are specialized endocrine cells that manufacture and store insulin for release following a meal (Rhodes, et. al. *J. Cell Biol.* 105:145(1987)) and insulin is a hormone that facilitates the transfer of glucose from the blood into tissues where it is needed. Patients with diabetes must frequently monitor blood glucose levels and many require multiple daily insulin injections to survive. However, such patients rarely attain ideal glucose levels by insulin injection (Turner, R. C. et al. *JAMA* 281:2005(1999)). Furthermore, prolonged elevation of insulin levels can result in detrimental side effects such as hypoglycemic shock and desensitization of the body's response to insulin. Consequently, diabetic patients still develop long-term complications, such as cardiovascular diseases, kidney disease, blindness, nerve damage and wound healing disorders (UK Prospective Diabetes Study (UKPDS) Group, *Lancet* 352, 837 (1998)).

Gene therapy represents a promising means to achieve physiologic delivery of therapeutic peptides such as insulin for the treatment of diabetes (Leibowitz, G. & Levine, F. *Diabetes Rev.* 7:124 (1999)). Surrogate cells that express the incorporated gene, process and store the encoded protein, and secrete insulin in regulated fashion therefore affords a treatment for diabetes. Controlling plasma insulin levels by coupling insulin production to changing nutrient requirements of the body also reduces the side effects associated with insulin injection. Accordingly, there is a need for controlled release of proteins to achieve effective treatment of diabetes and other diseases in humans. The present invention satisfies this need and provides related advantages.

SUMMARY

The present invention is based, in part, on the production of transformed gut cells that produce insulin in response to glucose. Transformed glucose-responsive cells present in the gut of animals are able to secrete insulin at physiological levels that restore normal glucose homeostasis in diabetic animals. Thus, gut endocrine cells are suitable targets for therapeutic introduction of nucleic acid encoding proteins, ex vivo or in vivo, whose production in an animal in response to a signal or stimuli (e.g., a nutrient) provides a therapeutic benefit.

The invention therefore provides methods of generating a mucosal cell that produces a protein in response to a nutrient, and compositions including a mucosal cell that produces a protein in response to a nutrient. In one embodiment, a method includes contacting a mucosal cell with a polynucleotide comprising an expression control element in operable linkage with a nucleic acid encoding a protein under conditions allowing transformation of the cell; and identifying a cell transformant that produces the protein in a nutrient-regulatable manner, thereby generating a mucosal cell that produces a protein in response to a nutrient. In another embodiment, a composition includes an isolated or cultured mucosal cell that produces a protein regulatable by a nutrient, wherein expression of the protein is conferred by a transgene comprising an expression control element in operable linkage with a nucleic acid encoding the protein.

The invention therefore also provides methods of treating a subject having or at risk of having a disorder treatable by producing a protein in a tissue. In one embodiment, a method includes implanting one or more mucosal cells that produce a protein in response to a nutrient into the tissue in an amount effective for treating the disorder. Exemplary implantable tissues include mucosal (e.g., gastrointestinal tract) and non-mucosal (e.g., liver, pancreas or muscle) tissues.

Mucosal cells included in the invention include cells that respond to nutrient, which increases expression (e.g., via a nutrient-regulatable expression control element) or secretion of the protein (e.g., secrete a synthesized protein in response to a signal or stimuli, i.e., a "secretagogue").

Nutrients included are natural and non-natural ingestible compounds, such as a sugar, fat, carbohydrate or starch, an amino acid or polypeptide, a triglyceride, a vitamin, a mineral, or cellulose. Nutrient-regulatable elements include a gut endocrine promoter, such as a glucose-dependent insulinotropic polypeptide (GIP) promoter. Nutrient-regulatable elements include finctional variants thereof (e.g., point mutation) or a functional subsequence of a full-length regulatable element (deleted sequence). Expression control elements in operable linkage with a nucleic acid encoding the protein, can further include a vector (e.g., a viral vector).

Mucosal cells included in the invention are obtained from a subject, such as a mammal (e.g., human), are obtained from a tissue or organ of the gastrointestinal tract or are derived from a cultured cell line of gut origin. Exemplary tissues where mucosal cells can be obtained include the gastrointestinal tract, large or small intestine (jejunum, duodenum), stomach, esophagus, buccal or mouth tissue. Mucosal cells also include those that can or are adapted for growth in mucosum, even for short periods of time. Mucosal cells include endocrine and non-endocrine cells, K-cells, stem cells, L-cells, S-cells, G-cells, D-cells, I-cells, Mo-cells, Gr-cells and entero-endocrine cells.

Invention compositions and methods include therapeutic proteins such as insulin, leptin, GLP-1, GLP-2, cholecystokinin, a glucagon antagonist, Ghrelin, growth hormones, clotting factors, or antibodies.

The invention therefore also provides methods of treating a subject having, or at risk of having, a disorder treatable by producing a therapeutic protein in a mucosal tissue. In one embodiment, a method includes contacting mucosal cells in the subject that have been transformed with a polynucleotide, for example, an expression control element in operable linkage with a nucleic acid encoding the therapeutic protein, with a nutrient that induces production of the protein in an amount effective to treat the disorder.

Conditions and disorders treatable with the invention methods and compositions include hyperglycemic conditions, such as insulin-dependent and -independent diabetes or where fasting plasma glucose levels are greater than 110 mg/dl; obesity or an undesirable body mass.

The invention therefore also provides animal and genetic models. In one embodiment, a non-human transgenic animal that produces a therapeutic protein (e.g., insulin) in a mucosal tissue is provided. In one aspect, therapeutic protein production does not naturally occurr in the mucosal tissue of the animal, is conferred by a transgene present in the mucosal tissue, and the transgene includes a polynucleotide including an expression control element in operable linkage with a nucleic acid encoding the protein, wherein production of the protein in the mucosal tissue of the animal is responsive to the nutrient. In one aspect, the protein comprises insulin. The transgenic animal can therefore be made resistant to developing a hyperglycemic condition. A transgenic animal having or at risk of having a hyperglycemic condition can therefore be made to have less glucose or less likely to develop hyperglycemia. In another aspect, the animal is a mouse (e.g., diabetic or hyperglycemic or obese mouse). In yet another aspect, the expression control element conferring expression comprises a nutrient-regulatable element, a functional variant thereof, or a functional subsequence thereof. In still another aspect, the expression control element includes a glucose-inducible promoter, for example, a glucose-dependent insulinotropic polypeptide (GIP) promoter. Expression of the protein in the animal can be conferred in gastrointestinal tract, intestine/gut, stomach.

Cells or tissues of the transgenic animal that produce insulin in response to the nutrient can be isolated. Cells that express protein and also can be isolated include K cells, stem cells and endocrine or non-endocrine cells.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 14 are nucleotide sequences of rat GIP (SEQ. ID. NO. 18) and mouse chromagranin A gene promoter regions (SEQ. ID. NO. 5).

FIG. 15 are nucleotide sequences of promoter and exon 1 of mouse secretogranin II (Accession no. AF037451) (SEQ. ID. NO. 6) and a 5' portion of mouse glucokinase gene promoter (Accession no. U93275) (SEQ. ID. NO. 7).

FIG. 16 are nucleotide sequences of a 3' portion of mouse glucokinase gene promoter (Accession no. U93275), human adenosine deaminase gene promoter region (Accession no. X02189) (SEQ. ID. NO. 8); and human pre-proinsulin amino adic sequence (SEQ. ID. NO. 9), and 60 bp of a 5' region of pre-proinsulin (SEQ. ID. NO. 10).

FIG. 17 are nucleotide sequences of the remaining 3' portion of human pre-proinsulin (SEQ. ID. NO. 12) and a 5' portion of the human leptin gene cDNA (SEQ. ID. NO. 11).

FIG. 18 are nucleotide sequences of the remaining 3' portion of human leptin (SEQ. ID. NO. 14), human CCK amino acid (SEQ. ID. NO. 13) and nucleotide sequences and 60 bp of rat CCK promoter (SEQ. ID. NO. 15).

FIG. 19 are nucleotide sequences of the remaining 3' portion of rat CCK promoter and amino acid (SEQ. ID. NO. 16) and nucleotide sequences of human growth hormone (SEQ. ID. NO. 17).

FIG. 20 is the sequence for the rat GIP promoter fromito −1 to −1894 bp (SEQ. ID. NO.19).

DETAILED DESCRIPTION

Figure 1:
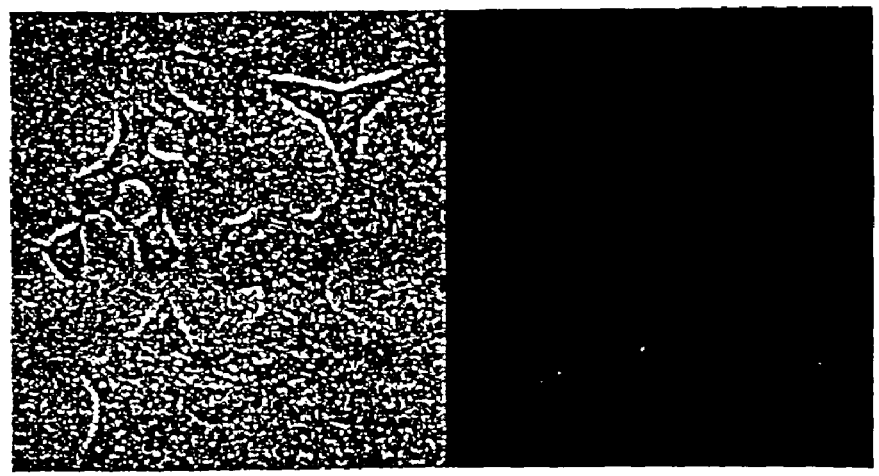
FIG. 1 shows visualization of green fluorescence protein (GFP) expression driven by the GIP promoter in tumor-derived intestinal endocrine cells, STC-1. The left panel shows a sample bright-field population of cells. The same field is seen in the right panel under fluorescence allowing identification of GFP-expressing cells. Fluorescent cell clusters were selected and expanded in culture to generate the K cell line, GTC-1.

The invention is based, in part, on the targeted production of a protein in a tissue of animals at levels sufficient to provide therapy. More specifically, the invention includes methods of targeting expression of any protein of interest to endocrine cells in the gastrointestinal tract of a subject such that the protein is released into the bloodstream of the subject in a regulated manner. Genetic constructs including an expression control element (e.g., promoter) that targets gene expression to gut endocrine cells operably linked to nucleic acid encoding a therapeutic protein can be used. Vhen the gene construct is incorporated into the endocrine cells, the encoded protein will be expressed and secreted in a regulated manner. The transformed endocrine cells expressing the protein encoded by the nucleic acid of interest can secrete a therapeutically effective amount of the protein into the bloodstream of the subject upon feeding of a substance (e.g., nutrient) that increases production of the protein.

Delivery of a genetic construct comprised of a GIP promoter operably linked to a human insulin gene in mice successfully targeted expression and secretion of human insulin by K cells in the gastrointestinal tract of transgenic offspring. Furthermore, the production of human insulin in the transgenic animals was meal regulated. The amount of insulin secreted by the cells was sufficient to protect the transgenic mice from developing diabetes after destruction of pancreatic β-cells. Insulin production was also sufficient to provide normal glucose homeostasis. Thus, introduction of a gene encoding therapeutic proteins such as insulin into meal-regulated endocrine cells in the gut of an animal, either by in vivo or by ex vivo methods (e.g., transplanting in vitro transformed cells that secrete insulin into an animal), can be used to treat disorders treatable by production of a protein.

In accordance with the invention, there are provided methods of generating a mucosal cell that produces a protein regulatable by a nutrient. A method of the invention includes contacting a mucosal cell with a polynucleotide comprising an expression control element in operable linkage with a nucleic acid encoding a protein under conditions allowing transformation, and identifying a transformed cell that produces the protein in a nutrient-regulatable manner. In one embodiment, the mucosal cell is contacted with the polynucleotide in vivo. In another embodiment, the mucosal cell is contacted with the polynucleotide in vitro. In yet another embodiment, the mucosal cell contacted with the polynucleotide in vitro is suitable for transplantation into an animal. In additional embodiments, the mucosal cell is an endocrine cell (e.g., a K cell), or a non-endocrine cell. In still further embodiments, the mucosal cell is a stem cell or a pluripotent or multipotent progenitor cell.

In another embodiment, a nucleic acid expression construct used in the invention is designed to target production of proteins in gastrointestinal endocrine cells. The construct contains an expression control element operably linked to desired nucleic acid sequences. Expression control elements include promoters capable of targeting expression of a linked nucleic acid of interest to endocrine cells in the gut. Introduction of constructs into target cells can be carried out by conventional methods well known in the art (osmotic shock (e.g., calcium phosphate), electroporation, viral vectors, vesicles or lipid carriers (e.g., lipofection), direct microinjection, etc.).

Typically cell transformation employs a vector. The term "vector," refers to, e.g., a plasmid, virus, such as a viral vector, or other vehicle known in the art that can be manipulated by insertion or incorporation of a polynucleotide, for genetic manipulation (i.e., "cloning vectors"), or can be used to transcribe or translate the inserted polynucleotide (i. e., "expression vectors"). Such vectors are useful for introducing polynucleotides, including a nutrient-regulatable expression control element in operable linkage with a nucleic acid, and expressing the transcribed antisense or encoded protein in cells in vitro or in vivo.

A vector generally contains at least an origin of replication for propagation in a cell. Control elements, including expression control elements (e.g., nutrient-regulatable) as set forth herein, present within a vector, are included to facilitate transcription and translation. The term "control element" is intended to include, at a minimum, one or more components whose presence can influence expression, and can include components other than or in addition to promoters or enhancers, for example, leader sequences and fusion partner sequences, internal ribosome binding sites (IRES) elements for the creation of multigene, or polycistronic, messages, splicing signal for introns, maintenance of the correct reading frame of the gene to permit in-frame translation of mRNA, polyadenylation signal to provide proper polyadenylation of the transcript of a gene of interest, stop codons, among others.

Vectors can include a selection marker. As is known in the art, "selection marker" or equivalents means genes that allow the selection of cells containing the gene. "Positive selection" refers to a process whereby only the cells that contain the positive selection marker will survive upon exposure to the positive selection agent or be marked. For example, drug resistance is a common positive selection marker; cells containing the positive selection marker will survive in culture medium containing the selection drug, and those which do not contain the resistance gene will die.

Suitable drug resistance genes are neo, which confers resistance to G418, or hygr, which confers resistance to hygromycin, or puro which confers resistance to puromycin, among others. Other positive selection marker genes include genes that allow the sorting or screening of cells. These genes include genes for fluorescent proteins, the lacZ gene, the alkaline phosphatase gene, and surface markers such as CD8, among others.

Vectors included in the invention can contain negative selection markers. "Negative selection" refers to a process whereby cells containing a negative selection marker are killed upon exposure to an appropriate negative selection agent which kills cells containing the negative selection marker. For example, cells which contain the herpes simplex virus-thymidine kinase (HSV-tk) gene are sensitive to the drug gancyclovir (GANC). Similarly, the gpt gene renders cells sensitive to 6-thioxanthine.

Vectors included in the are those based on viral vectors, such as simian virus 40 (SV40) or bovine papilloma virus (BPV), which has the ability to replicate as extra-chromosomal elements (Eukaryotic Viral Vectors, Cold Spring Harbor Laboratory, Gluzman ed., 1982; Sarver et al., *Mol. Cell. Biol.* 1:486 (1981)). Viral vectors include retroviral, adeno-associated virus, adenovirus, reovirus, lentivirus, rotavirus genomes etc, modified for introducing and directing expression of a polynucleotide or transgene in mucosal cells (Cone et al., *Proc. Natl. Acad. Sci.* USA 81:6349 (1984)).

"Expression control elements" include polynucleotides, such as promoters and enhancers, that influence expression of an operably linked nucleic acid. Expression control elements and promoters include those active in a particular tissue or cell type, referred to herein as a "tissue-specific expression control elements/promoters." Tissue-specific expression control elements are typically active in specific cell or tissue because they are recognized by transcriptional activator proteins, or other regulators of transcription, that are unique to a specific cell or tissue type.

Figure 9:
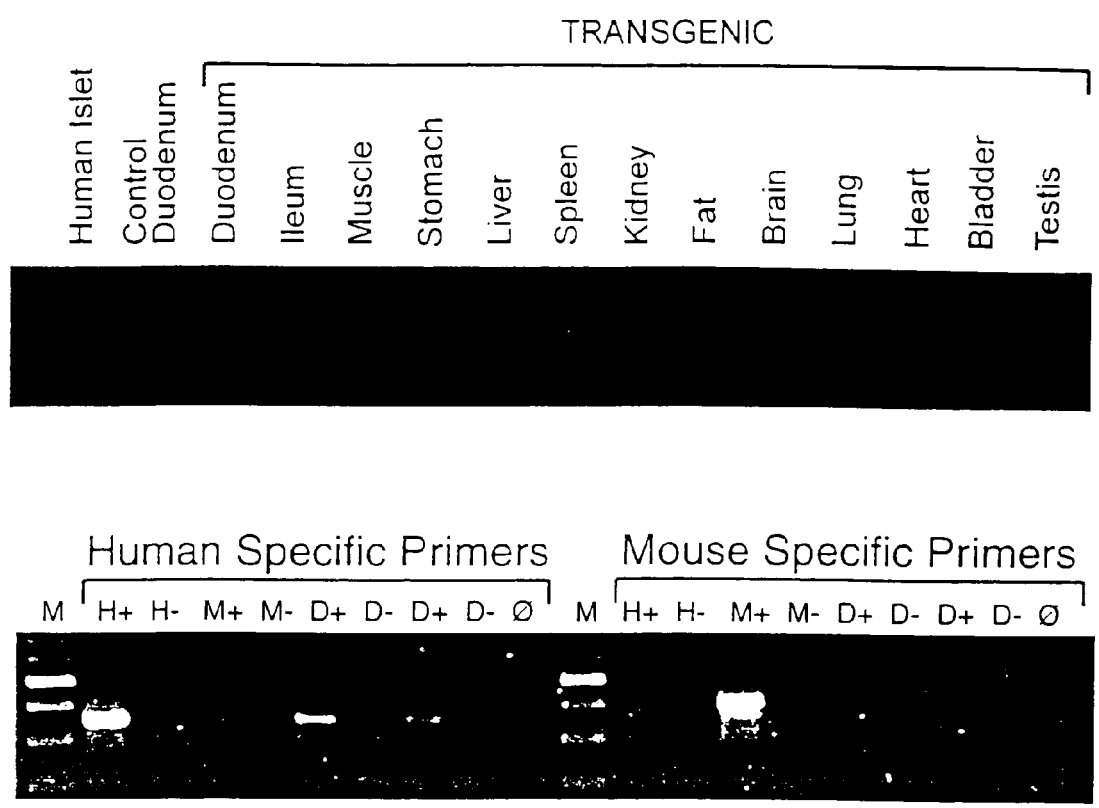
FIG. 9 shows targeted expression of human insulin to K cells in transgenic mice harboring the GIP/Ins construct. The upper panel shows a representative Northern blot analysis for human insulin gene expression in human islets, control duodenum (mouse) and transgenic mouse tissues. The lower panel shows RT-PCR analysis of cDNA from human islets (H), mouse islets (M) and duodenum samples (D) from two transgenic mice using human or mouse specific proinsulin primers. Samples were prepared in the presence (+) or absence (−) of reverse transcriptase. Ø indicates no DNA and M indicates markers.
Figure 10:
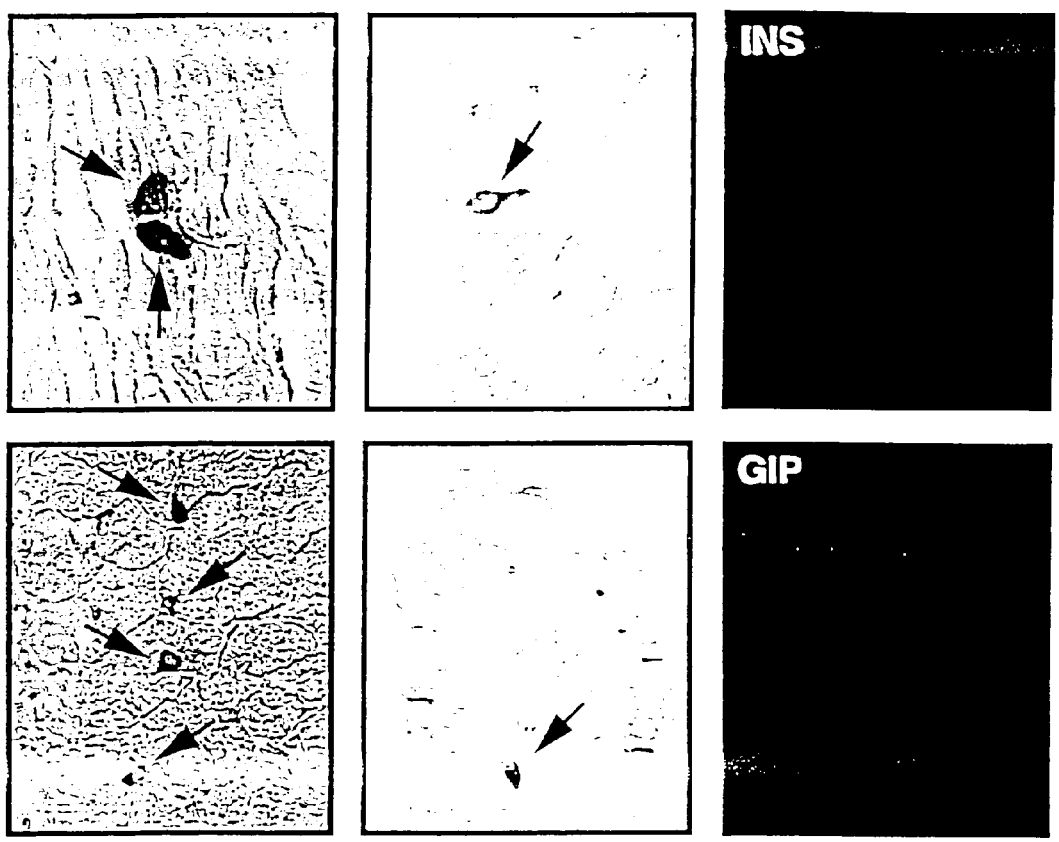
FIG. 10 shows the results of immunohistochemical staining for human insulin in sections of stomach (left panel) and duodenum (middle panel) from a transgenic mouse. Arrows indicate human insulin immunoreactive cells. The right panel shows duodenal sections from the same animal examined by immunofluorescence microscopy following co-staining with antisera specific for insulin (INS, green) and GIP (red).

A particular class of a tissue specific promoter is a "gut endocrine cell specific promoter," a promoter that drives expression of an operably linked nucleic acid in a gut endocrine cell. The GIP promoter is a specific example of a gut endocrine cell promoter. The GIP promoter includes multiple regulatory sequences which confer specific expression in the gastrointestinal tract (Tseng, C. C. et al. *Proc. Natl. Acad. Sci. USA* 90:1992 (1993); Yeng, C. M., et al *Mol. Cell. Endocrinol.* 154:161 (1999)). A GIP promoter sized about 2.5 Kb (−1 to ∼−2500 bp) in length targeted transgene expression to the stomach and duodenum (FIGS. 9 & 10). A shorter GIP promoter (−1 to ∼−1200 bp) conferred expression of transgene in the stomach but not duodenum and miss-targeted transgene expression to the pancreas (Yeng, C. M., et al. *Mol. Cell. Endocrinol.* 154:161 (1999)). The regulatory sequence between −1200 to −2500 bp therefore appears necessary for targeting transgene expression to GIP producing cells in the intestine.

Characterization of transcriptional elements in the GIP promoter revealed two TATA boxes (−27 to −23 and −115 to −111) and two CCAAT-like boxes (−158 to −154 and −170 to −167), potential AP-1 and AP-2 sites, cAMP response element (CRE), and a potential insulin response element (IRE) upstream of the putative transcription start site. Two putative GATA binding motifs also have been identified in the GIP promoter (-178 to −172 (proximal GATA); CAGATAC and −190 to −184 (distal GATA); CAGATAA) which conform to the consensus GATA binding motif sequence, (A/T)GATA(A/G). Specific mutations in the GIP promoter distal and proximal GATA motifs resulted in approximately 90% and 35% reduction in GIP promoter activity respectively, as assessed by luciferase reporter expression (Boylan et al, *J. Biol. Chem.* 273:17438 (1997)). However, a GIP promoter with both GATA motifs mutated behaved the same as the promoter with only the distal GATA motif altered. Thus, a GIP promoter containing one or more of the aforementioned nucleotide sequences or variants is an example of a subsequence that can retain glucose-regulatable or tissue specific (gut) expression of an operably linked nucleic acid. Such subsequences and variants can be used to confer glucose-regulatable or cell specific expression of an operably linked nucleic acid in vitro or in vivo.

An additional example of a tissue-specific control element is the promoter of the proglucagon gene. Similar to the GIP promoter, the proglucagon promoter has multiple control sequences that confer expression in either the gastrointestinal tract or brain and pancreas (Lee, Y. C., et al. *J Biol. Chem.* 267:10705 (1992); Gajic and Drucker, *Endocrinol.* 132:1055 (1993). A 1300 bp portion of the upstream rat proglucagon promoter sequence targeted expression of a transgene in the brain and pancreas, but not in the gastrointestinal tract (Efrat S., et. al. *Neuron* 1:605 (1988)). A longer proglucagon gene promoter (−1 to ~−2000 bp) directed transgene expression in the intestine, in addition to brain and pancreas (Lee, Y. C., et al. *J. Biol. Chem.* 267: 10705 (1992)). Thus, the portion conferring expression in gut appears to be within a 700 bp region of the promoter located between 1300 and 2000 bp upstream of the proglucagon gene.

Additional tissue-specific expression control elements that may be employed to target the expression of the nucleic acid of interest in gut endocrine cells are listed in Table 1. Many of these promoters are also nutrient-regulatable elements. For example, the GIP promoter includes multiple regulatory sequence which confer expression of an operably linked nucleic acid in response to nutrients.

This list is not intended to be exhaustive of all the possible expression control elements useful for driving gene expression in gut endocrine cells but merely to be exemplary.

Although tissue-specific expression control elements may be active in other tissue, for example, a gut specific expression control element may be active in a non-gut tissue, expression is significantly less than that in the gut tissue, (e.g., for non-gut tissue 6-10 fold less than in a gut tissue). Targeted delivery of a vector to gut tissue can limit the possibility of expression elsewhere in the body (e.g., in non-target tissues). Accordingly, tissue-specific elements included herein need not have absolute tissue specificity of expression.

TABLE 1

Exemplary Promoters and Enhancers for Targeting Expression of Proteins to Endocrine Cells in the Gut Glucokinase
Chromogranin A and B
Cholecystokinin
Glucose-dependent insulinotropic polypeptide
Proglucagon
Adenosine deaminase
Secretin
Gastrin
Somatostatin
Motilin
Ghrelin Additional expression control elements can confer expression in a manner that is regulatable, that is, a signal or stimuli increases or decreases expression of the operably linked nucleic acid. A regulatable element that increases expression of the operably linked nucleic acid in response to a signal or stimuli is also referred to as an "inducible element" (i.e., is induced by a signal, e.g., a nutrient). A regulatable element that decreases expression of the operably linked nucleic acid in response to a signal or stimuli is referred to as a "repressible element" (i.e., the signal decreases expression such that when the signal, is removed or absent, expression is increased). Typically, the amount of increase or decrease conferred by such elements is proportional to the amount of signal or stimuli present; the greater the amount of signal or stimuli, the greater the increase or decrease in expression.

A particular example of a regulatable expression control element is an element that increases or decreases expression of an operably linked nucleic acid in response to or withdrawal of a nutrient, in which case the element is referred to as a "nutrient-regulatable element." A nutrient inducible or repressible element generally provides basal levels of transcription (i.e., levels of expression in the absence of a stimuli or signal). Typically, basal levels of transcription are greater for a repressible element than for an inducible element.

As used herein, the term "nutrient" means any ingestible or consumable material such as that present in food or drink. As there are many, perhaps billions of different organic and inorganic substances present in food or drink, the term is used broadly herein. Particular examples of nutrients include sugars (e.g., glucose, lactose, sucrose, fructose, mannose, etc.), carbohydrates, starches, fats (saturated or unsaturated), lipids, fatty acids, triglycerides, polypeptides, amino acids, cellulose, hormones, vitamins, and minerals.

Nutrients may also modulate translation or stability of a protein. "Nutrient-regulatable" therefore includes situations where the nutrient modulates transcription, translation of the transcript into protein, or stability of the protein, thereby increasing or decreasing the amount of transcript or protein.

An expression control element can be "constitutive," such that transcription of the operably linked nucleic acid occurs without the presence of a signal or stimuli. Additionally, expression control elements also include elements that confer expression at a particular stage of the cell cycle or differentiation. Accordingly, the invention further includes expression control elements that confer constitutive, regulatable (e.g., nutrient-regulatable), tissue-specific, cell cycle specific, and differentiation stage specific expression.

Expression control elements include full-length sequences, such as native promoter and enhancer elements, as well as subsequences or polynucleotide variants which retain all or part of full-length or non-variant function (e.g., retain some amount of nutrient regulation or cell-specific expression). As used herein, the term "functional" and grammatical variants thereof, when used in reference to a nucleic acid or polypeptide sequence, subsequence or fragment, or nucleotide or amino acid sequence variant, means that the sequence has one or more functions of native nucleic acid or polypeptide sequence (e.g., non-variant or unmodified sequence). As used herein, the term "variant" means a sequence (nucleotide or amino acid) substitution (e.g., point mutation), deletion (internal or external) or addition (e.g., chimeric polypeptide), or other point mutation modification (e.g., chemical derivatives such as modified forms resistant to proteases or nucleases). Typically, amino acid variants have a few or several amino acid changes (e.g., 1 to 10, 10 to 20, 20 to 50) such as one or more conservative amino acid substitutions, or non-conservative amino acid substitutions outside of domains critical to a functionality that is desired to be retained in the variant (e.g., for insulin, glucose lowering function).

Expression control elements, such as nutrient-regulatable elements, also include functional variants, or subsequences. For example, a subsequence of a glucose-regulatable ~2.5 Kb GIP promoter (e.g., 2 Kb, 1 Kb, 0.5 Kb, 0.25 Kb, 0.20 Kb, 100 bp or less) can retain glucose-regulatable or tissue specific (gut or pancreas or brain) expression of an operably linked nucleic acid. Functional domains of various promoters having known properties can be configured to optimize amounts and patterns of expression of the operably linked nucleic acid.

Expression control elements included herein can be from bacteria, yeast, plant, or animal (mammalian or non-mammalian), so long as they function to confer expression control of an operably linked nucleic acid. Thus, any expression control element induced by a substance or stimuli (e.g., nutrient) from any organism can be used to modulate transcription of an operably linked nucleic acid in a mucosal cell and, as appropriate, translation of the encoded protein in response to the substance or stimuli, as set forth herein.

Nutrient-regulatable expression control elements exist, for example, as promoters that regulate expression of enzymes involved in glycolysis, lipid metabolism, carbohydrate metabolism and cholesterol (e.g., steroid) metabolism, which are modulated by sugars, fats, carbohydrate, and cholesterol, respectively, and are applicable in the invention. Particular examples of nutrient-regulatable control elements are glucose inducible elements that drive expression of L-pyruvate kinase, acetyl-CoA-carboxylase, spot-14, fatty acid synthase, glyceraldehyde phosphate dehydrogenase phospho-enol-pyruvate carboxykinase, glucose-6-phosphatase and phosphofructokinase (see, also, e.g., Rutter, GA et al., *News Physiol Sci*. 15:149 (2000)). Another example of a nutrient-regulatable control element is the alcohol-dehydrogenase gene regulatory element. Yet another example of a nutrient-regulatable control element is the vitamin-D response element, which confers expression in the presence of vitamin D. The mammalian metallothionein gene promoter is an expression control element inducible by metals. As with tissue-specific control elements, nutrient-regulatable control elements may be responsive to multiple nutrients. For example, a glucose-inducible element may also be responsive to lactose. A particular nutrient (e.g., glucose) is therefore not meant to be exclusive of other nutrients in that other nutrients may modulate activity (increase or decrease), to a lesser degree, of the control element.

An example of a bacterial nutrient-regulatable expression control element is the lac repressor, which is inducible by beta-galactosides. An example of a yeast nutrient-regulatable expression control element is the gal promoter present in GAL1 and GAL10 genes, which confer galactose-inducible expression. These elements can be operably linked to a nucleic acid and introduced into a mucosal cell in order to confer nutrient-regulatable production of the encoded protein.

Additional expression control elements included are those that are responsive to non-nutrients. Particular examples are chemicals or drugs that are orally active but not normally found in food. The non-nutrient drug or chemical, when consumed, stimulates expression of a nucleic acid operably linked to the non-nutrient expression control element. Ingesting specific amounts of the chemical or drug provides control of the amount of nucleic acid or protein produced (via transcription or secretion). For example, where a drug inducible expression control element confers expression of a nucleic acid encoding insulin, greater amounts of insulin can be produced in the gut by increasing the amount of drug consumed. Particular examples of such non-nutrient expression control systems can be found, for example, in U.S. Pat. Nos. 5,989,910; 5,935,934; 6,015,709; and 6,004,941.

As used herein, the term "operable linkage" or grammatical variations thereof refers to a physical or functional juxtaposition of the components so described as to permit them to function in their intended manner. In the example of an expression control element in operable linkage with a nucleic acid, the relationship is such that the control element modulates expression of the nucleic acid.

Expression control can be effected at the level of transcription, translation, splicing, message stability, etc. Typically, an expression control element that modulates transcription is juxtaposed near the 5' end of the transcribed nucleic acid (i.e., "upstream"). Expression control elements can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). Expression of the operably linked nucleic acid is at least in part controllable by the element (e.g., promoter) such that the element modulates transcription of the nucleic acid and, as appropriate, translation of the transcript. A specific example of an expression control element is a promoter, which is usually located 5' of the transcribed sequence. Another example of an expression control element is an enhancer, which can be located 5', 3' of the transcribed sequence, or within the transcribed sequence.

As used herein, the term "produces" or "production," when used in reference to a protein expressed by a mucosal cell or tissue, means either expression or secretion of the protein by a mucosal cell. Thus, where a mucosal cell produces a protein in response to a signal or stimuli, such as a nutrient, expression or secretion of the protein increases over the amount prior to the signal or stimuli. Production of a protein by the mucosal cell or tissue may be due to increased transcription of the nucleic acid, translation of the transcript, stability of the transcript or protein, or secretion of the encoded protein. Typically, secretion of a protein by a cell increased by a signal or stimuli (i.e. a secretagogue) stimulates release of a protein already translated in the cell. Proteins whose secretion is regulated are typically stored in secretory vesicles within endocrine cells.

Alternatively, transcription or translation of a nucleic acid encoding the protein, and subsequent secretion of the translated protein, may be increased by a signal or stimuli. Thus, in the example of a non-endocrine cell, a signal or stimuli (e.g., nutrient) may stimulate transcription of nucleic acid encoding the protein (e.g., insulin) via a nutrient-inducible expression control element, and the cell will subsequently secrete the encoded protein following its translation. In the example of an endocrine cell, such as a gut endocrine cell (e.g., K-cell, L-cell, etc.), the expression control element used to confer expression of the protein may or may not be regulatable but in either case a signal or stimuli typically will regulate secretion of the protein from the cell. In this case, the signal or stimuli functions as a secretagogue that stimulates or increases secretion of a protein. Therefore, in endocrine cells, whether expression is or is not nutrient regulatable (e.g., a constitutive promoter), protein production by the cell is nutrient regulatable because secretion of the protein is modulated by the nutrient. Accordingly, "nutrient-regulatable" also refers to nutrient modulating secretion of a protein from a cell.

Increased secretion of a protein by an endocrine cell in response to a signal or stimuli provides a more rapid response to the signal or stimuli in comparison to a protein produced by increasing transcription of a nucleic acid encoding the protein and subsequent secretion, as in a non-endocrine cell. In contrast, in a non-endocrine cell, a signal or stimuli such as a nutrient can increase transcription of a nucleic acid encoding a protein, and the translated protein is subsequently secreted by the cell without need for a signal or stimuli (e.g., nutrient). Thus, for a non-endocrine mucosal cell transformed with a nutrient-regulatable transgene, transcription of the transgene will be nutrient inducible, but secretion does not require the nutrient.

The nucleic acid can encode a therapeutic polypeptide, such as insulin, a glucagon antagonist, leptin, GLP-1 or cholecytoskinin. For example, a subsequence of full-length insulin that retains some ability to lower glucose, provide normal glucose homeostasis, or reduce the histopatholgical conditions associated with chronic or acute hyperglycemia in vivo is but one example of a functional subsequence that has one or more activities of its full length counterpart. Similarly, a subsequence or variant of leptin or CCK or a growth hormone, clotting factor or antibody that retains all or some of the ability to suppress appetite or induce weight stabilization or weight loss, stimulate growth, decrease clotting time or bleeding episodes, or provide passive protection against a foreign antigen (e.g., $H.$ $pylori$) are additional examples of a functional sequence or variant that can be expressed in mucosal tissue of an animal to provide therapeutic benefit.

Thus, "polypeptides," "proteins" and "peptides" encoded by the "nucleic acids," include full-length native sequences, as with naturally occurring proteins, as well as functional subsequences, modified forms or sequence variants so long as the subsequence, modified form or variant retains some degree of functionality of the native full-length protein.

As used herein, the term "transgene" means a polynucleotide that has been introduced into a cell or organism by artifice. For example, a mucosal cell having a transgene, the transgene has been introduced by genetic manipulation or "transformation" of the cell. A cell or progeny thereof into which the transgene has been introduced is referred to as a "transformed cell" or "transformant." Typically, the transgene is included in progeny of the transformant or becomes a part of the organism that develops from the cell. Transgenes may be inserted into the chromosomal DNA or maintained as a self-replicating plasmid, YAC, minichromosome, or the like.

Transgenes include any gene that is transcribed into an antisense or encodes a polypeptide. Particular polypeptides encoded by transgenes include detectable proteins, such as luciferase, β-galactosidase, green fluorescent protein (for non-invasive in vivo detection), chlorampenicolacetyltransferase, or proteins that are detectable (e.g., immunologically detectable). Detectable proteins are useful for assessing efficiency of cell transformation (e.g., in in vivo gene transfer), cell implantation success, as measured by cell survival or proliferation, for example (e.g., after implanting the transformed cell into animal mucosa).

Therapeutic proteins include insulin, a particular transgene useful to treat a hyperglycemic condition such as diabetes. Insulin is the primary hormonal modulator of glucose metabolism and facilitates transport of glucose from the blood to key metabolic organs such as muscle, liver and fat. As shown in Example III, insulin production in the gut of transgenic mice by an insulin transgene prevents diabetes in the mice. Insulin is produced in amounts sufficient to restore glucose tolerance and the timing of insulin release restores normal glucose homeostasis.

Another example of a transgene encoding a therapeutic protein to treat a hyperglycemic condition is a glucagon antagonist. Glucagon is a peptide hormone produced by α-cells in pancreatic islets and is a major regulator of glucose metabolism (Unger R. H. & Orci L. $N.$ $Eng.$ $J.$ $Med.$ 304:1518(1981); Unger R. H. Diabetes 25:136 (1976)). As with insulin, blood glucose concentration mediates glucagon secretion. However, in contrast to insulin glucagon is secreted in response to a decrease in blood glucose. Therefore, circulating concentrations of glucagon are highest during periods of fast and lowest during a meal. Glucagon levels increase to curtail insulin from promoting glucose storage and stimulate liver to release glucose into the blood. A specific example of a glucagon antagonist is [des-His$^1$, des-Phe$^6$, Glu$^9$]glucagon-NH$_2$. In streptozotocin diabetic rats, blood glucose levels were lowered by ~37% within 15 min of an intravenous bolus (0.75 μg/g body weight) of this glucagon antagonist (Van Tine B. A. et. al. $Endocrinology$ 137:3316 (1996)).

Another example of a transgene encoding a therapeutic protein to treat a hyperglycemic condition or undesirable body mass (e.g., obesity) is glucagon-like peptide-1 (GLP-1). GLP-1 is a hormone released from L-cells in the intestine during a meal which stimulates pancreatic β-cells to increase insulin secretion. GLP-1 has additional activities which make it an attractive therapeutic agent for treating obesity and diabetes. For example, GLP-1 reduces gastric emptying, suppresses appetite, reduces glucagon concentration, increases β-cell mass, stimulates insulin biosynthesis and secretion in a glucose-dependent fashion, and likely increases tissue sensitivity to insulin (Kieffer T. J., Habener J. F. $Endocrin.$ $Rev.$ 20:876 (2000)). Therefore, regulated release of GLP-1 in the gut to coincide with a meal can provide therapeutic benefit for a hyperglycemic condition or an undesirable body mass.

GLP-1 analogs that are resistant to dipeptidyl peptidase IV (DPP IV) provide longer duration of action and improved therapeutic value. Thus, transgenes encoding GLP-1 analogs with increased duration of action can be tageted to gut using the invention described herein to provide nutrient regulated production of GLP-1 analogs for treating a hyperglycemic condition or an undesirable body weight.

Another example of a transgene encoding a therapeutic protein to treat a hyperglycemic condition is an antagonist to the hormone resistin. Resistin is an adipocyte-derived factor for which expression is elevated in diet-induced and genetic forms of obesity. Neutralization of circulating resistin improves blood glucose and insulin action in obese mice. Conversely, administration of resistin in normal mice impairs glucose tolerance and insulin action (Steppan CM et. al. *Nature* 409:307 (2001)). Production of a protein that antagonizes the biological effects of resistin in gut can therefore provide an effective therapy for obesity-linked insulin resistance and hyperglycemic conditions.

Yet another example of a transgene encoding a therapeutic protein to treat undesirable body mass (e.g., obesity) or a hyperglycemic condition is leptin. Leptin, although produced primarily by fat cells, is also produced in smaller amounts in a meal-dependent fashion in the stomach. Leptin relays information about fat cell metabolism and body weight to the appetite centers in the brain where it signals reduced food intake (promotes satiety) and increases the body's energy expenditure. A single daily subcutaneous injection of leptin had only a modest effect on weight reduction in humans yet leptin treatment results in profound decreases of fat mass in rodents as well as reduction in blood glucose (Seufert J. et. al. *Proc Natl Acad Sci USA*. 96:674 (1999). Previous studies have shown that leptin is rapidly degraded in the circulation. Thus, delivery from gut in a regulated fashion will likely enhance the clinical benefit of leptin reducing food intake and body mass, as well as blood glucose.

Yet another example of a transgene encoding a therapeutic protein to treat undesirable body weight (e.g. obesity) or a hyperglycemic condition is the C-terminal globular head domain of adipocyte complement-related protein (Acrp30). Acrp30 is a protein produced by differentiated adipocytes. Administration of a proteolytic cleavage product of Acrp30 consisting of the globular head domain to mice leads to significant weight loss (Fruebis J. et al. *Proc. NatL Acad. Sci USA* 98:2005 (2001)). Therefore, targeted expression of a transgene encoding the globular domain of Acrp30 to gut can promote weight loss.

Still another example of a transgene encoding a therapeutic protein to treat undesirable body mass (e.g., obesity) is cholecystokinin (CCK). CCK is a gastrointestinal peptide secreted from the intestine in response to particular nutrients in the gut. CCK release is proportional to the quantity of food consumed and is believed to signal the brain to terminate a meal (Schwartz M. W. et. al. *Nature* 404:661-71 (2000)). Consequently, elevated CCK can reduce meal size and promote weight loss or weight stabilization (i.e., prevent or inhibit increases in weight gain). A nutrient-regulated CCK delivery system can therefore provide therapeutic benefit for the purpose of reducing food intake in persons.

Additional examples of transgenes encoding therapeutic proteins include clotting factors, to treat hemophilia and other coagulation/clotting disorders (e.g., Factor VIII, IX or X); growth factors (e.g., growth hormone, insulin-like growth factor-1, platelet-derived growth factor, epidermal growth factor, acidic and basic fibroblast growth factors, transforming growth factor-β, etc.), to treat growth disorders or wasting syndromes; and antibodies (e.g., human or humanized), to provide passive immunization or protection of a subject against foreign antigens or pathogens (e.g., H. Pylori), or to provide treatment of cancer, arthritis or cardiovascular disease.

Additional transgenes encoding a therapeutic protein include cytokines, interferons (e.g., interferon (INF), INF-α2b and 2a, INF-αN1, INF-β1b, INF-gamma), interleukins (e.g., IL-1 to IL-10), tumor necrosis factor (TNF-α TNF-β), chemokines, granulocyte macrophage colony stimulating factor (GM-CSF), polypeptide hormones, antimicrobial polypeptides (e.g., antibacterial, antifungal, antiviral, and/or antiparasitic polypeptides), enzymes (e.g., adenosine deaminase), gonadotrophins, chemotactins, lipid-binding proteins, filgastim (Neupogen), hemoglobin, erythropoietin, insulinotropin, imiglucerase, sarbramostim, tissue plasminogen activator (tPA), urokinase, streptokinase, neurite growth factor (NGF) phenylalanine ammonia lyase, brain-derived neurite factor (BDNF), neurite growth factor (NGF), phenylalanine ammonia lyase, thrombopoietin (TPO), superoxide dismutase (SOD), adenosine deamidase, catalase calcitonin, endothelian, L-asparaginase pepsin, uricase trypsin, chymotrypsin elastase, carboxypeptidase lactase, sucrase intrinsic factor, calcitonin parathyroid hormone(PTH)-like, hormone, soluble CD4, and antibodies and/or antigen-binding fragments (e.g, FAbs) thereof (e.g., orthoclone OKT-e (anti-CD3), GPIIb/IIa monoclonal antibody).

The transgenes described herein are particular applications of the invention but are not intended to limit it. In this regard, the skilled artisan could readily envision additional transgenes transcribed into therapeutic antisense or encode therapeutic polypeptides.

Target cells include mucosal cells or cells not normally present in the mucosum that can or have been adapted for growth in mucosum. As used herein, the terms "mucosa" or "mucosal," when used in reference to a cell, means a cell that can grow in mucosa. Mucosal cells include, for example, those cells which are normally found in animal mucosa, such as a cell of the gut (e.g., mouth (tongue and buccal tissue), esophagus, and stomach, small and large intestine, rectum, anus), the respiratory tract, the lungs and nasopharynx and other oral cavities (e.g., vagina). Thus, a mucosal cell refers to the various cell types that normally reside in the aforementioned regions including stem cells or other multipotent or pluripotent cells that differentiate into the various mucosal cell types. Particular examples of mucosal cells include endocrine cells, such as K cells, L-cells, S-cells, G-cells, D-cells, I-cells, Mo-cells, Gr-cells and entero-endocrine cells. Endocrine cells are generally characterized by their ability to secrete a synthesized protein into the blood in response to a signal or stimuli (a "secretagogue"). Non-endocrine mucosal cells include epithelial cells which line the outer surface of most mucosal tissue, mucous cells, villus cells, columnar cells, stromal cells and Paneth cells. Non-endocrine cells are generally not known to secrete a synthesized protein into the blood in response to a signal or stimuli.

The finding that gut K cells can function as surrogate cells for producing appropriately regulated physiologic levels of insulin in animals indicates a mode of therapy for diabetes, freeing subjects from insulin injections and reducing or even eliminating the associated debilitating complications. As there are possibly billions of K cells are present in the human gut (Sandström O., El-Salhy M., *Mech. Ageing Dev.* 108:39 (1999)), regulated insulin secretion from a fraction of these cells may be sufficient to achieve therapeutic benefit, including ameliorating symptoms and complications associated with diabetes.

The gut is the largest endocrine organ in the body capable of producing vast quantities of proteins and contains rapidly renewing tissue in which the dividing cells are accessible. Target cells, such as K cells and stem cells, are predominantly located in the upper gut which is readily accessible to non-invasive gene therapy techniques. Thus, non-invasive techniques like oral formulations, endoscopic procedures, or a modified feeding tube allow the deployment of vectors that facilitate integration of the transgene into the host genome.

Vectors have already been developed that deliver genes to cells of the intestinal tract, including the stem cells (Croyle et al., Gene Ther. 5:645 (1998); S. J. Henning, Adv. Drug Deliv. Rev. 17:341 (1997), U.S. Pat. Nos. 5,821,235 and 6,110,456). Many of these vectors have been approved for human studies. Therefore, gut cells, such as K cells, that secrete a protein, such as insulin, leptin, glucagon antagonist, GLP-1, GLP-2, Ghrelin, cholecystokinin, growth hormone, clotting factors, antibody, among others, in a regulatable fashion is a means with which to treat diabetes, obesity, growth deficiency and other disorders treatable by producing a protein in mucosal tissue.

A partial list of several types of gut endocrine cells, proteins secreted by the cells in response to particular nutrients ("secretagogues") and exemplary functions are shown in Table 2. The proteins, endocrine cells and nutrients are all applicable in the invention.

TABLE 2

| PEPTIDE | CELL TYPE | CELL LOCATION | FUNCTION | SECRET- AGOGUES |
|---|---|---|---|---|
| Gastrin | G-cells | Gastric Antrum (stomach) | increase acid secretion | Amino acids |
| Somatostatin | D-cells | GI Tract | reduce gut peptide release (paracrine inhibitor) | Intra-luminal acid, free fatty acids, hormones |
| Glucose-depenent Insulinotropic Polypeptide | K cells | Upper small intestine | Pancreatic bicarbonate secretion reduce gastric acid release | Acid, bile salts, fatty acids |
| Glucagon-like peptide-1 | L-cells | Lower small intestine | Increase insulin secretion, decrease gastric acid release | Glucose, fat |
| Glucagon-like peptide-2 | L-cells | Lower small intestine | increase mucosal proliferation | Glucose, fat |
| Cholecystokinin | I-cells | Upper small | increase gall bladder contraction & pancreatic enzyme secretion | Amino acids, fatty acids |
| Motilin | Mo-cells | Upper small intestine | Increase Gastric motility | Cyclic release, meals |
| Ghrelin | Gr-cells | Stomach and intestine | orexigenic | yet to be elucidated |

As used herein, the term "cultured," when used in reference to a cell, means that the cell is grown in vitro. A particular example of such a cell is a cell isolated from a subject, and grown or adapted for growth in tissue culture. Another example is a cell genetically manipulated in vitro, and transplanted back into the same or a different subject. The term "isolated," when used in reference to a cell, means a cell that is separated from its naturally occurring in vivo environment. An example of an isolated cell would be a mucosal cell obtained from a subject such as a human. "Cultured" and "isolated" cells may be manipulated by the hand of man, such as genetically transformed. These terms include any progeny of the cells, including progeny cells that may not be identical to the parental cell due to mutations that occur during cell division. The terms do not include an entire human being.

The target mucosal cell may be present in a mucosal tissue or organ of a subject, such as that of the gut (e.g., intestine). Thus, one way in which to introduce the protein in the subjects' mucosum to achieve therapy is to intracellularly deliver a polynucleotide, including an expression control element, in operable linkage with a nucleic acid encoding the protein into cells present in the mucosum of the subject. Alternatively, the mucosal cell can be isolated from an appropriate tissue of a subject, transfected with the transgene and introduced (transplanted) into a tissue (mucosal or other) of a subject. Thus, another way in which to introduce the protein into the subject to achieve therapy is to transfect a polynucleotide, including an expression control element, in operable linkage with a nucleic acid encoding the protein into cultured mucosal cells, followed by implanting the transformed cells or progeny into the subject.

Mucosal cells transfected with a transgene include endocrine and non-endoccrine cell lines that grow in-culture. For example, a transformed cell of gut origin or lineage, such as an STC-1 or GTC-1 cell, can be implanted into a tissue of a subject. Mucosal cells transfected with a transgene, in vitro, ex vivo or in vivo include endocrine cells (e.g., K-cell, L-cell, G-cell, D-cell, S-cell, I-cell or Mo-cell, Gr-cell) and non-endocrine epithelial, columnar, stromal, villus, Panth, stem cells or other cell types typically present in mucosal tissue of an animal.

The target cell may also be a non-mucosal cell (endocrine or non-endocrine) which can grow or adapted for growth in mucosum or other tissue (even for a limited time, e.g. days or months). For example, a cell may be obtained from a non-mucosal tissue of a subject, transformed with a transgene or polynucleotide, and then transplanted into a tissue of subject (the same or different subject) in order to effect treatment when the transcribed antisense or encoded protein is produced. Alternatively, a primary cell isolate or an established non-mucosal cell line can be transformed with a transgene or polynucleotide, and then transplanted into a mucosal tissue of a subject.

Thus, to produce an isolated or cultured mucosal cell of the invention, the mucosal cell may be obtained from a tissue or organ of the gastrointestinal tract of a subject, for example. The mucosal cell can then be transfected with the transgene by conventional nucleic acid techniques and propagated. For example, intestinal stem cells can be isolated and then cultured and transfected in vitro (Booth, C. et al., Exp. Cell Res. 241:359 (1999); Kawaguchi, A. L. et al., J. Pediatr. Surg. 33:559 (1998)). Cells that contain or express the transgene can be identified using conventional methods, such as Southern, Northern or Western blots, alone or in combination with selection using a selectable marker. Transformed cells can then be re-introduced (transplanted/ implanted) into the same or a different tissue of the same or a different subject from which they were originally obtained.

If desired, target mucosal endocrine cells may contain multiple transgenes (i.e., two or more). In this way, expression of different proteins encoded by the transgenes can provide an additive or synergistic effect and, in turn, a therapeutic benefit greater than expression of either protein alone. In addition, if the two transgenes are linked to different expression control elements, or secretion of the two encoded polypeptides are regulated by different signals or stimuli (e.g., two different nutrients), the proteins can be produced either independently of each other or in combination (when both of the different nutrients are provided). For example, two transgenes, one encoding GLP-1 and the other encoding insulin, can be constructed in which production is controlled by two different signals, such as glucose and a drug, respectively. Glucose stimulates production of GLP-1 (either by stimulating transcription or secretion, as discussed herein) whereas the drug stimulates production of insulin (either by stimulating transcription or secretion, as discussed herein). Addition of the drug to stimulate production of insulin (again, either by stimulating transcription or secretion) and addition of glucose can stimulate production of GLP-1; increased amounts of drug or glucose could induce even greater amounts of insulin or GLP-1 production. Production of both insulin and GLP-1 by addition of the drug with a meal (containing glucose) may provide an even greater therapeutic benefit, especially for subjects suffering from severe diabetes, for example. Accordingly, the invention further includes mucosal cells containing multiple transgenes and methods of producing and using them.

Thus, in accordance with the invention, there are provided mucosal cell(s) that produces a protein regulatable by a nutrient, where expression of the protein is conferred by a transgene comprising an expression control element in operable linkage with a nucleic acid encoding the protein. In one embodiment, the mucosal cell is an endocrine cell (e.g., a K-cell). In another embodiment, the mucosal cell is a non-endocrine cell. In yet another embodiment, the mucosal cell is a stem cell, or a multipotent or pluripotent progenitor cell. In an additional embodiment, the expression control element confers nutrient-regulatable expression. In one aspect, the nutrient-regulatable element comprises a gut endocrine promoter (e.g., a GIP promoter). In still another embodiment, the nutrient increases secretion of a protein encoded by the nucleic acid. In yet another embodiment, the nucleic acid encodes a therapeutic polypeptide (e.g., insulin, leptin, glucagon-like peptide-1, glucagon-like peptide-2, a glucagon antagonist, cholecystokinin, a growth hormone, a clotting factor, an antibody, among others). In yet another embodiment, the mucosal cell includes two or more transgenes.

The polynucleotides, including an expression control element, in operable linkage with a nucleic acid, can be introduced for stable expression into cells of a whole organism. Such organisms including transgenic animals, are useful for studying the effect of mucosal protein production in a whole animal and therapeutic benefit. For example, as described herein, production of insulin in the gut of a transgenic mouse protects the animal from developing diabetes and from glucose intolerance after destruction of pancreatic β-cells. Mice strains that develop or are susceptible to developing a particular disease (e.g., diabetes, degenerative disorders, cancer, etc.) are also useful for introducing therapeutic proteins as described herein in order to study the effect of therapeutic protein expression in the disease susceptible mouse. Transgenic and genetic animal models that are susceptible to particular disease or physiological conditions are known in the art and are appropriate targets for expressing therapeutic proteins in gut.

Thus, in accordance with the invention, there are provided non-human transgenic animals that produce a protein in mucosal tissue, production not naturally occurring in mucosal tissue of the animal, production conferred by a transgene present in somatic or germ cells of the animal. In one embodiment, the transgene comprises a polynucleotide, including an expression control element in operable linkage with a nucleic acid encoding a therapeutic polypeptide (e.g., insulin, leptin, GLP-1, GLP-2, Ghrelin, CCK, glucagon antagonist, growth hormone, clotting factor, antibody, among others.) In another embodiment, the transgenic animal is a mouse. In yet another embodiment, expression of the therapeutic polypeptide in the mucosal tissue of the animal is responsive to a nutrient. In still another embodiment, secretion of therapeutic polypeptide in mucosal tissue is increased by a nutrient. In a further embodiment, expression of the therapeutic polypeptide in mucosal tissue is increased by a nutrient (i.e., the expression control element controlling expression of insulin comprises a nutrient-inducible element). In an additional embodiment, the nutrient-regulatable element comprises a glucose-inducible promoter (e.g., a glucose-dependent insulinotropic polypeptide promoter). In additional embodiments, the mucosal tissue is a tissue or organ of the gastrointestinal tract (e.g., intestine) or gut, and includes endocrine cells. In a further embodiment, isolated cells of the invention transgenic animals that express the therapeutic polypeptide are provided.

The term "transgenic animal" refers to an animal whose somatic or germ line cells bear genetic information received, directly or indirectly, by deliberate genetic manipulation at the subcellular level, such as by microinjection or infection with recombinant virus. The term "transgenic" further includes cells or tissues (i.e., "transgenic cell," "transgenic tissue") obtained from a transgenic animal genetically manipulated as described herein. In the present context, a "transgenic animal" does not encompass animals produced by classical crossbreeding or in vitro fertilization, but rather denotes animals in which one or more cells receive a nucleic acid molecule. Invention transgenic animals can be either heterozygous or homozygous with respect to the transgene. Methods for producing transgenic animals, including mice, sheep, pigs and frogs, are well known in the art (see, e.g., U.S. Pat. Nos. 5,721,367, 5,695,977, 5,650,298, and 5,614,396) and, as such, are additionally included.

In accordance with the invention, there are provided methods of treating a subject having, or at risk of having, a disorder treatable by producing a therapeutic protein in a mucosal tissue. In one embodiment, a method of the invention includes contacting mucosal tissue cells in the subject transformed with a polynucleotide (in vitro, ex vivo or in vivo) comprising an expression control element in operable linkage with a nucleic acid encoding the therapeutic protein with a nutrient that induces production of the protein in an amount effective to treat the disorder. In another embodiment, a method of the invention includes producing a therapeutic protein in a mucosal tissue of the subject by implanting one or more transformed mucosal cells (in vitro or ex vivo) that produce the protein into the subject's tissue in an amount effective for treating the disorder.

Disorders treatable by a method of the invention include a hyperglycemic condition, such as insulin-dependent (type 1) or -independent (type 2) diabetes, as well as physiological conditions or disorders associated with or that result from the hyperglycemic condition. Thus, hyperglycemic conditions treatable by a method of the invention also include a histopathological change associated with chronic or acute hyperglycemia (e.g., diabetes). Particular examples include degeneration of pancreas (β-cell destruction), kidney tubule calcification, degeneration of liver, eye damage (diabetic retinopathy), diabetic foot, ulcerations in mucosa such as mouth and gums, excess bleeding, delayed blood coagulation or wound healing and increased risk of coronary heart disease, stroke, peripheral vascular disease, dyslipidemia, hypertension and obesity.

Thus, in various methods of the invention, a mucosal cell that produces insulin or a functional subsequence of insulin in response to glucose, is useful for increasing insulin, decreasing glucose, improving glucose tolerance, treating a hyperglycemic condition (e.g., diabetes) or for treating a physiological disorders associated with or resulting from a hyperglycemic condition. Such disorders include, for example, diabetic neuropathy (autonomic), nephropathy (kidney damage), skin infections and other cutaneous disorders, slow or delayed healing of injuries or wounds (e.g., that lead to diabetic carbuncles), eye damage (retinopathy, cataracts) which can lead to blindness, diabetic foot and accelerated periodontitis. Such disorders also include increased risk of developing coronary heart disease, stroke, peripheral vascular disease, dyslipidemia, hypertension and obesity.

As used herein, the term "hyperglycemic" or "hyperglycemia," when used in reference to a condition of a subject, means a transient or chronic abnormally high level of glucose present in the blood of a subject. The condition can be caused by a delay in glucose metabolization or absorption such that the subject exhibits glucose intolerance or a state of elevated glucose not typically found in normal subjects (e.g., in glucose-intolerant subdiabetic subjects at risk of developing diabetes, or in diabetic subjects). Fasting plasma glucose (FPG) levels for normoglycemia are less than about 110 mg/dl, for impaired glucose metabolism, between about 110 and 126 mg/dl, and for diabetics greater than about 126 mg/dl.

Disorders treatable by producing a protein in a mucosal tissue also include obesity or an undesirable body mass. Leptin, cholecystokinin and GLP-1 decrease hunger, increase energy expenditure, induce weight loss or provide normal glucose homeostasis. Thus, in various embodiments, a method of the invention for treating obesity or an undesirable body mass, or hyperglycemia, includes contacting mucosal tissue cells having a transgene encoding leptin, cholecystokinin or GLP-1 with a nutrient so as to produce the protein in an amount effective to treat obesity or an undesirable body mass. Disorders treatable also include those typically associated with obesity, for example, abnormally elevated serum/plasma LDL, VLDL, triglycerides, cholesterol, plaque formation leading to narrowing or blockage of blood vessels, increased risk of hypertension/stroke, coronary heart disease, etc.

As used herein, the term "obese" or "obesity" refers to a subject having at least a 30% increase in body mass in comparison to an age and gender matched normal subject. "Undesirable body mass" refers to subjects having 1%-29% greater body mass than a matched normal subject as well as subjects that are normal with respect to body mass but who wish to decrease or prevent an increase in their body mass.

The term "subject" refers to an animal. Typically, the animal is a mammal, however, any animal having mucosal tissue, such as gut, is encompassed by the term. Particular examples of mammals are primates (humans), dogs, cats, horses, cows, pigs, and sheep. Subjects include those having a disorder, e.g., a hyperglycemic disorder, such as diabetes, or subjects that do not have a disorder but may be at risk of developing the disorder, e.g., subdiabetic subjects having FPG levels between about 110 and 126 mg/dl. Subjects at risk of developing a disorder include, for example, those whose diet may contribute to or be associated with development of diabetes or obesity, as well as those which may have a family history or genetic predisposition towards development of diabetes or obesity. Subjects also include apparently normal subjects, for example, those who wish to lose weight but are not considered to be obese or have greater than normal body mass.

A partial list of therapeutic proteins and target diseases is shown in Table 3.

TABLE 3

| LEAD COMPOUNDS | TARGET DISEASE | FUNCTION | THERAPEUTIC EFFECT |
|---|---|---|---|
| Insulin | Diabetes | Insulin replacement | Improve glucose tolerance Delay/prevent diabetes |
| Glucagon antagonists | Diabetes | Reduce endogenous glucose production | Improve glucose tolerance |
| GLP-1 | Diabetes Obesity | Stimulate growth of β-cells, improve insulin sensitivity, suppress appetite | Improve glucose tolerance Induce weight loss |
| Leptin | Obesity Diabetes | Appetite suppression and improvement of insulin sensitivity | Induce weight loss Improve glucose tolerance |
| CCK | Obesity | Appetite suppression | Induce weight loss |
| Growth hormone (GH) | GH deficiencies, wasting and anti-aging | GH replacement | Improve growth |
| Clotting factors | Hemophilia | Clotting factors replacement | Improve clotting time |
| Therapeutic human monoclonal antibodies | Infections Cancers | Pathogen neutralization or immune modulations | Prevent infections or transplant rejections |

Treatment generally results in reducing or preventing the severity or symptoms of the condition in the subject, i.e., an improvement in the subject's condition or a "therapeutic effect." Therefore, treatment can reduce the severity or prevent one or more symptoms of the condition or an associated disorder, inhibit progression or worsening of the condition or an associated disorder, and in some instances, reverse the condition or an associated disorder. Thus, in the case of a hyperglycemic condition, for example, treatment can reduce blood glucose, improve glucose tolerance, provide normal glucose homeostasis, or prevent, improve, or reverse a histopathological change associated with or that results from the hyperglycemic condition.

Improvement of a histopathological change associated with a hyperglycemic condition includes, for example, preventing further or reducing kidney tubule calcification, decreasing or arresting retinopathy or cataracts, decreasing wound or injury healing time, reducing diabetic foot, preventing or reducing accelerated periodontitis, or decreasing the risk of developing coronary heart disease, stroke, peripheral vascular disease, dyslipidemia, hypertension and obesity. Improvement in obesity can include, for example, a reduction of body mass or an improvement in an associated disorder, such as a decrease in cholesterol, LDL or VLDL levels, a decrease in blood pressure, a decrease in intimal thickening of the blood vessel associated with high fat diet, a decrease in resting heart rate, an increase in lung capacity, etc. Improvement in a bleeding disorder, such as hemophilia can induce, for example, decreased clotting time or frequency/duration of bleeding episodes.

As used herein, the term "ameliorate" means an improvement in the subject's condition, a reduction in the severity of the condition, or an inhibition of progression or worsening of the condition. In the case of a hyperglycemic condition (e.g., diabetes), for example, an improvement can be a decrease in blood glucose, an increase in insulin, an improvement in glucose tolerance, or glucose homeostasis.

An improvement in a hyperglycemic condition also can include improved pancreatic function (e.g., inhibit or prevent β-islet cell destruction), a decrease in a pathology associated with or resulting from the condition, such as an improvement in histopathology of an affected tissue or organ, as set forth herein. In the case of obesity, for example, an improvement can be a decrease in weight gain, a reduction of body mass or an improvement in a conditions associated with obesity, as set forth herein (e.g., reduction of blood glucose, cholesterol, LDL or VLDL levels, a decrease in blood pressure, a decrease in intimal thickening of the blood vessel, etc.). In the case of hemophilia or other blood coagulation/clotting/bleeding disorders, an improvement can reduce the frequency or duration of bleeding episodes or hemorrhage. Improvements likewise include chronic disorders associated with blood coagulation/clotting/bleeding associated disorders such as a reduction in neurological problems, crippling tissue and joint damage, for example.

The doses or "effective amount" for treating a subject are preferably sufficient to ameliorate one, several or all of the symptoms of the condition, to a measurable or detectable extent, although preventing or inhibiting a progression or worsening of the disorder or condition, or a symptom, is a satisfactory outcome. Thus, in the case of a condition or disorder treatable by producing a protein in a mucosal tissue, the amount of protein produced, or transplanted cell(s) sufficient to ameliorate a condition treatable by a method of the invention will depend on the condition and the desired outcome and can be readily ascertained by the skilled artisan. Appropriate amounts will depend upon the condition treated, the therapeutic effect desired, as well as the individual subject (e.g., the bioavailability within the subject, gender, age, etc.). For example, a partial restoration of normal glucose homeostatsis in a subject can reduce the frequency for insulin injection, even though complete freedom from insulin injection has not resulted.

The effective amount can be ascertained by measuring relevant physiological effects. For example, in the case of diabetes or other hyperglycemic condition, a decrease in blood glucose or an improvement in glucose tolerance test can be used to determine whether the amount of insulin, or cell(s) expressing insulin transplanted into the animal mucosa, is effective to treat the hyperglycemic condition. For example, an amount reducing FPG from 126 mg/dl to 120, 115, 110, or less is an effective amount. In the case of obesity or an undesirable body mass, a decrease in the subjects' mass, a decrease in meal size or caloric content of a meal, increased satiety for a given meal size, and decreases in serum/plasma levels of lipid, cholesterol, fatty acids, LDL or VLDL all can be effective amounts for ameliorating obesity or an undesirable body mass of a subject. In the case of hemophilia, an effective amount is an amount which reduces clotting time or frequency or duration of bleeding episodes in a subject.

The methods of the invention for treating a subject are applicable for prophylaxis to prevent a condition in a subject, such as a hyperglycemic condition or an associated disorder, or development of obesity or an increased body mass. Alternatively, the methods can be practiced following treatment of a subject as described herein. For example, following treatment and a reduction of body mass to the desired weight, leptin, GLP-1 or CCK can be periodically produced by mucosal cells, as described herein, in order to suppress appetite, decrease meal consumption, etc. thereby maintaining desired body weight.

The methods of the invention for treating a subject also can be supplemented with other forms of therapy. Supplementary therapies include drug treatment, a change in diet (low sugar, fats, etc.) surgical resection, transplantation, radiotherapy, etc. For example, a method of the invention for treating a hyperglycemic condition can be used in combination with drugs or other pharmaceutical formulations that increase insulin or lower glucose in a subject. Drugs for treating diabetes include, for example, biguanides and sulphonylureas (e.g., tolbutamide, chlorpropamide, acetohexamide, tolazamide, glibenclamide and glipizide). Appetite suppression drugs are also well known and can be used in combination with the methods of the invention. Supplementary therapies can be administered prior to, contemporaneously with or following the invention methods of treatment. The skilled artisan can readily ascertain therapies that may be used in a regimen in combination with the treatment methods of the invention.

As a method of the invention can include in vivo delivery, such as a polynucleotide comprising an expression control element in operable linkage with a nucleic acid into mucosal cells of a subject, in order to produce an encoded protein in the subject, for example, expression systems further include vectors specifically designed for in vivo delivery. Vectors that efficiently deliver genes to cells of the intestinal tract (e.g., stem cells) have been developed and are contemplated for use in delivering the polynucleotides into mucosal cells (see, e.g., U.S. Pat. Nos. 5,821,235, 5,786,340 and 6,110, 456; Croyle, M. A. et al., *Gene Ther*. 5:645 (1998); Croyle, M. A. et al., *Pharm. Res*. 15:1348 (1998); Croyle, M. A. et al., *Hum. Gene Ther*. 9:561 (1998); Foreman, P. K. et al., *Hum. Gene Ther*. 9:1313 (1998); Wirtz, S. et al., *Gut* 44:800 (1999)). Adenoviral and adeno-associated viral vectors suitable for gene therapy are described in U.S. Pat. Nos. 5,700,470, 5,731,172 and 5,604,090. Additional vectors suitable for gene therapy include herpes simplex virus vectors (see, e.g., U.S. Pat. No. 5,501,979), retroviral vectors (see, e.g., U.S. Pat. Nos. 5,624,820, 5,693,508 and 5,674,703; and WO92/05266 and WO92/14829), bovine papilloma virus (BPV) vectors (see, e.g., U.S. Pat. No. 5,719,054), CMV-based vectors (see, e.g., U.S. Pat. No. 5,561,063) and parvovirus, rotavirus and Norwalk virus vectors. Lentiviral vectors are useful for infecting dividing as well as non-dividing cells (see, e.g., U.S. Pat. No. 6,013,516).

Introduction of nucleic acid and polypeptide in vitro, ex vivo and in vivo can also be accomplished using other techniques. For example, a polynucleotide comprising an expression control element in operable linkage with a nucleic acid encoding a protein can be incorporated into particles or a polymeric substance, such as polyesters, polyamine acids, hydrogel, polyvinyl pyrrolidone, ethylene-vinylacetate, methylcellulose, carboxymethylcellulose, protamine sulfate, or lactide/glycolide copolymers, polylactide/glycolide copolymers, or ethylenevinylacetate copolymers. A polynucleotide can be entrapped in microcapsules prepared by coacervation techniques or by interfacial polymerization, for example, by the use of hydroxymethylcellulose or gelatin-micro capsules, or poly (methylmethacrolate) micro capsules, respectively, or in a colloid drug delivery system. Colloidal dispersion systems include macromolecule complexes, nano-capsules, microspheres, beads, and lipid-based systems, including oil-in-water emulsions, micelles, mixed micelles, and liposomes. The use of liposomes for introducing various compositions, including polynucleotides, is known to those skilled in the art (see, e.g., U.S. Pat. Nos. 4,844,904, 5,000,959, 4,863,740, and 4,975, 282). A carrier comprising a natural polymer, or a derivative or a hydrolysate of a natural polymer, described in WO 94/20078 and U.S. Pat. No. 6,096,291, is suitable for mucosal delivery of molecules, such as polypeptides and polynucleotides. Piperazine based amphilic cationic lipids useful for gene therapy also are known (see, e.g., U.S. Pat. No. 5,861,397). Cationic lipid systems also are known (see, e.g., U.S. Pat. No. 5,459,127). Accordingly, vector (viral and non-viral, e.g., naked DNA) and non-vector means of delivery into mucosal cells or tissue, in vitro, in vivo and ex vivo can be achieved and are contemplated.

As the methods of the invention can include contacting a mucosal cell(s) present in a subject with a polynucleotide, the present invention also provides "pharmaceutically acceptable" or "physiologically acceptable" formulations in which a transgene or therapeutic polypeptide are included. Such formulations can be administered ex vivo or in vivo to a subject in order to practice the treatment methods of the invention, for example.

As used herein, the terms "pharmaceutically acceptable" and "physiologically acceptable" refer to carriers, diluents, excipients and the like that can be administered to a subject, preferably without producing excessive adverse side-effects (e.g., nausea, abdominal pain, headaches, etc.). Such preparations for administration include sterile aqueous or non-aqueous solutions, suspensions, and emulsions.

Pharmaceutical formulations can be made from carriers, diluents, excipients, solvents, dispersion media, coatings, antibacterial and antifungal agents, isotonic and absorption delaying agents, and the like, compatible with administration to a subject. Such formulations can be contained in a tablet (coated or uncoated), capsule (hard or soft), microbead, emulsion, powder, granule, crystal, suspension, syrup or elixir. Supplementary active compounds and preservatives, among other additives, may also be present, for example, antimicrobials, anti-oxidants, chelating agents, and inert gases and the like.

A pharmaceutical formulation can be formulated to be compatible with its intended route of administration. Thus, pharmaceutical formulations include carriers, diluents, or excipients suitable for administration by routes including intraperitoneal, intradermal, subcutaneous, oral (e.g., ingestion or inhalation), intravenous, intracavity, intracranial, transdernal (topical), parenteral, e.g. transmucosal and rectal.

Solutions or suspensions used for parenteral, intradermal, or subcutaneous application can include the following: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical formulations suitable for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (for example, glycerol, propylene glycol, and liquid polyethylene glycol, and the like), and suitable mixtures thereof. Fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can be included in the composition. Prolonged absorption of injectable formulations can be achieved by including an agent that delays absorption, for example, aluminum monostearate or gelatin.

For oral administration, a composition can be incorporated with excipients and used in the form of tablets, troches, or capsules, e.g., gelatin capsules. Pharmaceutically compatible binding agents, and/or adjuvant materials can be included in oral formulations. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or flavoring.

Formulations can also include carriers to protect the composition against rapid degradation or elimination from the body, such as a controlled release formulation, including implants and microencapsulated delivery systems. For example, a time delay material such as glyceryl monostearate or glyceryl stearate alone, or in combination with a wax, may be employed.

Additional formulations include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. Methods for preparation of such formulations will be apparent to those skilled in the art. The materials can also be obtained commercially from Alza Corporation and Nova Pharmaceuticals, Inc., for example.

The rate of release of a composition can be controlled by altering the concentration or composition of such macromolecules. For example, the composition can be entrapped in microcapsules prepared by coacervation techniques or by interfacial polymerization, for example, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems including oil-in-water emulsions, micelles, mixed micelles, and liposomes. These can be prepared according to methods known to those skilled in the art, for example, as described in U.S. Pat. No. 4,522,811.

Additional pharmaceutical formulations appropriate for administration are known in the art and are applicable in the methods and compositions of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; and *Pharmaceutical Principles of Solid Dosage Forms*, Technonic Publishing Co., Inc., Lancaster, Pa., (1993)).

The mucous or endothelial lining of the mucosal tissue may be removed or otherwise prepared prior to administration, for example, using penetrants or other barrier penetration enhancers. Such penetrants appropriate to the barrier to be permeated are generally known in the art, and include, for example, for transmucosal administration, incubation with N-acetyl-cysteine (Nakanishi et al. *Chem Pharm Bull* (Tokyo) 40:1252 (1992), Meaney and O'Driscoll *Eur J Pharm Sci*. 8:167 (1999); hydrolysis of intestinal mucins by purified Sigma 1 protein and infectious subviral particles (Bisaillon et al. *J Mol Biol*. 286:759(1999); desialation (Slomiany et al. *Gen Pharmacol*. 27:761 (1996); (Hirmo et al. *FEMS Immunol Med Microbiol*. 20:275 (1998); desulphation by H. pylori glycosulfatase (Slomiany et al. *Am J GastroenteroL* 87:1132 (1992); desialation by neuraminidase (Hanski et al. *Cancer Res*. 51:5342 (1991)); disulphide bond breakage by β-mercaptoethanol (Gwozdzinski et al. *Biochem Int*. 17:907 (1988); deglycosylation with specific exoglycosidases such as fucosidase, β-galactosidase, N-acetyl-galactosaminidase, β-N-acetyl hexososaminidase, and neuraminidase (Slomiany et al. *Biochem Biophys Res Commun*. 142:783 (1987); acid removal of by 0.4 N HCl (Ruggieri et al. *Urol Res*. 12:199 (1984), Davis C. P. and Avots-Avotins A. E. Scan Electron Microsc. (Pt 2):825-30 (1982), Parsons et. al. *Am J Pathol*. 93:423 (1978)), among others. Mucosal administration can also be accomplished through the use of nasal sprays or suppositories. For administration by inhalation, the formulation can be delivered via a pump or an aerosol spray from a dispenser or pressured container that contains a suitable propellant, e.g., a gas such as carbon dioxide, or a nebulizer.

The number of stem cells can be increased by exposure to cytotoxic agents and growth factors. For example, irradiation of the small gut increases the number clonogenic/stem cells (Roberts S. A. *Radiat. Res*. 141:303 (1995); Cai W. B. et. al. *Intl. J. Radiat. Biol*. 71:145 (1997)). In addition, treatment with GLP-2, epidermal growth factor, TGF-α, insulin-like growth factors, interleukins, among others, have been shown to promote the growth of mucosal cells (Potten C. S. Int. J. Exp. Path 78:219 (1997)). In this way, additional target cells can be produced thereby increasing transformation efficiency and subsequent regulated protein production by transformed cells.

Endoscopes, cannulas, intubation tubes, catheters and the like can be used to deliver the formulation to various parts of the gut of a subject. This allows effective delivery and targeting of vectors to particular areas of the gut.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All publications, patents and other references cited herein are incorporated by reference in their entirety. In case of conflict, the present specification, including definitions, will control.

As used herein, the singular forms "a", "and," and "the" include plural referents unless the context clearly indicates otherwise. Thus, for example, reference to "a mucosal cell" includes a plurality of such cells and reference to "a polynucleotide comprising an expression control element in operable linkage with a nucleic acid" includes reference to one or more such constructs, and so forth.

A number of embodiments of the invention have been described. Nevertheless, it will be understood that various modifications may be made without departing from the spirit and scope of the invention. Accordingly, the following examples are intended to illustrate but not limit the scope of invention described in the claims.

Example I

This example describes the establishment of a gut endocrine cell line useful for studying regulated insulin production and for targeting insulin expression in vivo. This example also describes construction of a human insulin gene expression vector.

A GIP-expressing cell line was established to investigate whether the GIP promoter is effective in targeting insulin gene expression to K cells. This cell line was cloned from the murine intestinal cell line STC-1, a mixed population of gut endocrine cells (Rindi et. al., *Am. J Pathol*. 136:1349 (1990)). K cells in the mixed population were visually identified by transfection of a green fluorescent protein expression plasmid driven by ~2.5 Kb of the rat GIP promoter. The rat GIP promoter was obtained from a rat genomic λDASH library (Stratagene) by plaque hybridization with the rat GIP cDNA clone as described previously (Boylan et. al., *J. Biol. Chem*. 273:17438 (1997)) and subcloned into the promoterless pEGFP-1 plasmid (Clontech). The resulting reporter vector was transfected into STC-1 cells (D. Drucker, University of Toronto) using Lipofectamine (GIBCO). Cells were dispersed with Trypsin/EDTA and fluorescent cells expressing EGFP were double hand-picked and placed into individual dishes for clonal expansion (FIG. 1).

Figure 2:
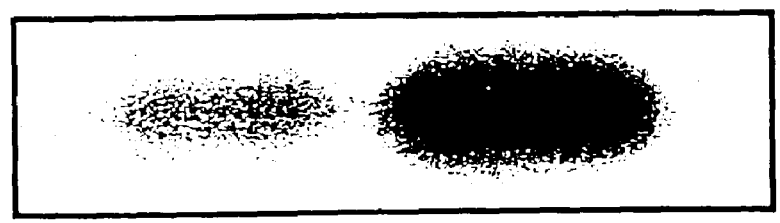
FIG. 2 is a representative Northern blot analysis of GIP mRNA in STC-1 and GTC-1 cells showing that GTC-1 is a highly enriched population of GIP-producing K cells.

Following clonal expansion of the transiently fluorescent cells, clones were analyzed for the expression of GIP MRNA by northern blotting. In brief, total RNA from GTC-1 and STC-1 cells was isolated with Trizol (Gibco) according to manufacturer's instructions. Total cell RNA (20 ug) from each sample was electrophoretically separated and transferred to nylon membrane. Hybridization was performed with radiolabeled 660 bp EcoR1 fragment of the rat GIP cDNA that was random-primed with [α-$^{32}$P]dCTP. Following hybridization, membranes were washed and exposed to x-ray film. The level of GIP mRNA in one clone (GIP Tumor Cells; GTC-1) was ~8-fold higher than in the parental heterogeneous STC-1 cells (FIG. 2).

In order to determine if GTC-1 cells correctly process human genomic preproinsulin, an insulin expression construct in which the insulin gene linked to the 3' end of the rat GIP promoter (FIG. 3, GIP/Ins) was transfected into these cells.

Figure 3:
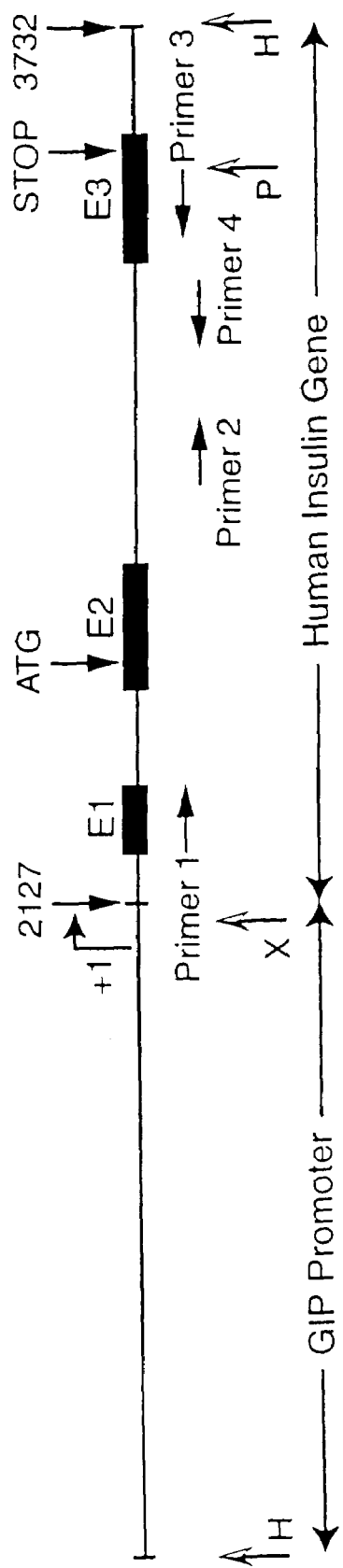
FIG. 3 is a schematic view of the GIP/Ins plasmid construct used for targeting human insulin expression to K cells. It contains the genomic sequence of the human insulin gene operably linked to the GIP promoter (~2.5 kb of 5'-regulatory sequence of the GIP gene The three exons are denoted by filled boxes (E1, 2 and 3). The positions of primers used for RT-PCR detection of proinsulin mRNA are indicated. Hind III (H), Pvu II (P) and Xho I (X) sites are shown. Positions of start (ATG) and stop codons are indicated.

To construct the human insulin/GIP expression plasmid, a ~2.5 Kb portion of the rat GIP promoter was inserted into pGLBH as discussed above (Boylan et al., *J. Biol. Chem*. 273:17438 (1997)). Human insulin cDNA, which comprises ~1.6 Kb of the genomic sequence extending from nucleotides 2127 to 3732 including the native polyadenylation site, was excised from pBR322 (ATCC No. 57399) by digestion with BamHI and ligated into the BglII site of the GIP containing pGLBH construct. The expression construct is shown in FIG. 3.

Figure 4:
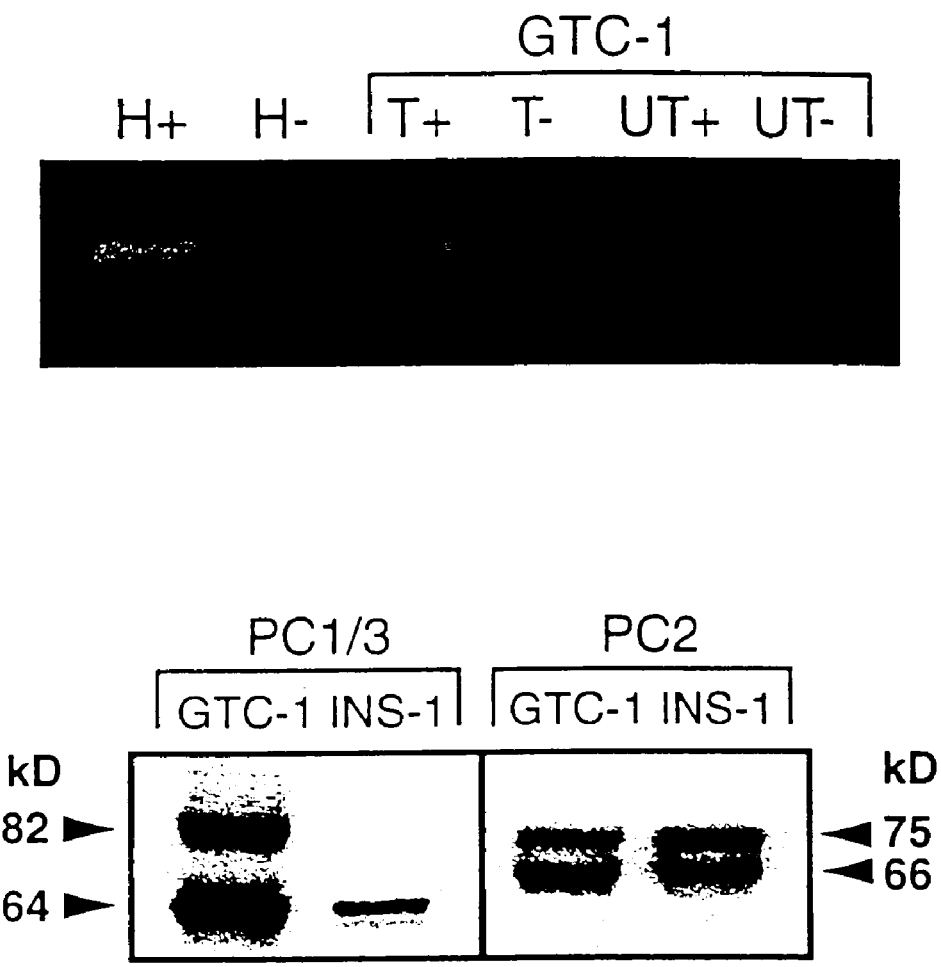
FIG. 4 shows expression of human insulin and proinsulin processing enzymes in tumor-derived K cells. The upper panel shows RT-PCR analysis of cDNA from human islets (H) and GTC-1 cells either transfected (T) or untransfected (UT) with GIP/Ins plasmid. Samples were prepared with (+) or without (−) reverse transcriptase. The lower panel shows immunoblot analysis of proprotein convertases PC1/3 and PC2 expression in GTC-1 cells and a β-cell line (INS-1). Arrows indicate predicted product size for PC 1/3 isoforms (64 and 82 kD) and PC2 isoforms (66 and 75 1D).

Total RNA was isolated from GIP/Ins-transfected and non-transfected cells and human islets (Trizol, GIBCO). Five μg of the RNA isolated was reversed transcribed with oligo-dT primer using superscript II reverse transcriptase (GIBCO). Two μl of the cDNA product was amplified with human preproinsulin gene-specific primers (Primer 1 and 3, FIG. 3). The results indicate that human preproinsulin mRNA transcript was correctly processed (FIG. 4, Top).

When the GIP/Ins construct was transfected into a β-cell (INS-1), liver (HepG2) and rat fibroblast (3T3-L1) cell line, little human preproinsulin mRNA was detectable. These observations indicate that the GIP promoter is cell specific and is likely to be effective in targeting transgene expression to K cells in vivo.

Western blot analysis of GTC-1 cells to determine if processing enzymes for converting proinsulin to mature insulin were present was then performed. In brief, GTC-1 cells were lysed in ice-cold RIPA buffer and supernatants were assayed for total protein content using the Bradford method. Cell lysate protein (50 μg) was fractionated on 10% SDS-PAGE and fractionated proteins were electroblotted onto nitrocellulose membranes and incubated with polyclonal antibodies recognizing PC1/3 and PC2 (Dr. Iris Lindberg, Louisiana State Medical Center). Membranes were washed, incubated with goat anti-rabbit antisera coupled to horseradish peroxidase (Amersham-Pharmacia) and developed with a chemilurninescence western blotting detection kit. The results indicate that the proprotein convertases required for correct processing of proinsulin to mature insulin (PC1/3 and PC2; Steiner, D. F., *Curr. Opin. Chem. Biol.* 2:31 (1998)) were expressed in GTC-1 cells (FIG. 4, Bottom).

Figure 5:
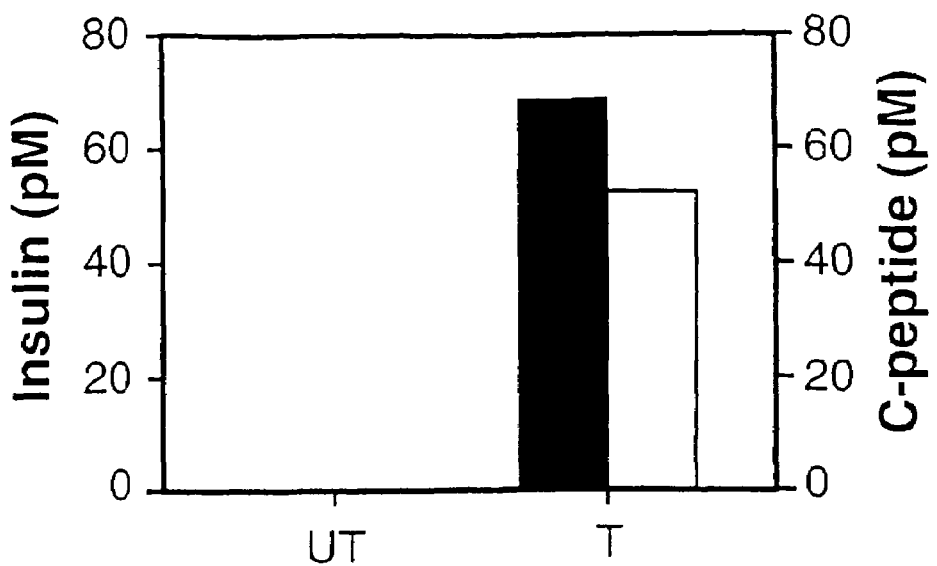
FIG. 5 shows the levels of human insulin and C-peptide detected in culture media from GTC-1 cells transfected (T) or untransfected (UT) with the GIP/Ins construct. Insulin and C-peptide are indicated by open and solid bars respectively.

To confirm that proinsulin was appropriately processed, insulin and C-peptide levels in the cell culture media were measured (FIG. 5). Both C-peptide and insulin were detected in culture media collected from GTC-1 cell transfected with the GIP/Ins plasmid. This result indicates that K cells are process proinsulin to mature insulin.

Figure 6:
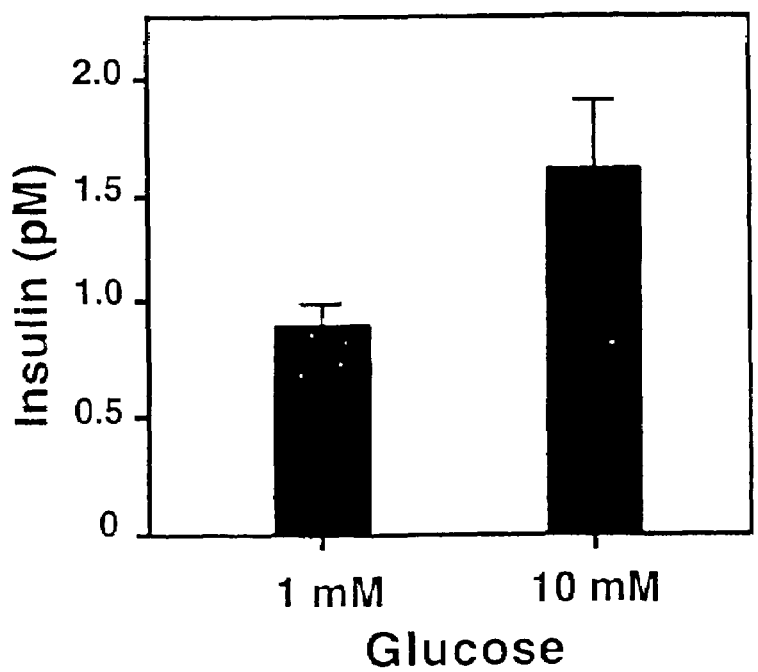
FIG. 6 is a graph showing the stimulatory effect of glucose on insulin secretion from GTC-1 cells stably transfected with the GIP/Ins plasmid.
Figure 7:
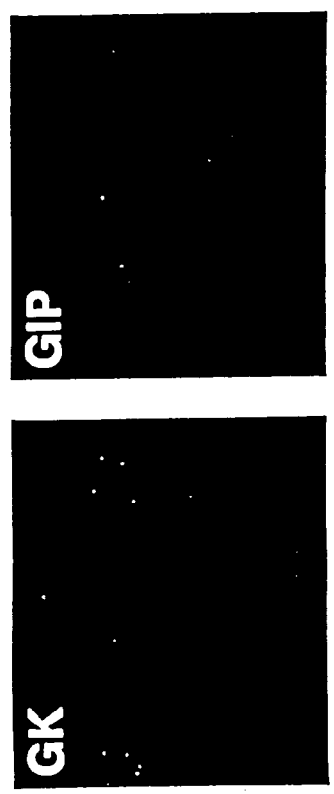
FIG. 7 shows co-expression of glucokinase (GK, red) and GIP (green) in mouse duodenal sections.

To confirm that production of human insulin from GTC-1 cells transfected with the GIP/Ins plasmid was glucose regulatable, insulin levels in the cell culture media under different concentrations of glucose were assayed. In brief, 70-80% confluent GTC-1 cells in 12-well plates were fasted 2 hr in DMEM with 1.0 mM glucose and 1% Fetal calf serum (FCS). Cells were washed and then incubated in 0.5 mL of release media (DMEM plus 1% FCS with either 1.0 or 10.0 mM of glucose) for 2 hr. Medium was collected after 2 hours for each condition and assayed using the human-specific insulin ELISA kit according to the supplier's instructions (ALPCO). Furthermore, release of insulin from these cells was glucose-dependent (FIG. 6).

Example II

This example describes transgenic mice that produce insulin in response to glucose.

Figure 8:
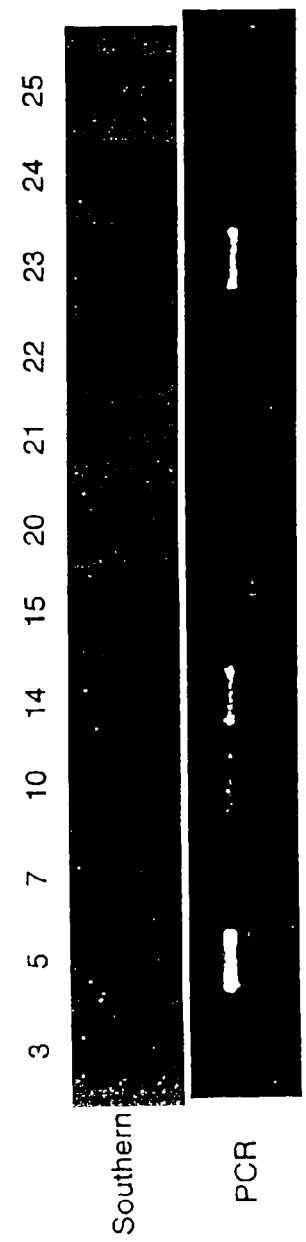
FIG. 8 shows genomic Southern blot and PCR identification of transgenic founder lines. Mouse numbers are indicated at the top.

Using the human insulin expression construct GIP/Ins described in Example I, the GIP/insulin fragment (~4.1 Kb) was removed by digestion with HindIII. Transgenic mice were generated by pronuclear microinjection of the ~4.1 Kb transgene into fertilized embryos that were implanted into pseudopregnant females. Transgenic offspring were identified by Southern blot analysis. DNA from ear sections was digested with XhoI and PvuII (FIG. 3), electrophoretically separated, and transferred to nylon membrane. For the detection of the transgene, a 416 bp human insulin gene fragment encompassing intron 2 was amplified using primers 2 and 4 (FIG. 3). The PCR product was prepared as a probe by random labeling with [α-$^{32}$P] dCTP, and bands were detected by autoradiography. Southern analysis results were further confirmed by PCR amplification of the genomic DNA using primers 2 and 4. Positive founders were outbred with wild-type FVB/N mice to establish transgenic lines (FIG. 8).

Transgenic mice tissues were examined for insulin expression. In brief, total RNA (50 μg) for each mouse stomach and duodenum, ileum, muscle, liver, spleen, kidney, fat, brain, lung, heart, bladder and testes were fractionated, transferred to a membrane and probed with a 333 base pair cDNA fragment encompassing exons 1 and 2 and part of exon 3 of human preproinsulin gene. The analysis revealed that insulin was expressed in the stomach and duodenum, but not in ileum, muscle, liver, spleen, kidney fat, brain, lung, heart, bladder or testes from the resulting transgenic animals (FIG. 9).

To confirm insulin production in duodenum, RT-PCT analysis for insulin mRNA was performed. In brief, human proinsulin specfic, forward 5' CCAGCCGCAGC-CTTTGTGA-3' (SEQ. ID. NO. 1) and reverse 5'-GGTA-CAGCATTGTTCCACAATG-3' (SEQ. ID. NO. 2); mouse proinsulin specific, forward 5'-ACCACCAGCCCTAAGT-GAT-3' (SEQ. ID. NO. 3) and reverse 5'-CTAGTTGCAG-TAGTTCTCCAGC-3' (SEQ. ID. NO.4) primer were used. PCR conditions were as follows: denaturation at 94° C. for 1 min, annealing at 50° C. for 1 min and extension at 72° C. for 1 min for 45 cycles. PCR products were analyzed on a 2% agarose gel and visualized by ethidium bromide staining. The human- and mouse- specific primer sets yielded 350 bp and 396 bp products, respectively.

Insulin RNA was detected in the duodenum sample from the transgenic mice confirming that insulin was not due to contamination from adjacent mouse pancreas (FIG. 9). Cellular localization of insulin protein was determined in tissue biopsies from transgenic mice utilizing antibody to insulin. Insulin immunoreactivity was detected in distinct endocrine cells in sections from stomach of transgenic animals (FIG. 10).

The aforementioned results indicate that tissue distribution of insulin expression in transgenic animals corresponds to the tissue expression pattern of GIP (Tseng et al., *Proc. Natl. Acad. Sci. USA* 90:1992 (1993); Yeung et al., *Mol. Cell. Endocrinol.* 154:161 (1999)).

To determine whether the cells that expressed insulin were K cells, tissues were analyzed for immune-reactivity with GIP antisera. In brief, tissues were fixed in Bouin's solution overnight and embedded in paraffin. Tissue sections (5 μm thick) were mounted on glass slides. For immunohistochemistry, the avidin-biotin complex method was used with peroxidase and diaminobenzidine as the chromogen. Sections were incubated with guinea pig anti-insulin (1:500; Linco Research, Inc.) or mouse anti-GIP (1:200; R. Pederson, University of British Columbia) for 30 min and appropriate secondary antibodies for 20 min at room temperature. Biotinylated secondary antibodies were used for immunohistochemistry, and fluorescein- or Cy3-conjugated secondary antibodies were used for immunofluorescence. The results indicate that insulin-expressing cells were K cells due to co-expression of immunoreactive GIP (FIG. 10). These results confirm that human insulin production was effectively targeted to K cells in the gut of mice.

Example III

This example shows that insulin production in transgenic mice provided normal glucose homeostasis and protection from developing diabetes. Production of human insulin from gut K cells of transgenic mice is also meal regulated. This example also describes data showing that glucose inducible insulin production by the transgenic mice provides glucose homeostasis after destruction of pancreatic β cells.

Analysis of plasma human insulin levels in transgenic mice in response to food intake was performed. In brief, plasma insulin levels were measured using the human-specific insulin ELISA kit (ALPCO) according to supplier's instructions. This assay has <0.01% cross-reactivity with human proinsulin and C-peptide and does not detect mouse insulin. Plasma C-peptide measurements were made with a rat/mouse C-peptide RIA kit (Linco). The assay displays no cross-reactivity with human C-peptide.

In pooled plasma samples collected after oral glucose challenge, insulin was 39.0±9.8 pM (n=10, Mean±SEM) in transgenic and undetectable in controls (n=5). To confirm that human insulin produced from K cells is meal regulated, transgenic mice were fasted. Following a 40 hour fast, blood samples were collected via the tail vein. Animals were then refed with a standard chow and blood samples were collected again 24 hr after food replacement.

Figure 11A:
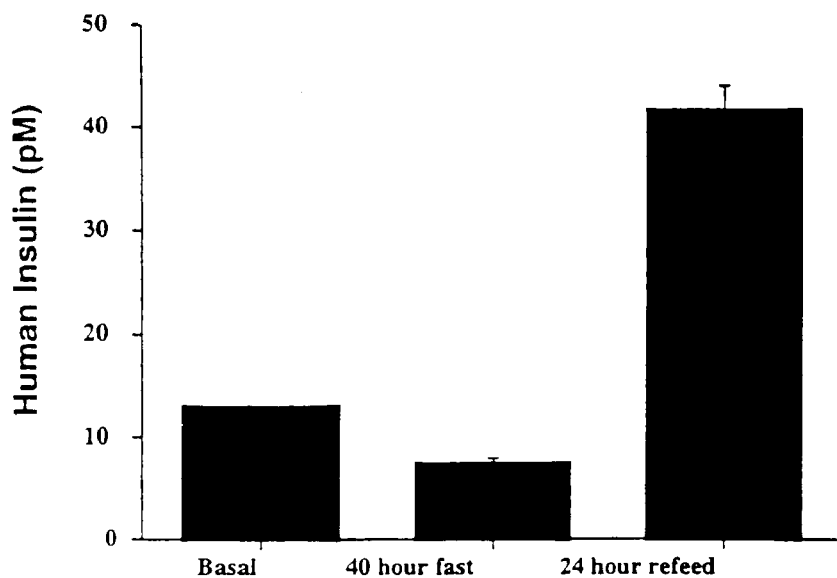
FIG. 11A is a graph showing that the production of human insulin from gut K cells of transgenic mice is meal-regulated.

As shown in FIG. 11A, fasting significantly reduced the circulating human insulin in transgenic mice by more 40% (13.0±4.2 pM vs 7.6±2.3 pM, p<0.03). After food restriction, refeeding resulted in over 400% increase in circulating human insulin.

Figure 11B:
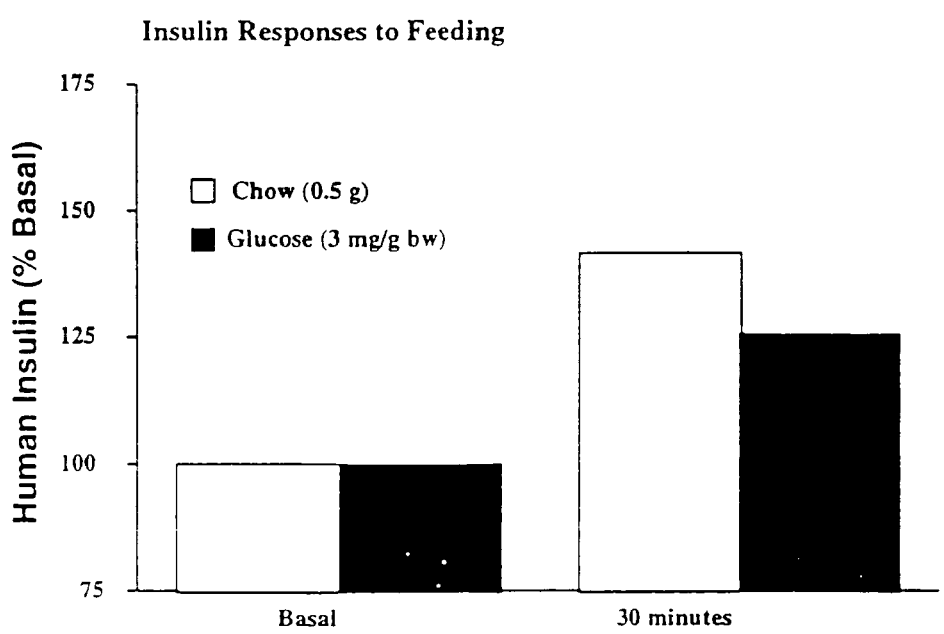
FIG. 11B is a graph showing the release kinetics of human insulin from gut K cells of transgenic mice in response to a mixed meal test and oral glucose challenge.

To evaluate the release kinetics of human insulin from gut K cells, fasted transgenic mice were fed either a mixed meal in the form of a chow pellet (0.5 g) or an oral glucose challenge (3 mg/g body weight). As shown in FIG. 11B, both oral nutrient challenges promptly stimulated the release of human insulin from gut K cells by at least 20% within 30 min. These results confirmed that insulin secretion from gut K cells is indeed meal-regulated.

Interestingly, levels of mouse C-peptide after an oral glucose load in transgenics were ~30% lower than controls (227.1±31.5 pM vs 361.5±31.2 pM, n=3 in each group, mean±SEM). This observation suggests that human insulin produced from the gut may have led to compensatory down-regulation of endogenous insulin production.

The ability of human insulin production from gut K cells to protect transgenic mice from diabetes was investigated. Streptozotocin (STZ), a β-cell toxin, was administered to transgenic mice and age-matched controls. In brief, Streptozotocin (200 mg/kg body weight) in citrate buffer was administered to 8 week old transgenic and age-matched control mice via an intraperitoneal injection. At this dose of streptozotocin, mice typically display glucosuria within 3 days post injection.

In control animals, STZ treatment resulted in fasting hyperglycemia (26.2±1.52 mM, n=3, mean±SEM) and the presence of glucose in the urine within 3 to 4 days, indicating the development of diabetes. When left untreated these animals deteriorated rapidly and died within 7 to 10 days. In contrast, neither glucosuria nor fasting hyperglycemia (9.52±0.67 mM, n=5, mean±SEM) was detected in transgenic mice for up to three months after STZ treatment and they continued to gain weight normally.

To determine if insulin production from K cells was able to maintain oral glucose tolerance in these mice despite the severe β-cell damage by STZ, mice were challenged with an oral glucose load five days after STZ treatment. In brief, glucose was administered orally by feeding tube (1.5 g/kg body weight) as a 40% solution (wt/vol) to mice fasted for 14 hr. Blood samples (40 μl) were collected from the tail vein of conscious mice at 0, 10, 20, 30, 60, 90, and 120 minutes following the glucose load. Plasma glucose levels were determined by enzymatic, colorimetric assay (Sigma) and plasma insulin levels were measured using human-specific insulin ELISA kit (ALPCO).

Figure 12:
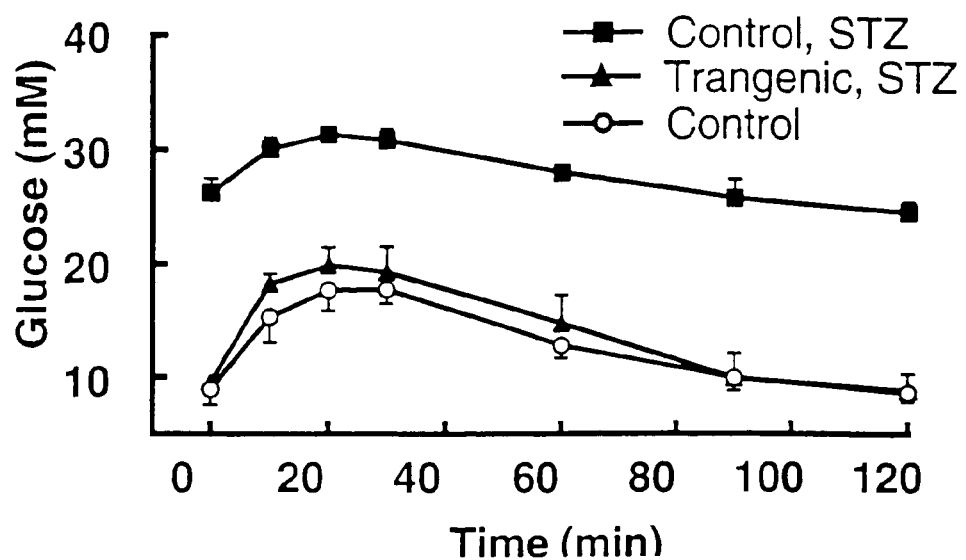
FIG. 12 is a graph showing the changes of blood glucose concentration in normal control mice, streptozotocin (STZ)-treated control mice and STZ-treated transgenic mice following an oral glucose challenge (1.5 g glucose/kg body weight).

Control mice given STZ were severely hyperglycemic both before and after the glucose ingestion (FIG. 12). In contrast, STZ-treated transgenic mice had normal blood glucose levels and rapidly disposed of the oral glucose load as did normal age-matched control mice (FIG. 12).

Figure 13:
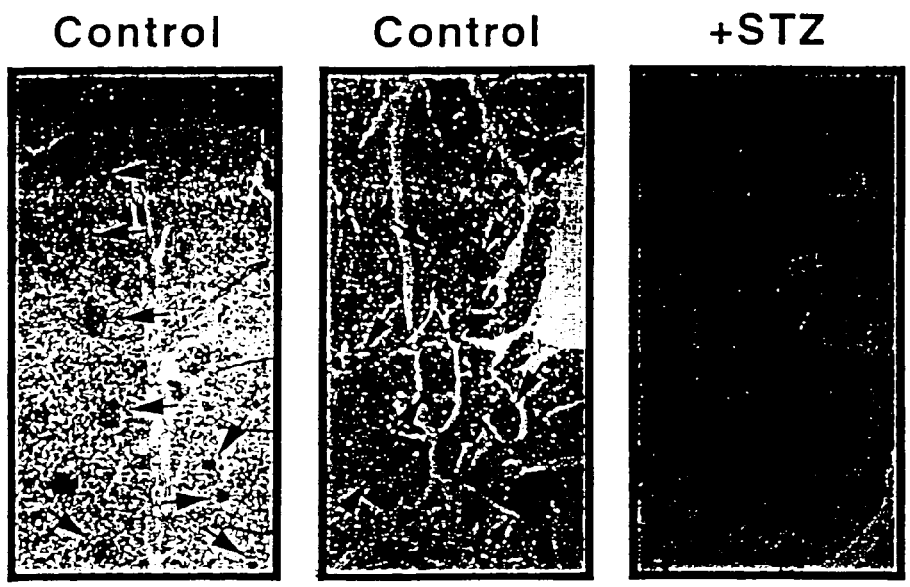
FIG. 13 is a series of micrographs showing immunohistochemical staining for mouse insulin in pancreatic sections from control and STZ-treated transgenic mice. Arrows indicate islets.

To ensure that the STZ treatment effectively destroyed the β-cells in these experimental animals, pancreatic sections from controls and STZ-treated transgenic animals were immunostained for mouse insulin as previously described. The number of cell clusters positively stained for mouse insulin was substantially lower in STZ-treated animals when compared to sham-treated controls (FIG. 13). Total pancreatic content of insulin in STZ-treated transgenic mice was assessed by homogenizing pancreata and sonication at 4° C. in 2 mM acetic acid containing 0.25% BSA. After incubation for 2 hr on ice, tissue homogenates were resonicated, centrifuged (8,000 g, 20 min) and supernatants were assayed for insulin by radioimmunoassayonly. The results indicate that total pancreatic content in STZ-treated transgenic mice was 0.5% that of the sham-treated controls (0.18 vs 34.0 μg insulin per pancreas, n=2). The fact that these STZ-treated transgenic mice disposed of oral glucose like normal mice despite having virtually no pancreatic β-cells indicates that human insulin produced in the gut was sufficient to maintain normal glucose tolerance.

These findings indicate that insulin production from gut K cells can protect the mice from developing diabetes and also provide normal glucose homeostasis to the extent of restoring normal glucose tolerance. Therefore, insulin expressed in gut is a means with which hyperglycemic conditions such as diabetes can be treated.

Example IV

This example describes transplanting a transformed cell that produces a protein in response to nutrient into a tissue of a mammalian subject.

To isolate target mucosal cells, a tissue biopsy will be collected from the duodenum of a subject. The biopsy is washed in ice-cold Hanks' balanced-salt solution (HBSS; Gibco BRL) ~pH 7.4 containing 0.1% bovine serum albumin (BSA; Sigma) and finely chopped with scalpels followed by digestion in an enzyme mixture containing 75 U/ml type I collagenase (Sigma), 75 U/ml type XI collagenase (Sigma), 0.9 U/ml type IX collagenase (Sigma) and 1 U/ml trypsin (Worthington Biochemical Corp) for 1 hour in a shaking water bath at 37° C. The total volume is then doubled with HBSS-BSA and allowed to settle for 10 min. The supernatant containing detached cells is discarded. The remaining tissue is further digested in the enzyme mixture for two 45 min periods, with each step followed by the addition of 300 μl of 0.5 M EDTA for 15 min. The cell suspension resulting from digest 3 is filtered through Nitex mesh (200 μm, B&SH Thompson) and washed and centrifuged at 200×g twice with HBSS-BSA supplemented with 0.01% dithiothreitol and 0.001% DNase. The cells are then filtered a second time through fine Nitex mesh (62 μm, B&SH Thompson), counted, and diluted in HBSS-BSA-DTT-DNase to $6 \times 10^6$ cells/ml for elutriation.

Mucosal endocrine cells will be enriched using a counter-flow centrifugal elutriation of cells (Lindahl P.E. Nature 161:648 (1948), a procedure that separates cells on the basis of their sedimentation coefficients. The cell suspension is pumped into a rotating chamber, and cells are held where their sedimentation rate is balanced by the flow of fluid through the separation chamber. Different fractions of homogeneous cells are then 'eluted' by either increasing the flow rate through the chamber or decreasing the centrifugal speed. The appropriate flow rates and centrifugation speeds are determined empirically. Batches consisting of $1.5 \times 10^8$ dispersed cells are introduced into the Beckman elutriator (model J2-21 M/E; Beckman) via a pump (Cole Palmer) connected to a sterile source of HBSS-BSA.

The enzyme dispersed mucosal cells are loaded into the elutriator chamber at a rotor speed of 2500 rpm with a flow rate of 25 ml/min and washed for 2 min. A 100 ml fraction (F1) is collected after changing the flow rate to 30 ml/min. A second 100 ml fraction (F2) is obtained at a rotor speed of 2100 rpm and a flow rate of 55 ml/min. Cells from F2 are concentrated by centrifuging at 200×g for 10 min, and then resuspended in sterile culture medium (DMEM (47.5%) and Ham's F-12K containing 5.5 mM glucose, 5% fetal calf serum, 2 ng/ml nerve growth factor, 8 mg/L insulin, mg/L hydrocortisone, 50 mg/L gentamycin, 0.25 mg/L amphotericin B, 50 U/ml penicillin, 50 mg/L streptomycin and 20 µM cytosineβ-D-arabinofuranoside.

The resulting mucosal endocrine cells are conditionally immortalized according to Kobayashi et. al. (Science 287: 1258 (2000)). Cultured mucosal cells are transduced with a standard replication incompetent retroviral vector harboring a genetic construct consisting of the GIP promoter operably-linked to an oncogene (e.g. telomerase, large-T antigen, v-myc, ras, among others) tandemly fused to an IRES and a HSV-tk gene. The insulin and selection marker is expressed bi-cistronically. The genetic construct is flanked by recombinase recognition sites to allow for excision of the oncogene and hence deimmortalization of cells prior to transplantation.

To establish an immortalized K cell line, surviving clones of cells—transduced with the retroviral vector carrying the GIP promoter linked to an oncogene—are examined for the expression of GIP by immuno-fluorescence staining and western blotting. Clones that express satisfactory amounts of GIP are further expanded to established a K cell line. The K cell line is further transduced with a retroviral vector carrying a genetic construct consisting of the GIP promoter operably linked to a nucleic acid encoding human insulin and a positive selection marker. The insulin and selection marker is expressed bi-cistronically. The transfected K cells are incubated with appropriate selection drug. Surviving clones are isolated and tested for the expression of human insulin by western blot and ELISA (ALPCO).

K cell clone expressing appropriate levels of human insulin are cultured until sufficient number of cells are obtained. Prior to transplantation into a mammalian subject, the human insulin expressing K cell line is deimmortalized by excision of the oncogene. This is accomplished by transfecting cells with adenovirus expressing the appropriate recombinase (e.g. cre, flp, among others). Twenty-four to forty-eight hour after their transfection, cells are incubated in gancyclovir. After 78 hrs exposure to gancyclovir, surviving cells ($10^6$-$10^{12}$ cells) are purified and prepared for transplantation into a mammalian subject.

As an alternative, mucosal precursor cells or stem cells are isolated from duodenal biopsies by enzymatic (e.g. thermolysin) dissociation and expanded in culture as described previously (Perraeault N. & Beaulieu J. F. *Exp Cell Res* 245:34 (1998); Perraeault N. & Beaulieu J. F. *Exp Cell Res* 224:354 (1996)). These stem cells and precursor cells are transfected with viral vectors carrying the GIP/Ins construct. Cells that are transfected successfully are selected by incubation in selection drug. These genetically engineered cells are then induced to differentiate and finally transplanted into mammalian subjects.

In summary, this example illustrates an ex vivo method for engineering K cells and mucosal endocrine precursor cells to produce human insulin. The engineered cells can be transplanted back into the same subject or to a different subject. The transplantation can be accomplished by several well established methodologies as disclosed herein or known in the art. For example, cells can be encapsulated and implanted under the skin of the mammalian subject or cells can be implanted in the liver through portal delivery.

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating diabetes in a mammalian subject comprising contacting gastrointestinal mucosal tissue cells comprising K cells or stem cells, or multipotent progenitor cells that differentiate into K cells in the subject with a polynucleotide vector comprising a glucose-dependent insulinotropic polypeptide (GIP) promoter in operable linkage with a nucleic acid encoding insulin, wherein said contacting occurs in vivo via intra-cavity delivery to stomach or small intestine, thereby producing transformed K cells, and wherein orally feeding the subject an amount of glucose, sucrose, fructose, carbohydrate, polypeptide, amino acid or fat increases transcription or secretion of the insulin by the transformed cells in an amount effective to decrease blood glucose in the subject, thereby treating diabetes in the mammalian subject.

2. The method of claim 1, wherein the diabetes comprises type 1 diabetes.

3. The method of claim 1, wherein the subject has a fasting plasma glucose level greater than 110 mg/dl prior to treatment.

4. The method of claim 1, wherein the diabetes comprises insulin-independent (type 2) diabetes.

5. The method of claim 1, wherein the glucose increases transcription and secretion of the insulin by the transformed cells.

6. The method of claim 1, wherein the polypeptide or amino acid increases secretion of the insulin by the transformed cells.

7. The method of claim 1, wherein the glucose-dependent insulinotropic polypeptide (GIP) promoter comprises a functional variant or a functional subsequence thereof, and wherein the glucose-dependent insulinotropic polypeptide (GIP) promoter-functional variant or subsequence retains all or a part of non-variant or full-length glucose-dependent insulinotropic polypeptide (GIP) promoter transcription function.

8. The method of claim 1, wherein the K cells, stem cells, or multipotent progenitor cells are present in the small intestine.

9. The method of claim 1, wherein the K cells, stem cells, or multipotent progenitor cells are present in the stomach.

10. The method of claim 1, wherein the vector comprises a viral vector.

11. The method of claim 1, wherein said contacting in vivo via intra-cavity delivery is with an endoscope, feeding tube, cannula, or catheter.

12. The method of claim 1, wherein said contacting in vivo via intra-cavity delivery occurs orally.

13. The method of claim 1, wherein said vector comprises a vector that facilitates integration of the nucleic acid encoding insulin into the genome of said K cells, stem cells, or multipotent progenitor cells.

14. A method of reducing blood glucose in a mammalian subject having undesirable body mass or obesity comprising contacting gastrointestinal mucosal tissue cells comprising K cells or stem cells, or multipotent progenitor cells that differentiate into K cells in the subject with a polynucleotide vector comprising a glucose-dependent insulinotropic polypeptide (GIP) promoter in operable linkage with a nucleic acid encoding leptin, wherein said contacting occurs in vivo via intra-cavity delivery to stomach or small intestine, thereby producing transformed K cells, and wherein orally feeding the subject an amount of glucose, sucrose, fructose, carbohydrate, polypeptide, amino acid or fat increases transcription or secretion of the leptin by the transformed cells in an amount effective to reduce blood glucose in the subject.

15. The method of claim 14, wherein the subject is obese.

16. The method of claim 14, wherein the glucose increases transcription and secretion of the leptin by the transformed cells.

17. The method of claim 14, wherein the glucose-dependent insulinotropic polypeptide (GIP) promoter comprises a functional variant or functional subsequence thereof that retains all or a part of non-variant or full-length glucose-dependent insulinotropic polypeptide (GIP) promoter transcription function.

18. The method of claim 14, wherein the K cells, stem cells, or multipotent progenitor cells are present in the small intestine.

19. The method of claim 14, wherein the K cells, stem cells, or multipotent progenitor cells are present in the stomach.

20. The method of claim 14, wherein the vector comprises a viral vector.

21. The method of claim 14, wherein said contacting in vivo via intra-cavity delivery is with an endoscope, feeding tube, cannula, or catheter.

22. The method of claim 14, wherein said contacting in vivo via intra-cavity delivery occurs orally.

23. The method of claim 14, wherein said vector comprises a vector that facilitates integration of the nucleic acid encoding leptin into the genome of said K cells, stem cells, or multipotent progenitor cells.

24. A method of treating diabetes in a mammalian subject comprising contacting gastrointestinal mucosal tissue cells comprising K cells, or stem cells, or multipotent progenitor cells that differentiate into K cells in the subject with a polynucleotide vector comprising a chromogranin A promoter in operable linkage with a nucleic acid encoding insulin, wherein said contacting occurs in vivo via intra-cavity delivery to stomach or small intestine, thereby producing transformed K cells, and wherein orally feeding the subject an amount of glucose, carbohydrate, polypeptide, amino acid or fat increases secretion of the insulin by transformed K cells in an amount effective to decrease blood glucose in the subject, thereby treating diabetes in the mammalian subject.

25. The method of claim 24, wherein the diabetes comprises type 1 diabetes.

26. The method of claim 24, wherein the subject has a fasting plasma glucose level greater than 110 mg/dl prior to treatment.

27. The method of claim 24, wherein the diabetes comprises insulin-independent (type 2) diabetes.

28. The method of claim 24, wherein the chromogranin A promoter comprises a functional variant or a functional subsequence thereof, and wherein the chromogranin A promoter functional variant or subsequence retains all or a part of non-variant or full-length or chromogranin A promoter transcription function.

29. The method of claim 24, wherein the K cells, or stem cells, or multipotent progenitor cells are present in the small intestine.

30. The method of claim 24, wherein the K cells, or stem cells, or multipotent progenitor cells are present in the stomach.

31. The method of claim 24, wherein the vector comprises a viral vector.

32. The method of claim 24, wherein said contacting in vivo via intra-cavity delivery is with an endoscope, feeding tube, cannula, or catheter.

33. The method of claim 24, wherein said contacting in vivo via intra-cavity delivery occurs orally.

34. The method of claim 24, wherein said vector comprises a vector that facilitates integration of the nucleic acid encoding insulin into the genome of said K cells, or stem cells, or multipotent progenitor cells.

35. A method of reducing blood glucose in a mammalian subject having undesirable body mass or obesity comprising contacting gastrointestinal mucosal tissue cells comprising gut endocrine cells, or stem cells, or multipotent progenitor cells that differentiate into gut endocrine cells in the subject with a polynucleotide vector comprising a chromogranin A promoter in operable linkage with a nucleic acid encoding leptin, wherein said contacting occurs in vivo via intra-cavity delivery to stomach or small intestine, thereby producing transformed gut endocrine cells, and wherein orally feeding the subject an amount of glucose, carbohydrate, polypeptide, amino acid or fat increases secretion of leptin by transformed cells in an amount effective to reduce blood glucose in the subject.

36. The method of claim 35, wherein the subject is obese.

37. The method of claim 35, wherein the chromogranin A promoter comprises a functional variant or functional subsequence thereof that retains all or a part of non-variant or full-length chromogranin A promoter transcription function.

38. The method of claim 35, wherein the gut endocrine cells, or stem cells, or multipotent progenitor cells are present in the small intestine.

39. The method of claim 35, wherein the gut endocrine cells, or stem cells, or multipotent progenitor cells are present in the stomach.

40. The method of claim 35, wherein the gut endocrine cell is a L-cell, S-cell, G-cell, D-cell, Mo-cell, or enteroendocrine cell.

41. The method of claim 35, wherein the vector comprises a viral vector.

42. The method of claim 35, wherein said contacting in vivo via intra-cavity delivery is with an endoscope, feeding tube, cannula, or catheter.

43. The method of claim 35, wherein said contacting in vivo via intra-cavity delivery occurs orally.

44. The method of claim 35, wherein said vector comprises a vector that facilitates integration of the nucleic acid encoding insulin into the genome of said gut endocrine cells, or stem cells, or multipotent progenitor cells.

* * * * *

SEQUENCE LISTING

<160> NUMBER OF SEQ ID NOS: 19

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 1
ccagccgcag cctttgtga                                              19

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 2

```
ggtacagcat tgttccacaa tg                                              22

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 3
accaccagcc ctaagtgat                                                  19

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
ctagttgcag tagttctcca gc                                              22

<210> SEQ ID NO 5
<211> LENGTH: 1319
<212> TYPE: DNA
<213> ORGANISM: Mus musculus

<400> SEQUENCE: 5
ccgaaattac ccactacgtt ggaattctat aagggttggg tttgctgttt tgtttacagc     60
tgcgtctttg gcacccagca cagctgagtg gttctaagcc cacgtcgatg cttaacacat    120
ggttgttgaa tgaatacacg cgaagccggt tctcatttag gggcatgagt aggcagaggt    180
gtgggcagga agcaggaaag agcggaaaca ggtgcggaca gaaaggaggg gctctgaagg    240
atgccagtca gtgccaaact gtcatccaga taccaggttc actgtggccc taggccaggc    300
tgcacggggc ttcccatgtg gtctgcccag ggtgagagca gaactgcggt gggcggggca    360
gaaggaaacc aaccaggaag cagggttgca cccaaattat ccaggtttta agtacattta    420
agagacaagg ctgggctgtt gaaggtcaga ggtgtccctg gggtgctgga ctaggactga    480
ccacttctgt tttagtttaa tggtgagaac tgcctcacac tgctacctgc cttacttgcc    540
ccttgagagc tgtgagccta ggacccaccc atgtgtgggt tggaccttca gtcacacact    600
gaacgtgtgt gaagccactg gttgtcagag cagggctctc ggcactgagg aagcagtgac    660
cactatcccc tatcaaataa caattaaata cacacagaat gcgaggcaca caactgagtt    720
tcaggagagg cctcgctcag gcaagggggtt caagaggctt ctgtgggacc cgctggatgt    780
tccagggagt tcttaaagat gggcgtgcct ccagccaagt gaaatcaaga gaaaagtacg    840
cgaagtatag gaaaactcag cagtctggag aggtaaatag gggaggaatc cgaggctcag    900
agacaggagt gacttgccca cggacgcaca gcaagttggc aggtggagtt cagctgtgcc    960
accttctgaa gccgggtacc ctttacagcc accagataca agcgggatag agacagctga   1020
tggagaagct ggaggtgggg ggcgggaccc cgaaggtggg gaaagggcgc gggggggcgg   1080
tcctatgacg taatttcctg ggtgtgtgcg cgcgtgtgcg tgcgtgtgcg tgtatataaa   1140
agccggcata gcattgctgc tgctgccgcc gccaccgcca ccatcaccgc tgttaccacc   1200
accgctactg cagtgttccc gctggtgcag agctttggta gccagactac agacccactc   1260
ccgccatcct cctgcagcag ctcgtccact ctttccgcac cgtccggctc gctatgcgc    1319
```

<210> SEQ ID NO 6
<211> LENGTH: 1760
<212> TYPE: DNA
<213> ORGANISM: Mus musculus

<400> SEQUENCE: 6

| | | | | | |
|---|---|---|---|---|---|
| gggaactttc | tctagctctt | tcattagggg | ccctgtgttc | catctaatag | ctgactgtga | 60 |
| gcatccactt | ctgtgcttgc | caggcactgg | catagcctca | aagagacag | ctatatcagg | 120 |
| gtcttgtcag | caaaatcttt | ctggcatatg | caatagtgtc | tgggtttggt | ggttgtatat | 180 |
| gggctggatc | cccgggtggg | gcagtctctg | gatggtcttt | ccttccgtct | tagctccaaa | 240 |
| ctttgtctct | gtaactcctt | ccatgggtac | tttgtttccc | attctaagaa | ggagcaaagt | 300 |
| atccacactt | ccttcttctt | ccttcttctt | gagttttgca | aatgccacaa | aacttcaaa | 360 |
| gccttctgaa | tagccttctc | tttagtgctt | tccaatgtat | attaaaataa | tctatctttc | 420 |
| atccccattg | attaaagcct | tcttaaagcc | agaaaactat | attcatttt | ttcttttccc | 480 |
| agtagttcac | aaactatctg | gcacctcata | agcatcataa | ctcagttggt | gggtagataa | 540 |
| aattggaatg | tgattgttca | gtcagcagag | actttagag | gacctcatac | aacaagattc | 600 |
| tctcagttct | cagaaatata | tttcagtata | tacagggtta | gaggactcac | atctttaata | 660 |
| aaataaagtt | aaaatttag | acctgtataa | attattaagg | tacctaatca | agttccacgg | 720 |
| caaagtacag | ccatggttat | gaattataaa | tccaagaagc | ggtgggttaa | ctctgacatt | 780 |
| gttccttgga | tggttctcat | tcattgaagt | tagtcacctc | aacttactca | accaaaacct | 840 |
| agaagtattt | ctgtggtact | atgttctctt | gatgccaaga | gggctctagg | catatgaaaa | 900 |
| tctctcaatc | tctctccctc | tctctccccc | ttccaccccc | actctctctc | ttctagcagt | 960 |
| aatccctccc | ttcctggtag | gcagtatgtt | ttttggagca | cagtttctta | gctatctctt | 1020 |
| gcaacacctg | attttgctga | agatttgaat | ggcctcatat | agaagtatca | acaacttgag | 1080 |
| cgtctgtgaa | ctctcatttt | gacactgtgc | tgaaagaatt | ggagttgatt | ctcattaaaa | 1140 |
| aaaaaattaa | gcatctcacc | tttttgctc | aaactaaaca | gttttaaaac | agttctgcct | 1200 |
| ggagtcatga | tatgaaatac | gatctatcat | atttgcaatg | ttctgttcaa | ttgtggctgc | 1260 |
| accaggaaat | gagaagctat | ttctttatag | gcacaaataa | aaagatagtc | attatctgta | 1320 |
| aaattcttat | gacatggcag | caagcccaag | aaacctttct | aaacaaggcg | tgaaaacgca | 1380 |
| gagatgtcct | tgcaattagt | catgtctatc | tgacagattt | cttcctttct | aagggaattt | 1440 |
| gtgctgaaca | ttttatttcg | agcctcagag | ataaagaag | ggggaagaag | ctgtagtttt | 1500 |
| tgctacataa | gacaggtggc | gtaagcatgc | aacgctttaa | aaaaatatct | aaagtgattg | 1560 |
| ttttctctcg | gattctttga | aaaagctcgc | ctgcgctggg | gtttgaggct | gagccggtga | 1620 |
| cgtcagcgtg | gaatgcggag | tcaggcgccc | aggctctcta | taagccgagg | agctgtccgg | 1680 |
| tgctgaaacg | gcccgagccc | tcactcagcg | gcagagagga | gcatgcttgg | agccttccac | 1740 |
| ataatataag | acagaggtaa | | | | | 1760 |

<210> SEQ ID NO 7
<211> LENGTH: 2623
<212> TYPE: DNA
<213> ORGANISM: Mus musculus

<400> SEQUENCE: 7

| | | | | | |
|---|---|---|---|---|---|
| agctttaggt | gtgtgaatat | ctactttggt | gctagggcct | tggtcatact | aagtaagttt | 60 |
| cccctttcact | ggggtgtacc | agtttaccct | ggactgtcta | agcaacaaga | aggatagaca | 120 |

```
tggcctacca cagatttcat gtctgccact ggctatgtca gaacatgtag gagcttttgg      180
aatcagtgaa acaggtattt tcagactgcc ttccctgcgt ggggctttcc cgaagccata      240 ttttcctag agtcagcctt tcccagctga ggacaagctg tactggacag atgccagcca      300
cttgaactgg gaatacatgg tcatttaggc agctggctta tctcatccat ggtacttgat      360
ggcttcgggt cagcacctca cagaaagttc agacgggagg cttccgagaa acagagaag      420 caggcaggag atcctgcagg caatcctcct gctccacagc ctgcatggac ttccctcagc      480
cttagtgcgt gtgggtccca tctgagaaca ttggttatat gttatttca aaccgatctg      540 cctttaagga gtggaagaaa aaactgtgg tgtttgggct acctttatga taatggcctt      600
ttcatcctcc taataaatat tgccaagtag ggtagattct atacgaaagc tcttaaccca      660
tggtattagc aaatcatgta ggtgctaata atgaatactg gatgcagtca gtacagggat      720
ataaaatgga atgtaagagc ctgttgctat gaatggttag ctaactagat gttgtacaag      780
aaatgttgac gttatgacgt gtggaaactt ggtattgaag atgtggactc gaaactttgt      840
ggattttttg atgccatgat aaaaatgtga agaatactgt tccttaccaa aagaagaag      900 aagaaggaga aggaggagga agaggaggag gaggaagaag aggggagga agaagaagag      960 aaggaggagg aagaggagga ggaggaagaa gaggaggagg aggaagaaga agagaaggag     1020
gaggactagg aggaggagga gaagaaggag aaggggaagg agagagtagc cagaacattt     1080
ggggtgccat cagaatacca gatactccag acatagtcac agaaggactg gtttgtttgt     1140
taaataggtg ctttgaaaag tttgtgggga acctgcagt gagattgtgt gtcttagaaa      1200
tgataggcaa gattcatcca caagaatgcg acaagatggc tgcctgaaca agccctgaac     1260
attaacagca ccagtagacc tgcttacacg gaagaaagca atctcatagg ccctcacccc     1320
aaacaaagac tacagacagc agaggaactg gagagcagga gaaattgggt ctcccttta     1380 tgagcccct aactggttgt caaatactca atggtcagcc ctgaaatcat atgcacaaag      1440
taatactagc gcaactgaac agattgtagc tgtgtgtgtg tgtgtaatga taacaaagaa     1500
gaaaaggccc catgttagag agggagcaag gtgggcatgg aggtatggaa ggagttggaa     1560
ggaggggtga gaaggggaaa gtgatgtaat tatctttaa tttataaaa aataaaaaat      1620 gggctggtga gatggctcag tgggtaagag caccgactg cttcttccga aggtctggag      1680
ttcaaatccc agcaaccaca tggtggctca caaccatccg taacgagatc tggcgccctc     1740
ttctggagtg tctgaagaca gctacagtgt acttacatat aataaataaa taatctttt     1800 aaaaaaaata aaaaataaaa tattagaata aaatgtagag gaatatttt aatttaacaa     1860 cttgggtgtg gcaaaagctt tcttcaacaa aaacttaatc cctcagataa gaaaagacta     1920
gaatccacga cgtggataga tacttctgta tgatgcaaga cactatttat caggttgtaa     1980
cttgagcaga acttgagttg taacttgttg ggaaacacaa caccccttggc aaacaaaaga     2040 ttactagata tttagatga aatataaaaa tactttccac aactgatagg taggaaacag     2100 tcaatagta atataattat tgaacaaata atccttaaaa gaagaaatcc agaggaatag      2160
caagttaggg gaagagaggg tgtgtgtgtg tgtgtgtgcg cgcacattta tagccaaaat     2220
agatgatata cttaaatgaa catgccatta aaacccatta ttttgcatac agtttacata     2280
tgctaatgaa tacttaaaaa aaaaacattg ggattggaga gaaatggctc agtggttaag     2340
agttcaattc ccagcaacca catgattgct cacaaccatc tgtaatggga tctgatgcct     2400
tcttctggta tgtctgaaga aagtgaccgt gtacttataa ttataaataa ataaatcttt     2460
```

-continued

```
aaccaaaaaa cccccataat ttcaacaaca gatatgtcct ggtctgaggc ttccaggcat    2520
agaaatagaa acacacagag tgtggagcca gtgcggttca ggtccgccat tccagttcag    2580
gcttcagacc aagagaaagg gaaaagaaga gacaagcaac aag                      2623
```

<210> SEQ ID NO 8
<211> LENGTH: 226
<212> TYPE: DNA
<213> ORGANISM: Homo sapiens

<400> SEQUENCE: 8

```
tccaggaaat gcgcgatcca ggccggcggg cggggcgggg gctccggcga gagggcgggc      60
cccgggaacg gcggcgggcg gggcgggagg cggggcccgg cccgttaaga agagcgtggc     120
cggccgcggc caccgctggc cccagggaaa gccgagcggc caccgagccg gcagagaccc     180
accgagcggc ggcggaggga gcgacgccgg ggcgcacgag ggcacc                    226
```

<210> SEQ ID NO 9
<211> LENGTH: 110
<212> TYPE: PRT
<213> ORGANISM: Homo sapiens

<400> SEQUENCE: 9

```
Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn Gln His Leu Cys Gly
                20                  25                  30

Ser His Leu Val Glu Ala Leu Tyr Leu Val Cys Gly Glu Arg Gly Phe
            35                  40                  45

Phe Tyr Thr Pro Lys Thr Arg Arg Glu Ala Glu Asp Leu Gln Val Gly
        50                  55                  60

Gln Val Glu Leu Gly Gly Gly Pro Gly Ala Gly Ser Leu Gln Pro Leu
    65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
                100                 105                 110
```

<210> SEQ ID NO 10
<211> LENGTH: 450
<212> TYPE: DNA
<213> ORGANISM: Homo sapiens

<400> SEQUENCE: 10

```
gctgcatcag aagaggccat caagcacatc actgtccttc tgccatggcc ctgtggatgc     60
gcctcctgcc cctgctggcg ctgctggccc tctggggacc tgacccagcc gcagcctttg    120
tgaaccaaca cctgtgcggc tcacacctgg tggaagctct ctacctagtg tgcggggaac    180
gaggcttctt ctacacaccc aagacccgcc gggaggcaga ggacctgcag gtggggcagg    240
tggagctggg cggggggccct ggtgcaggca gcctgcagcc cttggccctg gaggggtccc    300
tgcagaagcg tggcattgtg gaacaatgct gtaccagcat ctgctccctc taccagctgg    360
agaactactg caactagacg cagcccgcag gcagcccccc accgccgcc tcctgcaccg     420 agagagatgg aataaagccc ttgaaccagc                                     450
```

<210> SEQ ID NO 11
<211> LENGTH: 167
<212> TYPE: PRT

<213> ORGANISM: Homo sapiens

<400> SEQUENCE: 11

```
Met His Trp Gly Thr Leu Cys Gly Phe Leu Trp Leu Trp Pro Tyr Leu
 1               5                  10                  15

Phe Tyr Val Gln Ala Val Pro Ile Gln Lys Val Gln Asp Asp Thr Lys
             20                  25                  30

Thr Leu Ile Lys Thr Ile Val Thr Arg Ile Asn Asp Ile Ser His Thr
         35                  40                  45

Gln Ser Val Ser Ser Lys Gln Lys Val Thr Gly Leu Asp Phe Ile Pro
     50                  55                  60

Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165
```

<210> SEQ ID NO 12
<211> LENGTH: 3408
<212> TYPE: DNA
<213> ORGANISM: Homo sapiens

<400> SEQUENCE: 12

```
tctgttttca ggcccaagaa gcccatcctg ggaaggaaaa tgcattgggg aaccctgtgc      60
ggattcttgt ggctttggcc ctatctttc tatgtccaag ctgtgcccat ccaaaaagtc     120
caagatgaca ccaaaaccct catcaagaca attgtcacca ggatcaatga catttcacac     180
acgcagtcag tctcctccaa acagaaagtc accggtttgg acttcattcc tgggctccac     240
cccatcctga ccttatccaa gatggaccag acactggcag tctaccaaca gatcctcacc     300
agtatgcctt ccagaaacgt gatccaaata tccaacgacc tggagaacct ccgggatctt     360
cttcacgtgc tggccttctc taagagctgc cacttgccct gggccagtgg cctggagacc     420
ttggacagcc tgggggggtgt cctggaagct tcaggctact ccacagaggt ggtggccctg     480
agcaggctgc aggggtctct gcaggacatg ctgtggcagc tggacctcag ccctgggtgc     540
tgaggccttg aaggtcactc ttcctgcaag gactacgtta agggaaggaa ctctggcttc     600
caggtatctc caggattgaa gagcattgca tggacacccc ttatccagga ctctgtcaat     660
ttccctgact cctctaagcc actcttccaa aggcataaga ccctaagcct cctttttgctt     720
gaaaccaaag atatatacac aggatcctat tctcaccagg aagggggtcc acccagcaaa     780
gagtgggctg catctgggat cccaccaag gtcttcagcc atcaacaaga gttgtcttgt     840
cccctcttga cccatctccc cctcactgaa tgcctcaatg tgaccagggg tgatttcaga     900
gagggcagag gggtaggcag agcctttgga tgaccagaac aaggttccct ctgagaattc     960
caaggagttc catgaagacc acatccacac acgcaggaac tccagcaac acaagctgga    1020
```

```
agcacatgtt tatttattct gcattttatt ctggatggat ttgaagcaaa gcaccagctt    1080
ctccaggctc tttggggtca gccagggcca ggggtctccc tggagtgcag tttccaatcc    1140
catagatggg tctggctgag ctgaacccat tttgagtgac tcgagggttg ggttcatctg    1200
agcaagagct ggcaaaggtg gctctccagt tagttctctc gtaactggtt tcatttctac    1260
tgtgactgat gttacatcac agtgtttgca atggtgttgc cctgagtgga tctccaagga    1320
ccaggttatt ttaaaaagat ttgttttgtc aagtgtcata tgtaggtgtc tgcacccagg    1380
ggtgggaat gtttgggcag aagggagaag gatctagaat gtgttttctg aataacattt    1440
gtgtggtggg ttcttttggaa ggagtgagat cattttctta tcttctgcaa ttgcttagga    1500
tgtttttcat gaaaatagct ctttcagggg ggttgtgagg cctggccagg cacccccctgg   1560
agagaagttt ctggccctgg ctgacccca agagcctgga gaagctgatg ctttgcttca     1620
aatccatcca gaataaaacg caaagggctg aaagccattt gttggggcag tggtaagctc    1680
tggctttctc cgactgctag ggagtggtct ttcctatcat ggagtgacgg tcccacactg    1740
gtgactgcga tcttcagagc aggggtcctt ggtgtgaccc tctgaatggt ccagggttga    1800
tcacactctg ggtttattac atggcagtgt tcctatttgg ggcttgcatg ccaaattgta    1860
gttcttgtct gattggctca cccaagcaag gccaaaatta ccaaaaatct tggggggttt    1920
ttactccagt ggtgaagaaa actcctttag caggtggtcc tgagacctga caagcactgc    1980
taggcgagtg ccaggactcc ccaggccagg ccaccaggat ggcccttccc actggaggtc    2040
acattcagga agatgaaaga ggaggttttgg ggtctgccac catcctgctg ctgtgttttt    2100
gctatcacac agtgggtggt ggatctgtcc aaggaaactt gaatcaaagc agttaacttt    2160
aagactgagc acctgcttca tgctcagccc tgactggtgc tataggctgg agaagctcac    2220
ccaataaaca ttaagattga ggcctgccct cagggatctt gcattcccag tggtcaaacc    2280
gcactcaccc atgtgccaag gtggggtatt taccacagca gctgaacagc caaatgcatg    2340
gtgcagttga cagcaggtgg gaaatggtat gagctgaggg gggccgtgcc caggggccca    2400
cagggaaccc tgcttgcact ttgtaacatg tttactttttc agggcatctt agcttctatt    2460
atagccacat ccctttgaaa caagataact gagaatttaa aaataagaaa atacataaga    2520
ccataacagc caacaggtgg caggaccagg actatagccc aggtcctctg atacccagag    2580
cattacgtga gccaggtaat gagggactgg aaccagggag accgagcgct ttctggaaaa    2640
gaggagtttc gaggtagagt ttgaaggagg tgagggatgt gaattgcctg cagagagaag    2700
cctgttttgt tggaaggttt ggtgtgtgga gatgcagagg taaaagtgtg agcagtgagt    2760
tacagcgaga ggcagagaaa gaagagacag gagggcaagg gccatgctga agggaccttg    2820
aagggtaaag aagtttgata ttaaaggagt taagagtagc aagttctaga gaagaggctg    2880
gtgctgtggc cagggtgaga gctgctctgg aaaatgtgac ccagatcctc acaaccacct    2940
aatcaggctg aggtgtctta agccttttgc tcacaaaacc tggcacaatg gctaattccc    3000
agagtgtgaa acttcctaag tataaatggt tgtctgtttt tgtaacttaa aaaaaaaaaa    3060
aaaagtttgg ccgggtgcgg tggctcacgc ctgtaatccc agcactttgg gaggccaagg    3120
tgggggatc acaaggtcac tagatggcga gcatcctggc caacatggtg aaaccccgtc      3180
tctactaaaa acacaaaagt tagctgagcg tggtggcggg cgcctgtagt cccagccact    3240
cgggaggctg agacaggaga atcgcttaaa cctgggaggc ggagagtaca gtgagccaag    3300
atcgcgccac tgcactccgg cctgatgaca gagcgagatt ccgtcttaaa aaaaaaaaa    3360
aaaaagtttg ttttaaaaa aatctaaata aaataacttt gccccctg                 3408
```

<210> SEQ ID NO 13
<211> LENGTH: 136
<212> TYPE: PRT
<213> ORGANISM: Homo sapiens

<400> SEQUENCE: 13

```
Gly Ser Ala Ala Gly Leu Leu Arg Leu Glu Thr Pro Ser Gln Leu Arg
  1               5                  10                  15
Pro Asn Pro Lys Ala Met Asn Ser Gly Val Cys Leu Cys Val Leu Met
                 20                  25                  30
Ala Val Leu Ala Ala Gly Ala Leu Thr Gln Pro Val Pro Pro Ala Asp
             35                  40                  45
Pro Ala Gly Ser Gly Leu Gln Arg Ala Glu Glu Ala Pro Arg Arg Gln
         50                  55                  60
Leu Arg Val Ser Gln Arg Thr Asp Gly Glu Ser Arg Ala His Leu Gly
 65                  70                  75                  80
Ala Leu Leu Ala Arg Tyr Ile Gln Gln Ala Arg Lys Ala Pro Ser Gly
                 85                  90                  95
Arg Met Ser Ile Val Lys Asn Leu Gln Asn Leu Asp Pro Ser His Arg
                100                 105                 110
Ile Ser Asp Arg Asp Tyr Met Gly Trp Met Asp Phe Gly Arg Arg Ser
            115                 120                 125
Ala Glu Glu Tyr Glu Tyr Pro Ser
        130                 135
```

<210> SEQ ID NO 14
<211> LENGTH: 685
<212> TYPE: DNA
<213> ORGANISM: Homo sapiens

<400> SEQUENCE: 14

| ggctcagctg ccgggctgct ccggttggaa acgccaagcc agctgcgtcc taatccaaaa | 60 |
| gccatgaaca gcggcgtgtg cctgtgcgtg ctgatggcgg tactggcggc tggcgccctg | 120 |
| acgcagccgg tgcctcccgc agatcccgcg ggctccgggc tgcagcgggc agaggaggcg | 180 |
| ccccgtaggc agctgagggt atcgcagaga acggatggcg agtcccgagc cacctgggc | 240 |
| gccctgctgg caagatacat ccagcaggcc cggaaagctc cttctggacg aatgtccatc | 300 |
| gttaagaacc tgcagaacct ggaccccagc cacaggataa gtgaccggga ctacatgggc | 360 |
| tggatggatt ttggccgtcg cagtgccgag gagtatgagt accctcctca gaggacccag | 420 |
| ccgccatcag cccaacggga agcaacctcc caacccagag gaggcagaat aagaaaacaa | 480 |
| tcacactcat aactcattgt ctgtggagtt tgacattgta tgtatctatt tattaagttc | 540 |
| tcaatgtgaa aaatgtgtct gtaagattgt ccagtgcaac cacacacctc accagaattg | 600 |
| tgcaaatgga agacaaaatg ttttcttcat ctgtgactcc tggtctgaaa atgttgttat | 660 |
| gctattaaag tgatttcatt ctgcc | 685 |

<210> SEQ ID NO 15
<211> LENGTH: 1362
<212> TYPE: DNA
<213> ORGANISM: Rattus sp.

<400> SEQUENCE: 15

| aattcgcgcg ctaagccgca ttattcacgt ttccagacat gtcacaaata cagctaattc | 60 |
| ctacaacctg agctgtgtca tggggggggg gggaatcacc cacagcattt aatctgctgc | 120 |

```
tgttttaaac acgttgcttc taagtaaaga gaccgctaga gccacaacca ggaacctaac    180
tgctgctggc atcacttgcc ttttcatagt ctccctcagc cggaaccccc ccacgctggg    240
tgccttctct atttagaaag agtttctaag cctttctcct tcaccctaga ctggcaaggt    300
tgagggtagg ctgagggttg caagactgtg agaaaaggga gccctctct tcttcttgct     360
cggtgagtat ctcagccaag atcctcacca cccagtggaa tcccgtaact ctagaggaaa    420
ggaagaactc tagaggacgg gaagatcatt gcaagctccc ctagatgtgc gagcccagcc    480
cgctccactc agccagccag agcttgaggg tgcttgagac actctctggc gccacttcgc    540
gaccaaaatc atcggtagat gtaggctggt gagaagtcat cttgggaaga aatggaaacc    600
ttttccccaa aggctttccg cacaaaaggc aagagctgca cccaggatct taaaattctg    660
taagacgaga atccacgagg ccaactgtga ttgagttctg aaaaattgag agccctactc    720
ccctctctca cttgtgggag cccactcagg tctgaagtgc tcccagagaa catgccagaa    780
ttacatttgc tgacacctag tctgtgaggg tcccccggtt tcctggaagg atttgatccc    840
tcaaagctca ctaaacagtg gtcagcttct ccattccaga caaactcctg cttctctccg    900
ggagtagggg tggcaccctc cctgaagagg actcagcaga ggcaccgaac agggtgggga    960
ggaaagctgt ttagataaag aggaggactc atacaaagta ccccgcctgg gaggggctat   1020
cctcattcac tgggccgttt ccttctcccg ggggggccac ttcgatcggt ggtctctcca   1080
gtggctgcct ctgagcacgt gtcctgccgg actgcgtcag cactgggtaa acagatgact   1140
ggctgcgtac cgggcgggc tatttaagag gagtcgccct gccgcctgcc ctcaacttag    1200
ctggacagca gccgttggaa accgccaagc cagctgactc cgcatccgaa ggtaagtggc   1260
tggcagatcc aagaatcatg agtgtgaaga actggcctgt agctttgcat ctattgccgt   1320
ttagtctttc cattttctgt gccttccctc acttgacagc tg                       1362
```

<210> SEQ ID NO 16
<211> LENGTH: 217
<212> TYPE: PRT
<213> ORGANISM: Homo sapiens

<400> SEQUENCE: 16

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
             20                  25                  30

Ser Arg Pro Phe Asp Asn Ala Met Leu Arg Ala His Arg Leu His Gln
         35                  40                  45

Leu Ala Phe Asp Thr Tyr Gln Glu Phe Glu Glu Ala Tyr Ile Pro Lys
     50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
```

```
                145                 150                 155                 160
Thr Gly Gln Ile Phe Lys Gln Thr Tyr Ser Lys Phe Asp Thr Asn Ser
                    165                 170                 175
His Asn Asp Asp Ala Leu Leu Lys Asn Tyr Gly Leu Leu Tyr Cys Phe
            180                 185                 190
Arg Lys Asp Met Asp Lys Val Glu Thr Phe Leu Arg Ile Val Gln Cys
        195                 200                 205
Arg Ser Val Glu Gly Ser Cys Gly Phe
    210                 215

<210> SEQ ID NO 17
<211> LENGTH: 799
<212> TYPE: DNA
<213> ORGANISM: Homo sapiens

<400> SEQUENCE: 17
cgaaccactc agggtcctgt ggacagctca cctagctgca atggctacag gctcccggac      60
gtccctgctc ctggcttttg gcctgctctg cctgccctgg cttcaagagg gcagtgcctt     120
cccaaccatt cccttatcca ggccttttga caacgctatg ctccgcgccc atcgtctgca     180
ccagctggcc tttgacacct accaggagtt tgaagaagcc tatatcccaa aggaacagaa     240
gtattcattc ctgcagaacc cccagacctc cctctgtttc tcagagtcta ttccgacacc     300
ctccaacagg gaggaaacac aacagaaatc aacctagag ctgctccgca tctccctgct     360
gctcatccag tcgtggctgg agcccgtgca gttcctcagg agtgtcttcg ccaacagcct     420
ggtgtacggc gcctctgaca gcaacgtcta tgacctccta aggacctag aggaaggcat     480 ccaaacgctg atggggaggc tggaagatgg cagcccccgg actgggcaga tcttcaagca     540
gacctacagc aagttcgaca caaactcaca caacgatgac gcactactca gaactacgg     600 gctgctctac tgcttcagga aggacatgga caaggtcgag acattcctgc gcatcgtgca     660
gtgccgctct gtggagggca gctgtggctt ctagctgccc gggtggcatc cctgtgaccc     720
ctccccagtg cctctcctgg ccctggaagt tgccactcca gtgcccacca gccttgtcct     780
aataaaatta agttgcatc                                                   799

<210> SEQ ID NO 18
<211> LENGTH: 1167
<212> TYPE: DNA
<213> ORGANISM: Rattus sp.

<400> SEQUENCE: 18
atctctccag tcccttcctc aaccttctga gaacaggcaa actccaccat gattggctta      60
taaatcgtta tatggaccta ctaaggatgt aacaactggg agcatgctta cctagcatgt     120
ccgaaacccg gagttcagtc cctagcactg cacaatctca gtccttatga agtagaggga     180
agatcagagg ttcaaggaca acatcaattt gagaccagcc tgggctactt accaaagaaa     240
gaaagagaga aataaataaa tagatagata aataaataaa taagtaaata aatatcttat     300
ggctggagag ttggttcagt gtttaagagc acttattgtg gggttgggga tttatctcag     360
tggtagagcg tttgcctagg aagctcaagg ccctgggttc ggtccccagc tccggaaaca     420
aaacaaaaca aaacaaaaac aaacaaacaa acaaaaaacc ctgtctgaa acacctaaa      480 taaagatata tatatataat atatatacat ataatatata tatgatatat atatatatat     540
atatctttgt ggaggaagct ataccttct tccttgagcc tccaacacat aaatgtgccc     600
tgtcatccca ttcatattgc cccaagtggg aaaccatgtg actataaact ctaagttcct     660
```

```
agtcactagg aactctcaag acacctacct caggcagcat cacttccgga gtgccaccat    720
tatcagttaa catccacatc tgggattcag atcccagatc ccttctgttc cctcagaagt    780
cacctacagc tttgtggggg tgccccttcc ctcagagagt gccacccgag ttgaccctca    840
ccaaggcaac cctttgtacc cacagaatcc aacaggaagt agggggaaga acagccggcc    900
ctgtgcccag aaaaaagag gggagggaga aggggtgct cagcctacca ccgggcaggt    960
cccagataac actgcagata cccaaatgtt aatcacccat tagcacaggc ccagagcaaa   1020
ggggaaagtg attaggtgta taatgggggtt cactgggcag gagcagtggg cttgagcttc   1080
aaagataaga ggttttcagg ttaatcagca ccctgtggtg tgtggatata aggaagctaa   1140
cacagggtct tgaagcaaga tcctgag                                      1167

<210> SEQ ID NO 19
<211> LENGTH: 1891
<212> TYPE: DNA
<213> ORGANISM: Rattus sp.

<400> SEQUENCE: 19
gagtggcgac aggctgctgc tagcaggctc tacactgagc taaccccacc catatatata     60
catagttact attagcttta tttatatttt taagattatc attatatata tagtacactg    120
tagtgtctag atacacagaa gaggcatcgg tctcttacag agagccacca tgtggttgct    180
ggggattgaa ctcatacctc tggcagagca gtcggtgctc ttaacgctga gccatctctc    240
cagcgccccc aaagcccagc ttttaaaaat attttaaaat ttctttctac agattgtttt    300
atgtatatga gtgttttgtg tgtatgcgtt gatgtgtgta ctgtgtgcat ggcacatgcc    360
agtgggccac agacagaggg acatgagatt ccctgaaac ttggagttac agatggctgt    420
gggctgccat gtgagtgagc gcctttggaa ccaaacctgg gtcctgcaca aaagcaacaa    480
gcactcttaa tcgttgagcc acctctccaa cccttgata tttctttcgt tggtgcatta    540
aaattgataa acagagggtt ttctttattt aaagatttat ttattttatg tgagtacact    600
gttgctctct tcagacacat agaagagggc attgctggat tctgctacag atggttgtga    660
gccaccatgt ggttgctggg agttaaactc aggacctctg gaagagcagt cagtgctctt    720
aaccactgag ccatctctcc agtcccttcc tcaaccttct gagaacaggc aaactccacc    780
atgattggtt ataaatcgtt atatggacct actaaggatg taacaactgg gagcatgctt    840
acctagcatg tccgaaaccc ggagttcagt ccctagcact gcacaatctc agtccttatg    900
aagtagaggg aagatcagag gttcaaggac aacatcaatt tgagaccagc ctgggctact    960
taccaaagaa agaagagag aaataaataa atagatagat aaataaataa ataagtaaat   1020
aaatatctta tggctggaga gttggttcag tgtttaagag cacttattgt ggggttgggg   1080
atttatctca gtggtagagc gttttgcctag gaagctcaag gccctgggtt cggtccccag   1140
ctccggaaac aaaacaaaac aaaacaaaac aaacaaacaa acaaaaaacc ctgtctggaa   1200
aacacctaaa taaagatata tatatataat atatatacat ataatatata tatgatatat   1260
atatatatat atatctttgt ggaggaagct ataccttct ttcttgagcc tccaacacat   1320
aaatgtgccc tgtcatccca ttcatattgc cccaagtggg aaaccatgtg actataaact   1380
ctaagttcct agtcactagg aactctcaag acacctacct caggcagcat cacttccgga   1440
gtgccaccat tatcagttaa catccacatc tgggattcag atcccagatc ccttctgttc   1500
cctcagaagt cacctacagc tttgtggggg tgccccttcc ctcagagagt gccacccgag   1560
```

-continued

```
ttgaccctca ccaaggcaac cctttgtacc cacagaatcc aacaggaagt aggggggaaga    1620 acagccggcc ctgtgccaga aaaaagagg ggagggagaa ggggggtgctc agcctaccac     1680 cgggcaggtc ccagataaca ctgcagatac ccaaatgtta atcacccatt agcacaggcc    1740
cagagcaaag gggaaagtga ttaggtgtat aatggggttc actgggcagg agcagtgggc    1800
ttgagcttca aagataagag gttttcaggt taatcagcac cctgtggtgt gtggatataa    1860
ggaagctaac acagggtctt gaagcaagat c                                   1891
```